(12) United States Patent
Naleway et al.

(10) Patent No.: US 9,925,271 B2
(45) Date of Patent: *Mar. 27, 2018

(54) TARGETED PHARMACOLOGICAL CHAPERONES

(71) Applicant: Marker Gene Technologies, Inc., Eugene, OR (US)

(72) Inventors: John Joseph Naleway, Eugene, OR (US); Fiona Karen Harlan, Eugene, OR (US); Jason Scott Lusk, Eugene, OR (US)

(73) Assignee: Marker Gene Technologies, Inc, Eugene, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/477,569

(22) Filed: Apr. 3, 2017

(65) Prior Publication Data

US 2017/0216451 A1 Aug. 3, 2017

Related U.S. Application Data

(62) Division of application No. 14/689,267, filed on Apr. 17, 2015, now Pat. No. 9,610,358.

(60) Provisional application No. 61/995,611, filed on Apr. 17, 2014, provisional application No. 62/176,131, filed on Feb. 9, 2015.

(51) Int. Cl.
| | | |
|---|---|---|
| A61K 38/00 | (2006.01) | |
| C07K 9/00 | (2006.01) | |
| A61K 47/48 | (2006.01) | |
| A61K 47/64 | (2017.01) | |
| A61K 31/445 | (2006.01) | |

(52) U.S. Cl.
CPC ...... *A61K 47/48246* (2013.01); *A61K 31/445* (2013.01); *A61K 47/64* (2017.08); *A61K 47/645* (2017.08)

(58) Field of Classification Search
None
See application file for complete search history.

*Primary Examiner* — Jeanette Lieb
(74) *Attorney, Agent, or Firm* — Timothy L. McCutcheon

(57) ABSTRACT

The present invention relates to the preparation and use of therapeutic compounds for the treatment of diseases at specific subcellular target areas such as specific cellular organelles. In particular, the therapeutic compounds of the invention are specific for modifying enzyme activity within targeted organelles or structures of cells and tissues. Subcellular organelles and structures that may be specifically targeted by compounds of the present invention include lysosomes, autophagasomes, the endoplasmic reticulum, the Golgi complex, peroxisomes, the nucleus, membranes and the mitochondria.

13 Claims, 12 Drawing Sheets

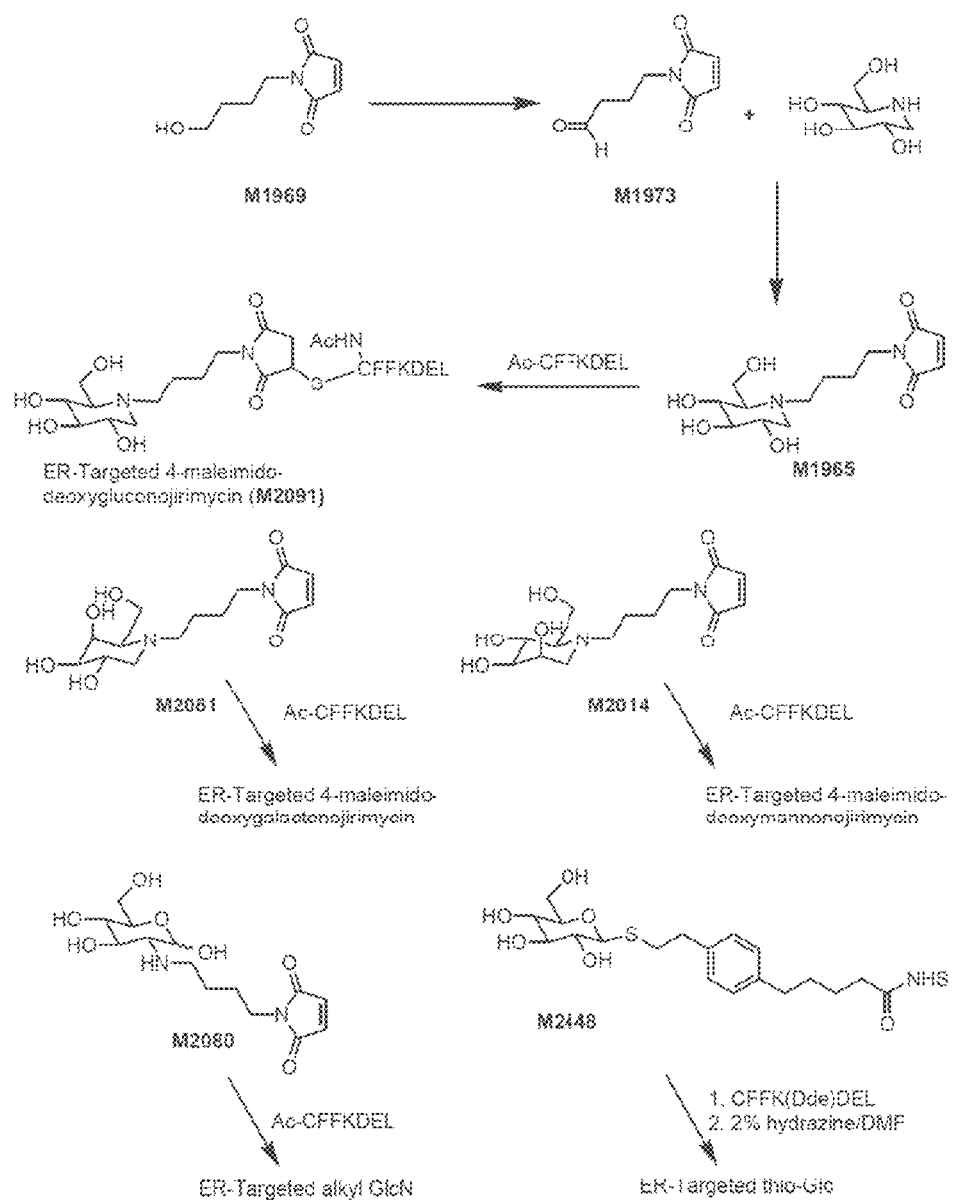
Figure 1. Synthesis of representative ER-targeted Deoxynojirimycin, ER-targeted Deoxygalactonojirimycin, ER-targeted Deoxygalactonojirimycin, ER-targeted Alkyl GlcN, and ER-targeted 1-thio-deoxyglucose.

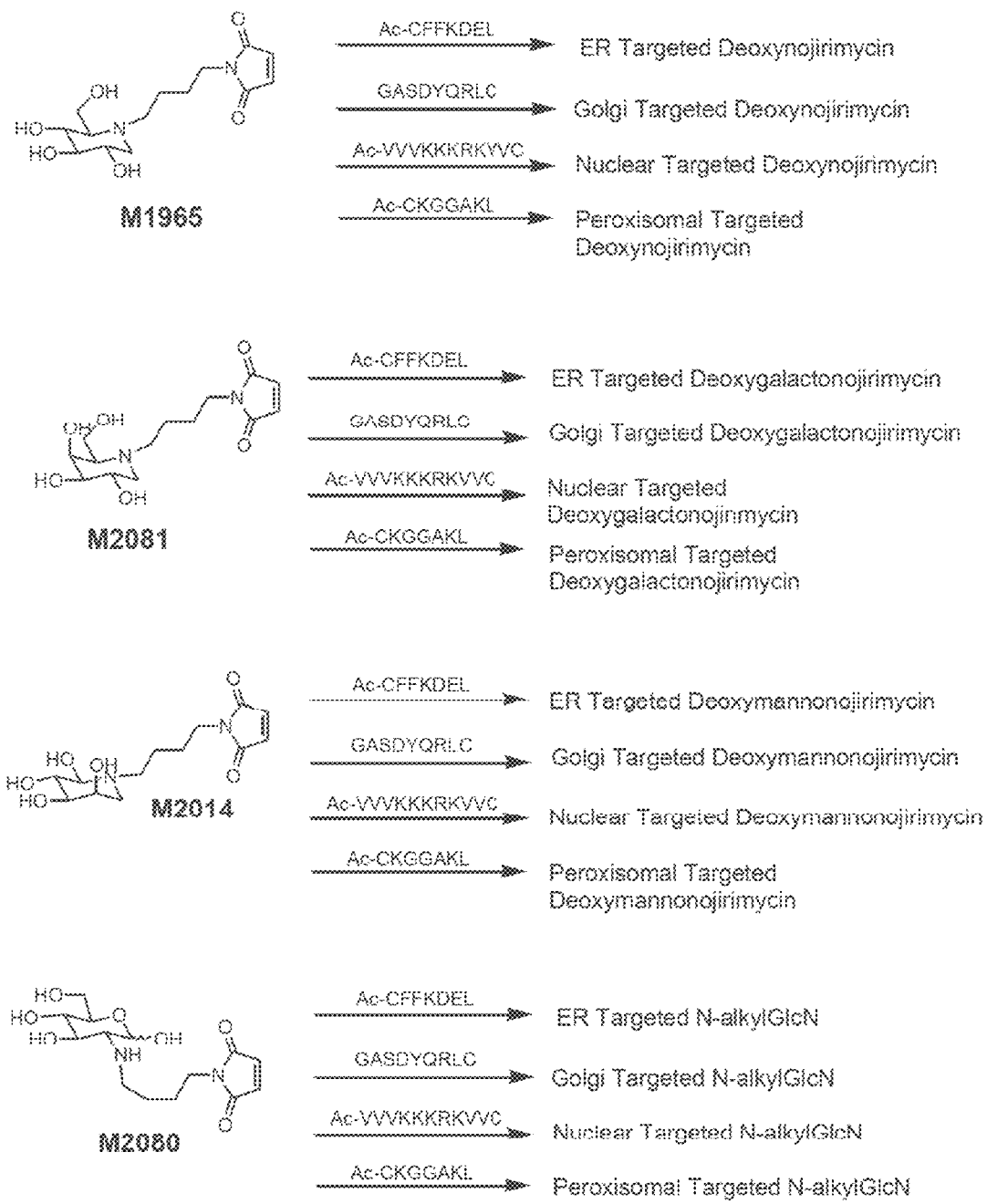
Figure 2. Synthesis of representative ER-targeted, Golgi-targeted, nucleus-targeted and peroxisome-targeted versions of Deoxynojirimycin, Deoxygalactonojirimycin, Deoxygalactonojirimycin and N-alkylglucosamine.

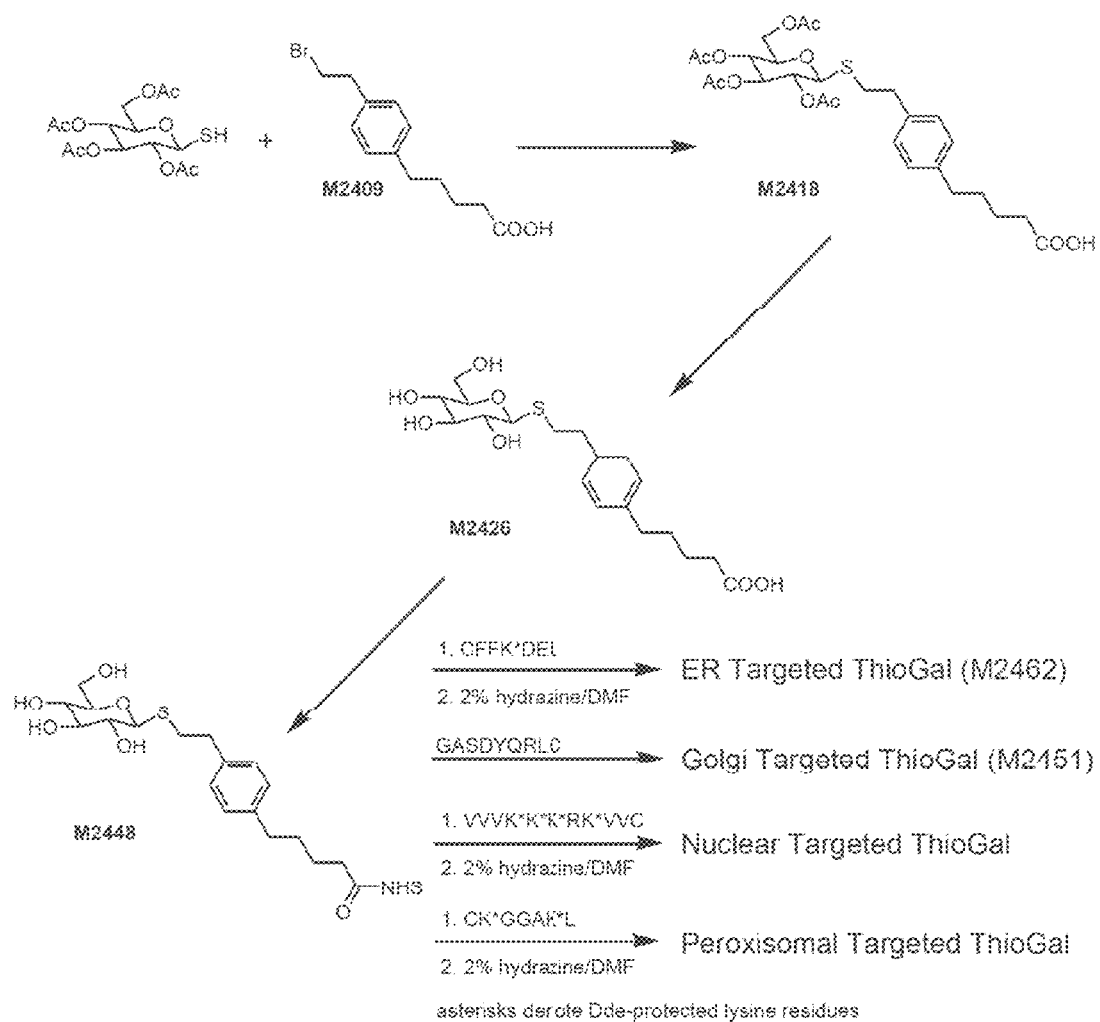
Figure 3. Synthesis of representative ER-targeted, Golgi-targeted, nucleus-targeted and peroxisome-targeted versions of 1-Thio-deoxyglucose.

TPCs Using Direct Peptide Coupling Method

Figure 4. Synthesis of representative ER-targeted, Golgi-targeted, nuclear-targeted and peroxisome-targeted versions of Deoxynojirimycin by direct peptide coupling.

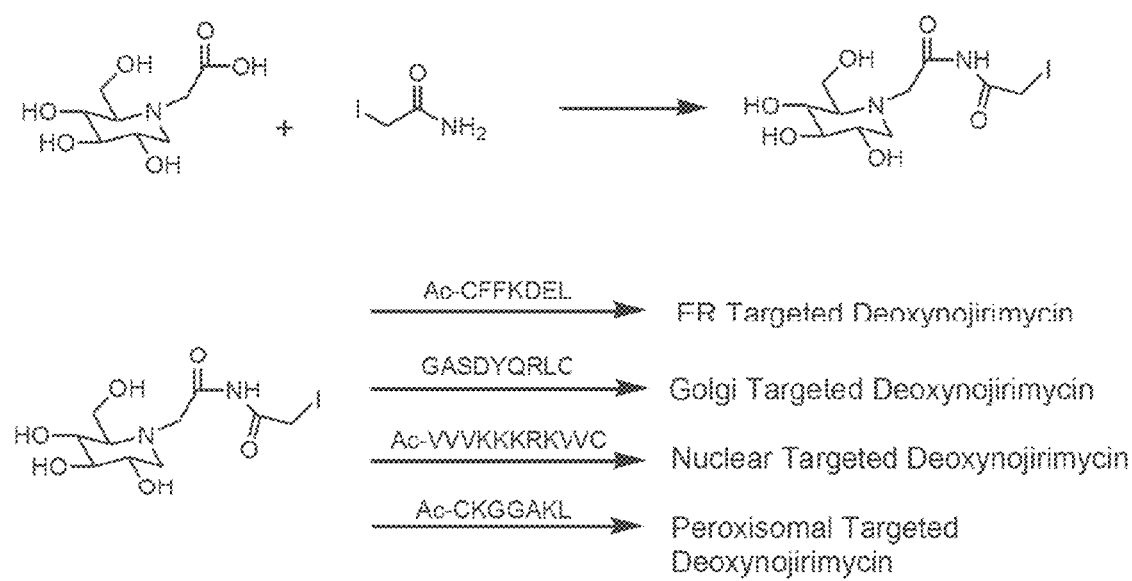
Figure 5. Synthesis of examples of ER targeted, Golgi targeted, nuclear targeted and peroxisomal targeted versions of Deoxynojirimycin.

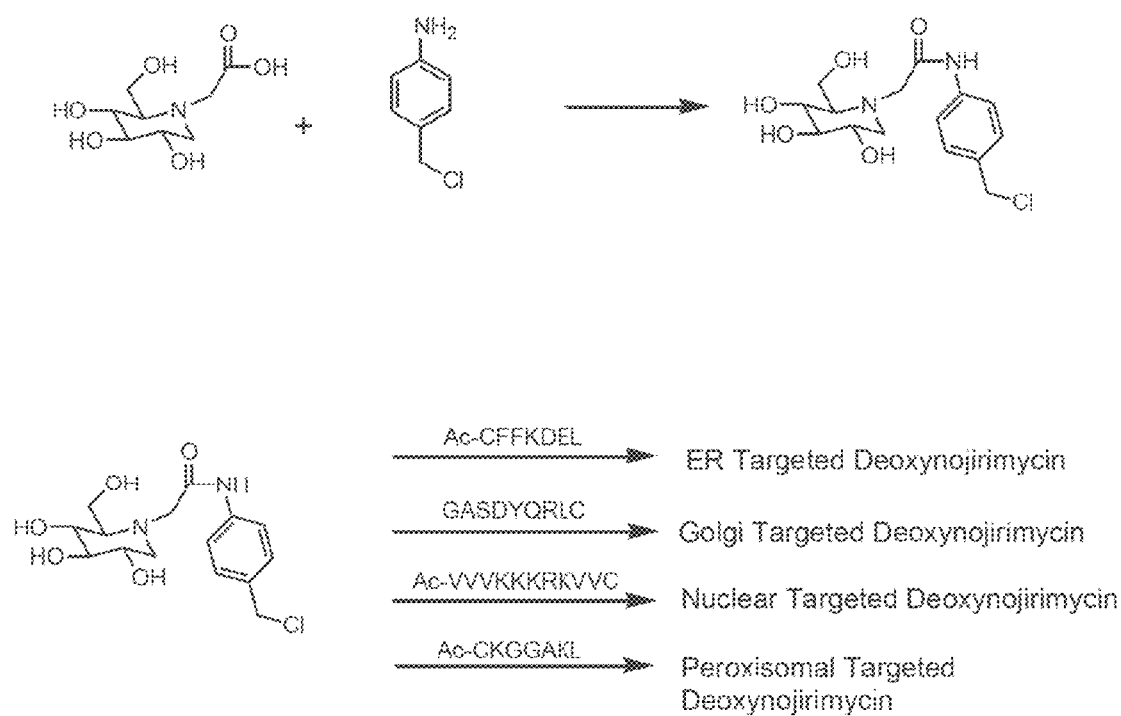
Figure 6. Synthesis of examples of ER targeted, Golgi targeted, nuclear targeted and peroxisomal targeted versions of Deoxynojirimycin.

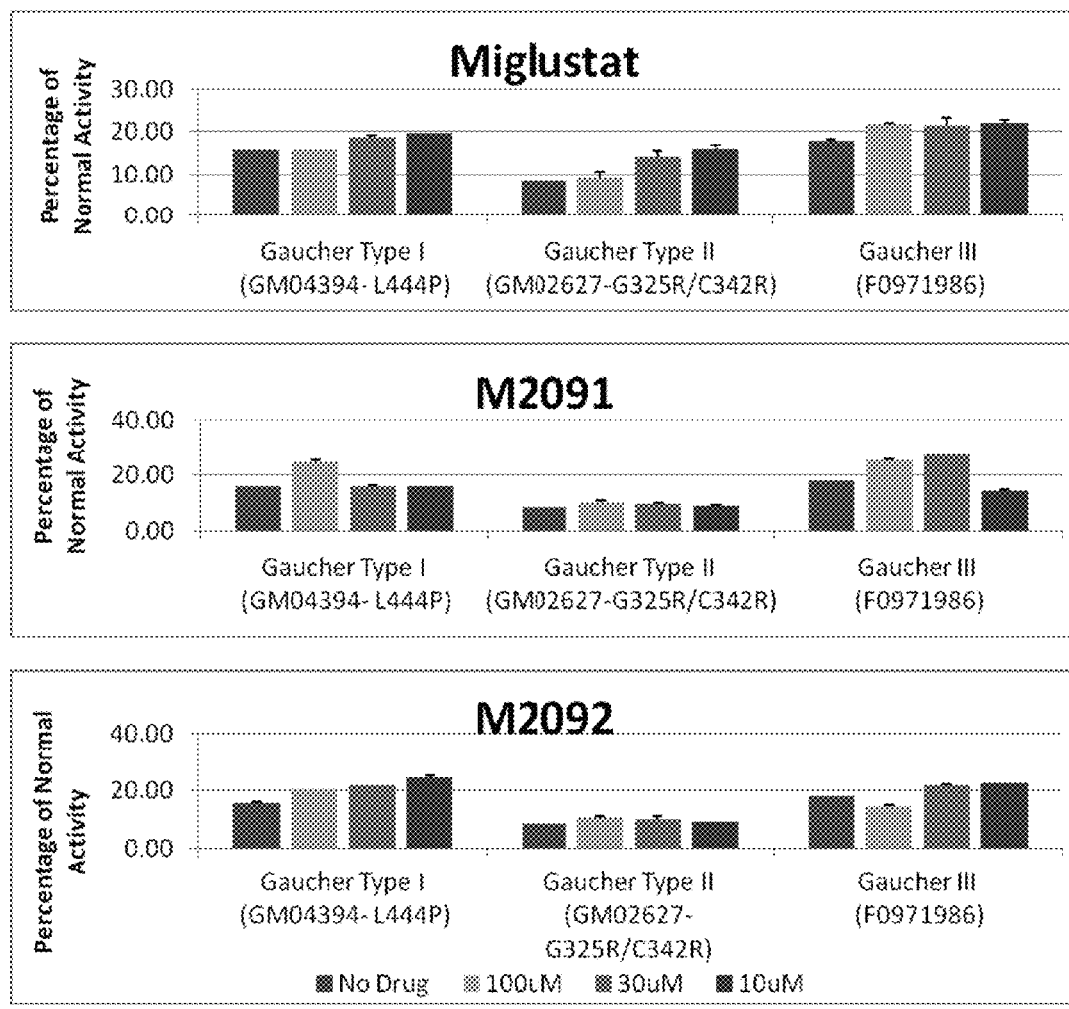
Figure 7. Analysis of enzyme levels by lysis assay in patient fibroblast cell lines upon application of targeted pharmacological chaperones.

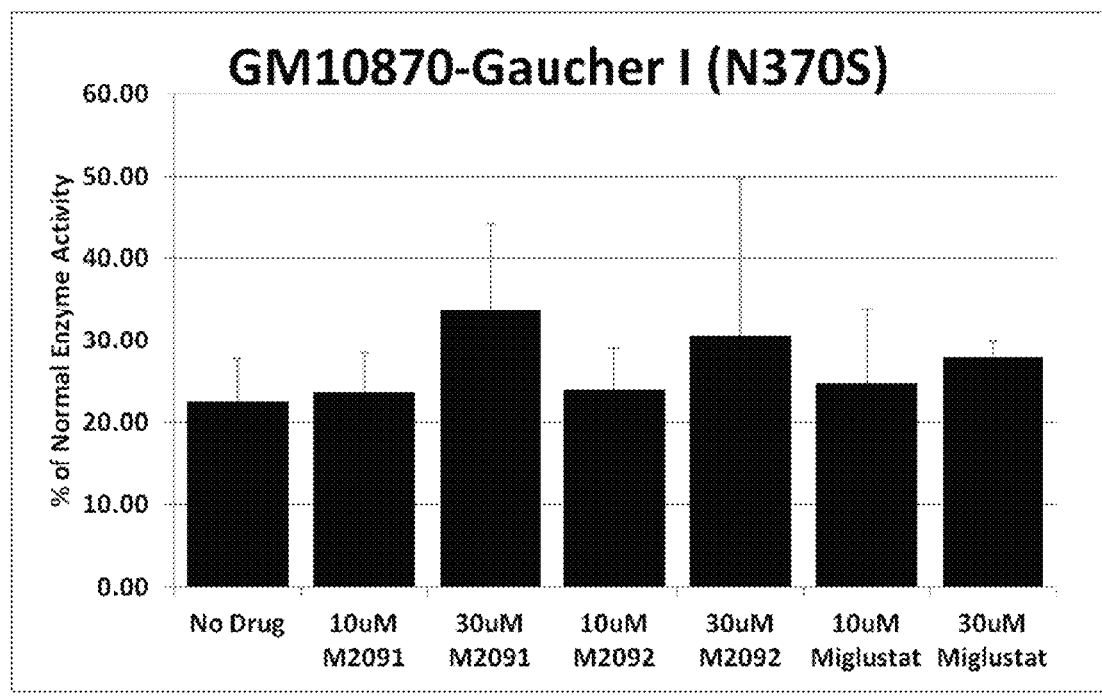
Figure 8. Analysis of increase in enzyme activity by TPCs in immortalized patient B-lymphocytes measured by flow cytometry.

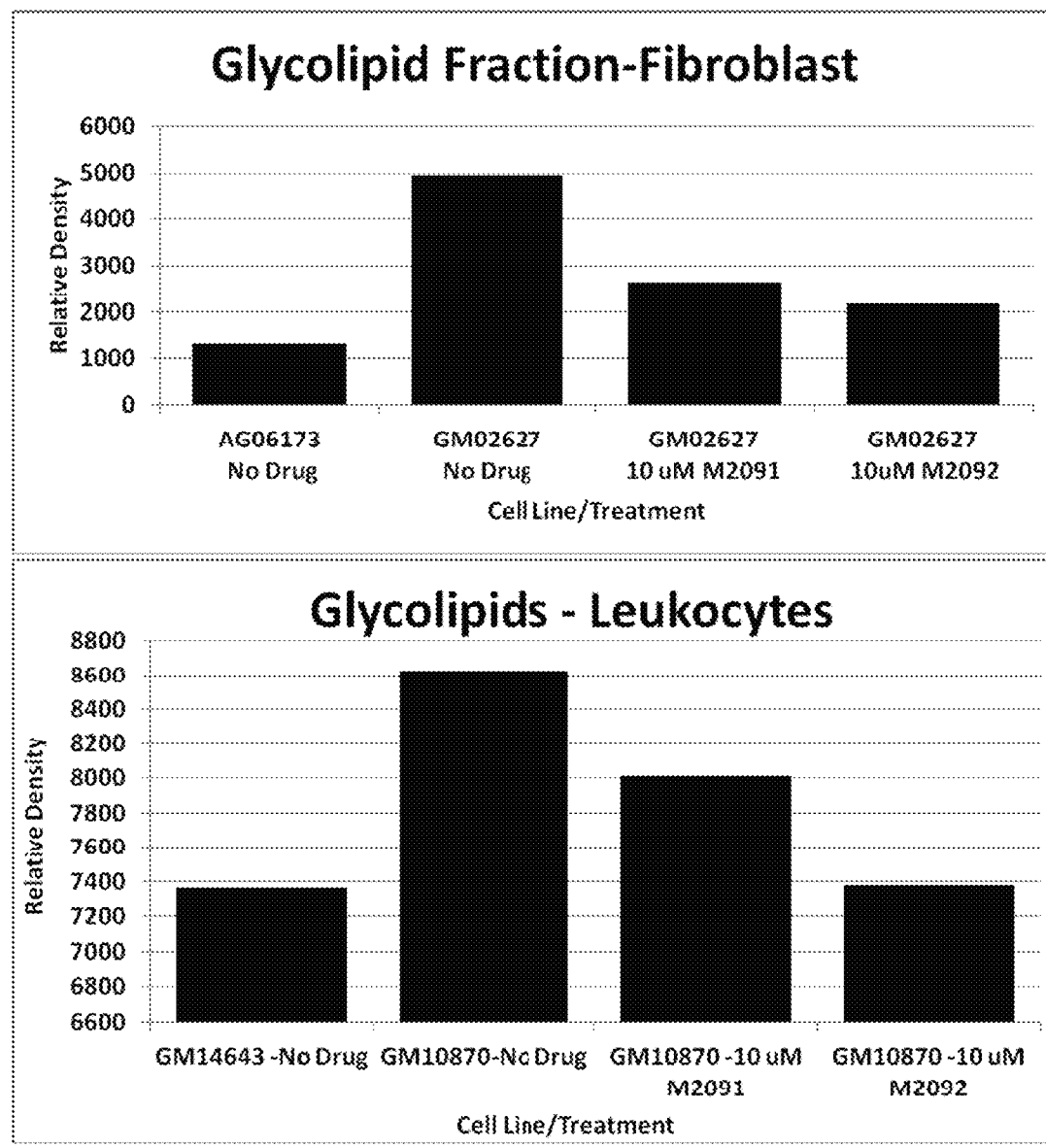
Figure 9. Analysis of Glycolipid content following TPC treatment.

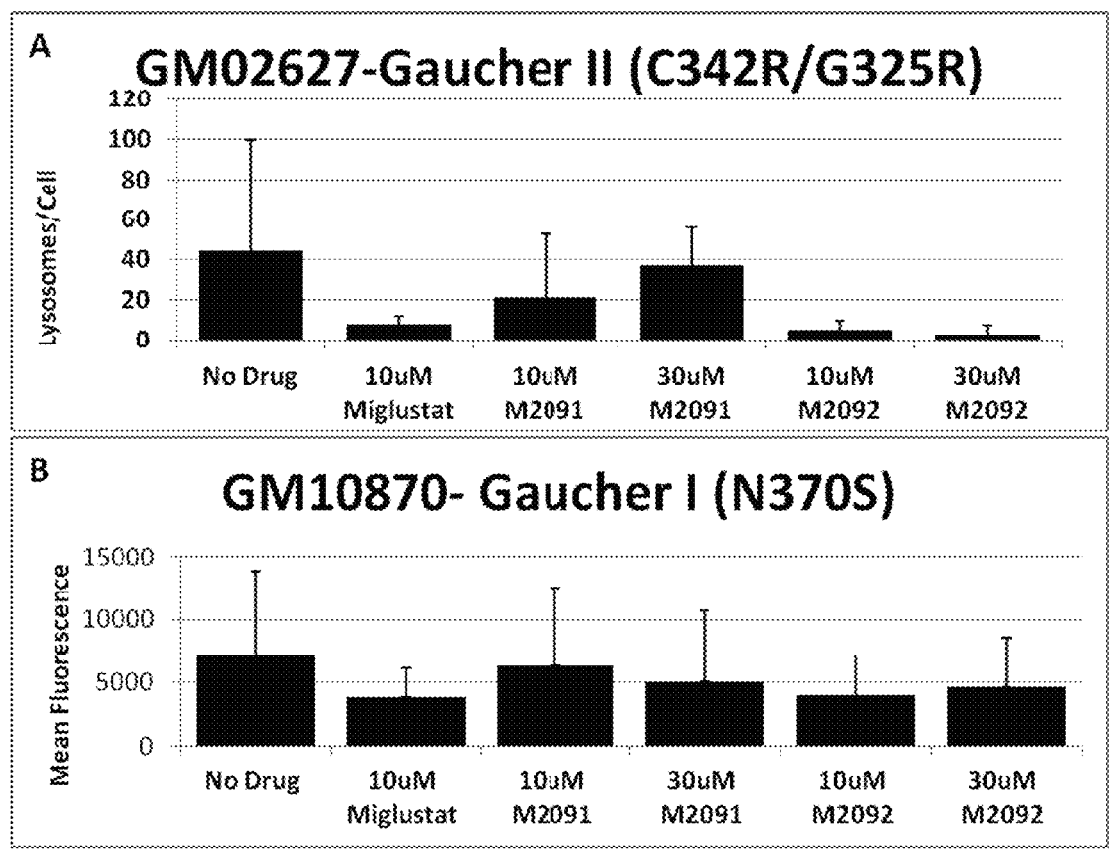
Figure 10. Measurement of lysosomal burden by Lysotracker™ Green staining following TPC treatment.

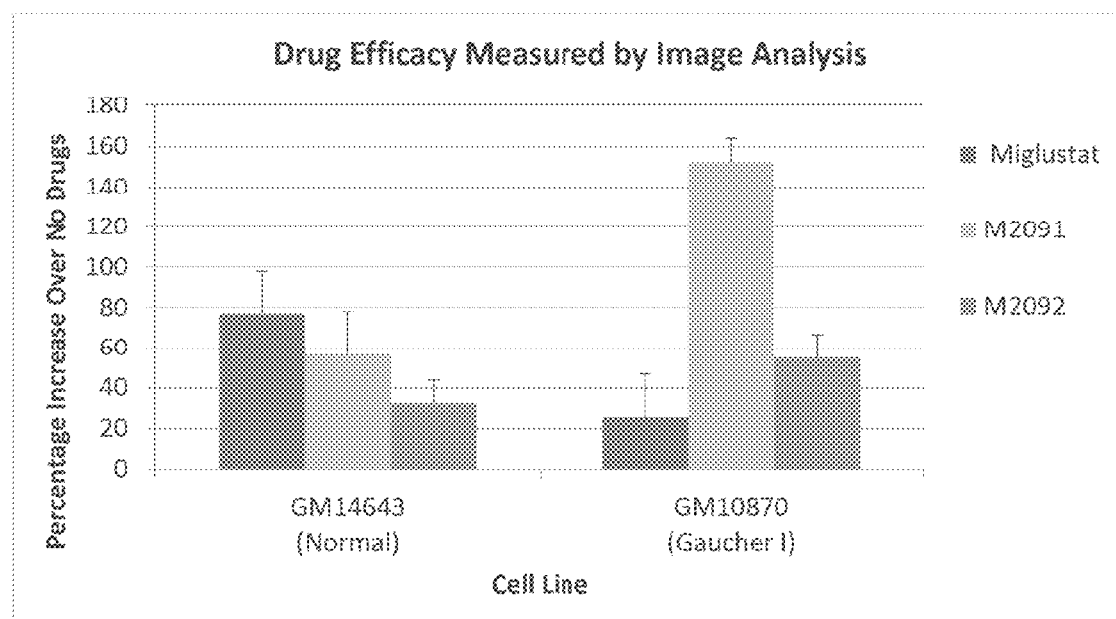
Figure 11. Measurement of increase in enzyme activity after TPC treatment by image analysis.

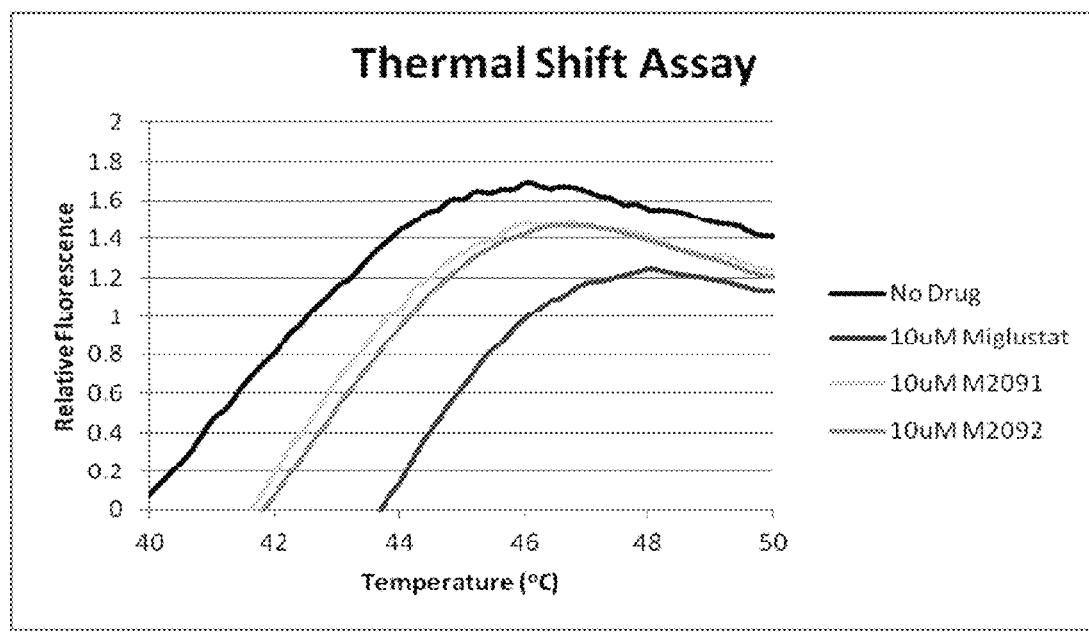
Figure 12. Assessment of binding and stabilizing capacity of TPCs by thermal shift assay.

TARGETED PHARMACOLOGICAL CHAPERONES

CROSS-REFERENCE TO RELATED APPLICATIONS

The present application is a divisional of U.S. application Ser. No. 14/689,267 which issued on Apr. 4, 2017 as U.S. Pat. No. 9,610,358 and claims priority in Provisional Application U.S. Ser. No. 61/995,671 filed Apr. 17, 2014 and Provisional Application U.S. Ser. No. 62/176,131 filed Feb. 9, 2015.

This invention was made with Government support under grant 5R44NS073225 awarded by the National Institutes of Health. The Government has certain rights in this invention.

REFERENCE TO SEQUENCE LISTING

The present invention includes a sequence listing submitted in Computer Readable Form (CRF) which is hereby incorporated by reference. The CRF includes a single file of 5 KB denoted "MGT-5_ST25.txt" recorded on Apr. 10, 2015.

FIELD OF THE INVENTION

The present invention relates to the preparation aid use of therapeutic compounds for the treatment of diseases at specific subcellular target areas such as specific cellular organelles. In particular, the therapeutic compounds of the invention are specific for modifying enzyme activity within targeted organelles or structures of cells and tissues. Subcellular organelles and structures that may be specifically targeted by compounds of the present invention include lysosomes, autophagasomes, the endoplasmic reticulum, the Golgi complex, peroxisomes, the nucleus, and the mitochondria. Accordingly, such therapeutic compounds may be used as treatments for diseases which cannot be treated by compounds that are too large to enter specific subcellular targets. Such diseases include those associated with protein deficiency disorders including lysosomal storage disorders, Parkinson's disease and cystic fibrosis.

BACKGROUND OF THE INVENTION

Acidic organelles are present in all cells and tissues of mammalian, plant, yeast and fungal cells, except red blood cells. Lysosomes are an example of an acidic cytoplasmic organelle that have been found to be involved in a variety of cellular processes including repair of the plasma membrane, defense against pathogens, cholesterol homeostasis, bone remodeling, metabolism, apoptosis and cell signaling. To date, more than 50 acidic hydrolytic enzymes have been identified that are involved in ordered lysosomal degradation of proteins, lipids, carbohydrates and nucleic acids. Functional deficiencies in these lysosomal enzymes, however, are indicative of a number of disease states.

As a group, these diseases are among the most prevalent genetic abnormalities of humans. Gaucher disease, Sandhoff disease, Krabbé disease, and Tay-Sachs syndrome comprise the majority of patients in this category and are categorized as sphingolipidoses in which excessive quantities of un-degraded fatty components of cell membranes accumulate due to mutations of specific catabolic enzymes that normally localize in the lysosomes to degrade such cellular components.

Without being bound by theory, it is thought that such genetic mutations may result in improper folding of these catabolic enzymes. Endoplasmic reticulum (ER) associated degradation serves as a "quality control" system for ensuring that only properly folded and assembled proteins are transported out of the ER for further maturation, while improperly folded proteins are retained for subsequent degradation (Hurtley S M, Helenius A (1989) Ann. Rev. Cell Biol. 5:277-307.). Accordingly, the disease state caused by such mutations may be a result of decreased enzyme stability, increased retention and degradation in the ER or impaired trafficking of the enzyme to the lysosome.

The therapeutic options for treating these diseases are relatively limited: in fact, there are currently no available therapies for many of these disorders. To date, therapeutic efforts have mainly focused on strategies for augmenting enzyme concentrations by providing large quantities of the enzyme (Enzyme Replacement Therapy, ERT) to compensate for the underlying defect (Grabowski, G A, Hopkin, R J (2003) Ann Rev. Human Genet. Genom. 4: 403). This type of therapy, however, has a number or drawbacks, including the inability of the administered protein to cross the blood-brain barrier where much of the neurological damage in these diseases can occur. Thus far, use of ERT has been largely unsuccessful in improving central nervous system manifestations for many of the lysosomal storage diseases, putatively due to difficulty in penetrating the blood-brain barrier.

Pharmacological chaperone therapy (PCT) has emerged as a possible new treatment option for diseases caused by improper protein folding or mis-trafficking. PCT relies on the ability of pharmacological chaperones (PCs) to bind to a mutant enzyme after it is made in the ER and promote a correctly folded conformation of the target mutant protein, thereby enabling it to meet the quality control standards in the ER and rescue it from degradation in the ER, and/or Golgi and restore trafficking to the trans-Golgi and lysosome.

Recent evidence has shown that accumulation of unprocessed compounds in cells results from low levels of functional enzymes, and not from low intrinsic catalytic enzyme activity of the low level of enzymes available. This indicates that the improperly folded enzymes retain sufficient functionality to remove or alleviate disease symptoms if they can simply avoid degradation by cellular quality control systems and thus supports the feasibility of PCT in treatment.

Although somewhat counterintuitive, enzyme competitive inhibitors can act as good pharmacological chaperones and increase the steady-state lysosomal levels of active enzymes through this rescuing mechanism. Once the inhibitor aids the enzyme in avoiding degradation in the ER, the inhibitor is eventually displaced from the active site, releasing the enzyme to conduct its intended catabolic activity in the lysosome.

Among the most common pharmacological chaperones developed to date are iminoalditols; imino-analogs of the sugar which the enzyme acts upon. Miglustat (OGT 918, N-butyldeoxynojirimycin) is one such competitive inhibitor that is used primarily to treat Type I Gaucher disease (GDI). Miglustat is an imino sugar, a synthetic analogue of D-glucose that contains a short-chain alkyl function on the imino nitrogen that promotes binding and bioavailability. It is one of the only small molecule pharmacological chaperones in clinical use. As a pharmacological chaperone, miglustat functions by helping promote correct folding of mutant enzymes and thereby bypass the degradation mechanisms located in the ER.

N-Alkyl iminoalditols, such as miglustat, or similar galactose, fucose, iduronate or mannose derivatives have also found use in combination with Enzyme Replacement Therapy (ERT) protocols. By administering the enzyme already coordinated with the inhibitor bound to the active site, intracellular levels of enzymes have been increased. To date, however, the activity of such iminoalditols for efficacy in treatment of the lysosomal storage disorders or allied diseases has been largely unsatisfactory. Without being bound by theory, such unsatisfactory results are likely due to the inability to concentrate sufficient amounts of miglustat in target organelles within the diseased cell.

Substrate reduction therapy (SRT) has also been developed as another alternative treatment option for these diseases. By inhibiting the initial biosynthesis of a precursor compound at an earlier metabolic step, it is postulated that the buildup of glycolipids or other biological compounds due to the defective enzyme will be abated. The therapeutic effect of substrate reduction therapy depends upon the presence of residual hydrolytic activity towards any accumulated substrates.

This approach has been used in the treatment of Gaucher disease through the inhibition of uridine diphosphate glucosylceramide transferase, the enzyme responsible for initial formation of the glucosyl compound that accumulates in Gaucher disease. One candidate for SRT is miglustat which is a known inhibitor of the enzyme glucosylceramide synthase that catalyzes the first step in the biosynthesis of glycosphingolipids (GSL), i.e., the formation of glucosylceramide (GlcCer). By reducing the formation of GlcCer, a decreased biosynthesis of more complex GSL is affected (Cox et al, (2000) "Novel oral treatment of Gaucher's disease with N-butyldeoxynojirimycin (OGT 918) to decrease substrate biosynthesis." Lancet 355:1481). To date this approach has also resulted in unsatisfactory results which are likely due to the inability to concentrate sufficient amounts of miglustat in target organelles within the disease cell.

In addition to the lysosomal storage disorders, a large and diverse number of diseases are now recognized as conformational diseases that are caused by adoption of non-native protein conformations, leading to retardation of proteins in the ER and ultimate degradation (Kuznetsov et al, N. Engl. J. Med. 1998; 339:1688-1695: Thomas et al, Trends Biochem. Sci. 1995; 20:456-459; Bychkova et al., FEBS Lett. 1995; 359:6-8; Brooks, FEBS Lett. 1997; 409:115-120).

Small molecule pharmacological chaperones have been shown to rescue expression of mutant proteins other than enzymes. For example, small synthetic compounds were found to stabilize the DNA binding domain of mutant forms of the tumor suppressor protein p53, thereby allowing the protein to maintain an active conformation (Foster et al., Science 1999; 286:2507-10). Synthesis of receptors has been shown to be rescued by small molecule receptor antagonists and ligands (Morello et ai. J. Clin. Invest. 2000; 105:887-95; Petaja-Repo et al., EMBO J. 2002; 21:1628-37.). Even pharmacological rescue of membrane channel proteins and other plasma membrane transporters has been demonstrated using channel-blocking drugs or substrates (Rajamani et al., Circulation 2002; 105:2830-5; Zhou et al., J. Biol. Chem. 1999; 274:31123-26; Loo et al., J. Biol. Chem 1997; 272: 709-12). Also, pharmacological chaperones have also been identified that can act to rescue the mutant transmembrane regulator protein associated with cystic fibrosis, the $\Delta^{F508}$-CFTR protein, from ER degradation.

Pharmacological chaperones have also been shown to stabilize wild-type proteins, resulting in their enhanced production and stability. As one example, it has been demonstrated that 1-deoxygalactonojirimycin is able to increase the amount and activity of α-Gal A in COS-7 cells transfected with a vector coding the α-Gal A sequence. The Pharmacological chaperone is able to rescue the overexpressed enzyme, which is otherwise retarded in the ER quality control system, because overexpression and over production of the enzyme in the COS-7 cells exceeds the capacity of the system and leads to aggregation and degradation (U.S. patent application Ser. No. 10/377,179, filed Feb. 28, 2003).

In all cases the efficacy of pharmacological chaperone treatments is limited by the ability to deliver such molecules to the appropriate target organelle in sufficient quantities to produce a clinically useful result. Accordingly there exists a long-felt need in the art to create a system for the targeted delivery of such compounds.

Peptide motifs that can be used to target proteins or even small molecules to various locations within cells are known in the art. For example, the nuclear targeting sequence from the SV40 large T antigen PKKKRKV (SEQ ID NO: 1) has been used to localize exogenously delivered macromolecular conjugates (Branden L J, Christensson B, Smith C I. (2001) Gene Ther. 8(1):84-87.) to live cells as well as recombinant proteins expressed after plasmid or viral DNA transfection/transduction (Dingwall C, Laskey R A. (1991) Trends Biochem. Sci. 16(12):478-481.).

Peptide localization motifs have also been described for organelles other than the nucleus. For example, the four amino acid sequence KDEL (SEQ ID NO:2) at the amino terminus of a protein is a well established ER-retention sequence (Muaro S, Pelham H R. (1987) Cell. 48(5):899-907.), while the carboxy-terminal sequence of amino acids containing the amino acid sequence SKL has been identified for peroxisomal targeting (Gould S G, Keller G A, Subramani S. (1987) J Cell Biol 105(6 Pt 2); 2923-2931)

These and other targeting sequences have also been used for fluorescent labeling of specific organelles in live cells as an orthogonal method to cell staining by conjugation to small molecule organic dyes (Eward H. W. Pap, Tobias B. Dansen Ruben van Summeren & Karel W. A. Wirtz (2001) Experimental Cell Research 265: 288-293). These peptide sequences are known to be actively transported into living cells by the method of retrograde transport (Johannes L, Tenza D, Antony C, Goud B, (19971 J. Biol. Chem. 272: 19554-19561; Majoul I V. Bastiaens P I, Siling H D (1996) J. Cell Biol. 133(4):777-789.)

While such targeting peptides have been used as research tools for localizing compounds of interest in specific organelles their potential for targeted delivery of therapeutic agents within living cells or tissues remains unexplored. Such targeting has the potential to greatly improve the efficacy of known small molecule pharmacological chaperone compounds as well as other drugs known to act in specific organelles within living cells.

SUMMARY OF THE INVENTION

It is the object of the present invention to provide methods and compositions for the treatment or prevention of diseases including the lysosomal storage disorders. In particular the invention provides methods for therapeutic treatment and describes the synthesis of materials for use as therapeutic agents in modifying enzyme activity, levels in cells or tissues, whether present in vi or from isolated cellular preparations. These methods involve using targeted compounds that are transported into cells and tissues and subsequently sequestered to individual organelles within the cells for improved activity. The method comprises: administration of an effective amount of the targeted pharmacological chaperone (TPC) or a pharmacologically acceptable salt thereof, of the present invention, wherein the TPC acts to increase cellular levels or trafficking of an active protein within the cell, or increase the secretion of an active protein from the cell.

The targeted pharmacological chaperone (TPC) compounds of this invention are designed to augment intracellular protein activity by promoting trafficking of mutant or incorrectly folded proteins through the Endoplasmic Reticulum (ER) and the Golgi Apparatus of intact cells and thereby permit passage into specific organelles including lysosomes, phagosomes, autophagosomes, secretory vesicles, mitochondria, the nucleus or even back to the ER, where they are normally active in the cell.

The TPCs can therefore be used for treatment of diseases that involve incorrect protein folding, storage and/or degradation. The instant compounds and methods are also useful as potential therapeutics for a wide range of diseases associated with defective protein expression as well as for use in treatment of infective diseases, either from bacterial or viral origin, that are known to sequester in and affect target organelles inside the cell.

In addition, the instant compounds and methods are also useful for investigating intracellular metabolism, investigating the biogenesis of organelles, investigating the development of autophagic vacuoles and lysosomes, fusion of phagosomes with acidic lysosomes, investigating the transport of proteins within the cell, as well as improving the clearance or activation of secondary therapeutics within the cell. In particular the instant invention is useful in the treatment of neurological diseases including, but not limited to lysosomal storage diseases, neurological diseases including ALS, epilepsy, Parkinson's disease, viral diseases, Cholera, Chlamydia or malarial infection. The current invention is also useful for treatment of or use in non-mammalian cell systems that exhibit defective protein expression, degradation or protein deficiencies including plant, yeast and bacterial species.

BRIEF DESCRIPTION OF THE DRAWINGS

FIG. 1. Synthesis of examples of ER targeted Deoxynojirimycin, ER-targeted Deoxygalactonojirimycin. ER-targeted Deoxygalactonojirimycin, ER-targeted Alkyl Glucosamine, and ER-targeted 1-thio-deoxyglucose.

FIG. 2. Synthesis of examples of ER-targeted. Golgi-targeted, nuclear-targeted and peroxisomal-targeted derivatives of N-butyldeoxynojirimycin, Deoxygalactonojirimycin N-butyldeoxygalactonojirimycin, N-butyldeoxymannonojirimycin and N-butyl-2-deoxy-2-N-acetylnojirimycin.

FIG. 3. Synthesis of representative ER-targeted, Golgi-targeted, nuclear-targeted and peroxisomal-targeted versions of 2-[4-(5-carboxypentyl)phenyl]ethyl-1-deoxy-1-thio-β-D-glucopyranoside by direct peptide coupling methods.

FIG. 4. Synthesis of representative ER targeted, Golgi targeted, nuclear targeted and peroxisomal-targeted analogs of N-butyldeoxynojirimycin by a direct peptide coupling method.

FIG. 5. Synthesis of representative ER-targeted, Golgi-targeted, nuclear-targeted and peroxisomal-targeted derivatives of N-butyldeoxynojirimycin.

FIG. 6. Synthesis of representative ER-targeted, Golgi-targeted, nuclear-targeted and peroxisome-targeted versions of N-butyldeoxynojirimycin.

FIG. 7. Analysis of enzyme levels by lysis assay in patient fibroblast cell lines upon application of targeted pharmacological chaperones.

FIG. 8. Analysis of increase in enzyme activity by TPCs in immortalized patient B-lymphocytes measured by flow cytometry.

FIG. 9. Analysis of Glycolipid content following TPC treatment.

FIG. 10. Measurement of lysosomal burden by Lysotracker™ Green staining following TPC treatment.

FIG. 11. Measurement of increase in enzyme activity after TPC treatment by image analysis.

FIG. 12. Assessment of binding and stabilizing capacity of TPCs by thermal shift assay.

DESCRIPTION OF THE PREFERRED EMBODIMENTS

As used herein the following terms shall have the definitions set forth below.

As used herein the term "treating" means to ameliorate one or more symptoms associated with the referenced disorder.

As used herein, the term "preventing" means to impede or delay the onset of one or more symptoms associated with the referenced disorder.

As used herein the phrase "an effective amount" means an amount effective to prevent and/or treat a patient at risk for developing or diagnosed with the referenced disorder, and thus producing the desired therapeutic effect.

As used herein the term "patient" refers to a mammal (e.g., a human) at risk for developing or diagnosed with the referenced disorder.

As used herein the phrases "lysosomal storage disorder" and "lysosomal storage disease" refer to any of a group of diseases resulting from abnormal metabolism resulting in accumulation of a substrate in the lysosome.

As used herein, the phrase "degenerative disorder of the central nervous system" means any disorder associated with the premature degeneration of any component of the central nervous system, such as neurons, myelin sheaths or axons. Such disorders include but are not limited to multi-infarct dementia, Huntington's disease, Pick's disease, amyotrophic lateral sclerosis, Creutzfeldt-Jakob's disease, frontal-lobe degeneration, corticobasal degeneration, progressive supranuclear palsy, Parkinson's disease, dementia with Lewy bodies, multiple system atrophy or Alzheimer's disease.

The present invention utilizes novel compounds that act as targeted pharmacological chaperones to augment the levels of enzymes deficient in diseased cells and tissues, in vivo as well as in vitro. These new therapeutics selectively accumulate in cellular organelles or compartments and can be used to moderate the enzyme degradation pathways in the lysosomes, ER and Golgi which are responsible for biosynthesis, degradation and recycling of cellular components. As such the therapeutics of the present invention are useful for the treatment of diseases in which specific protein defects cause reduced protein activity in lysosonmes or other organelles within live cells.

The targeted pharmacological chaperones of the present invention have the general formula:

T(R)-LINK-DRUG(R)

Where T represents a Targeting group that is a peptide or peptide analog that partitions the pharmacological chaperone for specific import to or retention in particular organelles within the cell, DRUG represents a small molecule compound that can bind to a defective protein and influence its conformation, L represents an optional linking group that is used to conjugate the Targeting Group to the DRUG, and R represents a substituent or substituents to provide for improved transport of the pharmacological chaperone into the cell, where R can be removed by an endogenous enzyme activity within the cell, thus allowing the targeted pharmacological chaperone to interact with a defective protein in the cell.

In a particular embodiment, the targeted pharmacological chaperones of the present invention have the general formula:

(R')T-LINK-DRUG(R)

In a preferred embodiment, the optional LINK portion of LINK-T is a covalent linkage, serving to attach a targeting peptide, T, to the DRUG. Any suitable covalent linkage that does not interfere with the ability of the DRUG, a pharmacological chaperone, to selectively bind to a defective protein in the cell is an acceptable covalent linkage for the purposes of the present invention. In one embodiment, LINK is a single covalent bond. Preferred LINK groups have 1-20 non-hydrogen atoms selected from the group consisting of C, N, O and S. Such LINK groups are composed of any combination of chemical bonds, including ether, thioether, succinylthioether, benzylthioether, amine, ester, carboxamide, sulfonamide, hydrazide bonds, and single, double, triple carbon-carbon bonds, and aromatic or heteroaromatic bonds.

Preferred LINK groups are composed of any combination of single carbon-carbon bonds and carbon-sulfur bonds. Selected specific examples of LINK optionally include methylenes, oligomethylenes, phenylenes, thienyls, carboxanides, and sulfonamides. In one embodiment of the invention, LINK contains 1-6 carbon atoms. In an additional embodiment of the invention, LINK has the formula —$(CH_2)_a(N(COCH_2)_z$—, where a has any value from 0-5 and z is 1 or 2. In an additional embodiment of the Invention. LINK has the formula —$(CH_2)_a(N(COPhCH_2)$—, where a has any value from 0-5.

In a particular embodiment of the invention, the T and DRUG groups are further modified with a substituent or substituents (R and R') that improve membrane permeability of the substrate through cellular membranes. The substituent or substituents R and R', which may be the same or different, are selected from the group including an unsubstituted carboxylic acid ester and an alkyloxy substituted carboxylic acid ester. The substituents (R or R') of the present invention that lipophilic groups that are covalently attached to T or DRUG facilitate membrane permeability and live cell entry. Once inside the cells, these lipophilic groups are hydrolyzed by endogenous cell processes resulting in release of the underivatized T-LINK-DRUG molecules that are then well retained in living cells.

In a particular embodiment, lipophilic substituents R and R' are acetoxymethyl (AM) ester or acetate esters. Once inside the cells the groups are cleaved by nonspecific esterases resulting in active molecules.

The targeting group T has the general formula as presented below in Table 1.

TABLE 1

Targeting sequence peptides and known intracellular localization

| Peptide (localizaiion) | Amino acid sequence | Net change |
|---|---|---|
| PTS1 (peroxisomal) | Ac-CKGG<u>AKL</u> (SEQ ID NO: 3) | +1 |
| NLS (nuclear) | Ac-VVV<u>KKKRK</u>VVC (SEQ ID NO: 4) | +4 |
| KDEL (ER) | Ac-CFF<u>KDEL</u> (SEQ ID NO: 5) | -2 |
| TGN (trans-Golgi network) | GA<u>SDYQRL</u>C (SEQ ID NO: 6) | 0 |

As is known in the art, the targeting group peptide can also be modified to improve or reduce binding to the receptor in the membrane by modifications of the peptide sequence, by using D-amino acids in the existing sequences or by using peptide analogs such as peptidomimetics. Some of these modifications, listed below in Table 2, can be used to improve targeting or bioavailability of the targeted pharmacological chaperones.

TABLE 2

Additonal peptide sequences for target group applications

| Peptide (localization) | Amino acid sennence | SEQ ID NO |
|---|---|---|
| ER | CAHHAEL | 7 |
| ER | CARHAEL | 8 |
| ER | CPLHNEL | 9 |
| ER | CERHTEL | 10 |
| ER | CTEHIEL | 11 |
| ER | CTEHVEL | 12 |
| trans-Golgi | SDpYQRLC | 13 |
| trans-Golgi | ADYQRLC | 14 |
| trans-Golgi | SGYQRLC | 15 |
| trans-Golgi | AAYQRLC | 16 |
| trans-Golgi | SDYERLC | 17 |
| trans-Golgi | SDYQRVC | 18 |
| nuclear | AcVVVKKRRRVVC | 19 |
| nuclear | AcVVVKKKRKVVC | 20 |
| nuclear | AcVVVKKRKKVVC | 21 |

TABLE 2-continued

Additonal peptide sequences for target group applications

| Peptide (localization) | Amino acid sennence | SEQ ID NO |
|---|---|---|
| peroxisomal | AcCKGGYQSKL | 22 |
| peroxisomal | AcCKGGYQSEL | 23 |

In a particular embodiment, targeting group T is a peptide selected from the group consisting of -AKL-, -KKKRK- (SEQ ID NO:24), -KDEL- (SEQ ID NO:2) and -SCYQRL- (SEQ ID NO:25).

In one embodiment of the present invention DRUG is a pharmacological chaperone which selectively binds to a defective protein in the cell. In a preferred embodiment, DRUG is selected from the group including iminoalditols, aminosugars, thiophenylglycosides or other known glycosidase, sulfatase, glycosyl transferase, phosphatase or peptidase inhibitors known to affect protein folding and export from the endoplasmic reticulum or Golgi apparatus in living cells or tissues by acting as chemical chaperones.

A variety of iminosugars are known to be active as agents that can modify the underlying metabolic dysfunction by either inhibiting biosynthesis of the accumulating substrates (SRT) or by augmenting residual enzymatic activity by effecting or promoting proper folding or trafficking of mutant enzyme in the cell. Among the iminosugars utilized in this regard are those described by Butters (2007) and in, Compain, P. Martin O. R. (eds.) ISBN:978-0-470-03391-3, J. Wiley and Sons, pp. 249-268 and the Table in Chapter 14.8 thereof). In addition, several other pharmacologically active agents, active in this same regard, including thioglycosides and alkylglycosylamines are included in the present invention as effective DRUG compounds.

Among the most common pharmacological chaperones developed to date are iminoalditols; imino-analogs of the sugar which the enzyme acts upon. In a particular embodiment of the present invention the DRUG may be a Miglustat (OGT 918, N-butyl-deoxynojirimycin), an N-alkyl-deoxymannonojirimycin, an N-alkylgalactonojirimycin, an N-alkyl-2-deoxy-2-N-acetylnojirimycin, a ThioGal, an alkyl Glucosamine or a thioglycoside. In another embodiment of the invention DRUG may be D-G lucosamine N-butylmaleimide ("4-maleimido-GluN"), 1-deoxygalactonojirimycin N-butylmaleimide, ("4-maleimido-Deoxygalactonojirimycin"), 1-deoxymannonojirimycin N-butylmaleimide ("4-maleimido-mimanstat"), 1-deoxynojirimycin N-ethylmaleimide, 1-deoxynojirimycin N-butylmaleimide ("4-maleimido-miglustat"), or p-carboxyphenethyl-1-thio-1-deoxy-glucose.

Methods of conjugating targeting peptides to other molecules including the N-alkyl iminoalditols are known in the art. The present invention describes additional methods of conjugating targeting peptides to the N-alkyl iminoalditols, including the use of maleimides, chloromethylbenzyl, iodoacetamides and direct coupling via a peptide linkage.

The linkage arm between the N-alkyl iminoalditols and the peptides can also be modified to improve biological activity, and several analogs with different alkyl lengths are described. Other linking arms are known in the art and can be substituted for these alkyl linkages. Any suitable covalent linkage that does not interfere with the ability of the iminoalditol to interact with the enzyme target and also not perturb selectively accumulation of the conjugate in specific organelles is an acceptable covalent linkage for the purposes of the present invention. In one embodiment, LINK is a single covalent bond. Preferred LINK groups have 1-20 nonhydrogen atoms selected from the group consisting of C, N, O and S. Such LINK groups are composed of any combination of chemical bonds, including ether, thioether, amine, ester, carboxamide, sulfonamide, hydrazide bonds, and single, double, triple carbon-carbon bonds, and aromatic or heteroaromatic bonds. Preferred LINK groups are composed of any combination of single carbon-carbon bonds and carboxamide bonds. Selected specific examples of LINK optionally include methylenes, oligomethylenes, phenylenes, thienyls, carboxamides, and sulfonamides. In one embodiment of the invention, LINK contains 1-6 carbon atoms. In an additional embodiment of the invention, LINK has the formula —$(CH_2)_a(CONH(CH_2)_b)_z$—Z, where a has any value from 0-5, b has any value from 0-5, z is 0 or 1 and Z is a reactive group chosen from the group maleimide, benzylchloromethyl, iodoacetamide, carboxy, N-hydroxysuccinimide, N-hydroxysulfosuccinimide or other reactive linkers as described in Peter J. H. Scott, J. Wiley and Sons, (2009).

In a preferred embodiment of the invention, LINK has the formula —$(CH_2)_a$(maleimide) prior to conjugation;

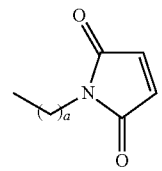

where a has any value from 0-5, and the resulting DRUG-LINK is reactive with peptides containing a thiol moiety.

Selected specific embodiments of targeted pharmacological chaperones useful for the treatment of neurological diseases associated with improper folding mechanisms in the ER, Golgi organelles and lysosomes are described in the Examples and in the FIGS. 1 through 6.

The targeted pharmacological chaperones of the present invention are readily prepared using the methods described herein. Specific methods for preparing the covalent linkage groups, LINK, and Targeting Group T are demonstrated in the Examples.

Specific embodiments of targeted pharmacological chaperones of the present invention include:

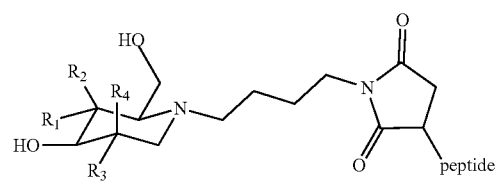

where R1, R2, R3 and R4 are independently selected from the group consisting of H and OH, and where peptide is selected from the group consisting of Ac-CKGGAKL, Ac-VVVKKKRKVVC, Ac-CFFKDEL, and GASDYQRLC;

11

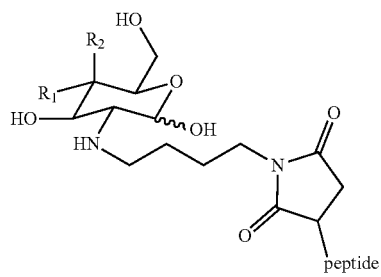

where R1 and R2 are independently selected from the group consisting of H and OH, and where peptide is selected from the group consisting of AcCKGGAKL, Ac-VVVKKKRKVVC, Ac-CFFKDEL, and GASDYQRLC; and

12

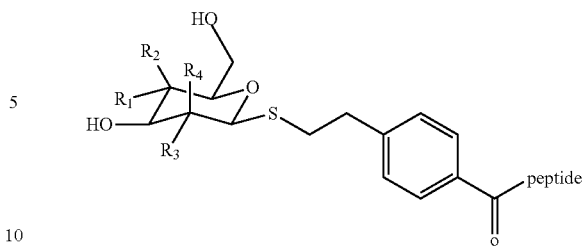

where R1 and R2 are independently selected from the group consisting of H and OH, and where peptide is selected from the group consisting of CKGGAKL, VVVKKKRKVVC, CFFKDEL, and GASDYQRLC.

Additional targeted pharmacological chaperones of the present invention include:

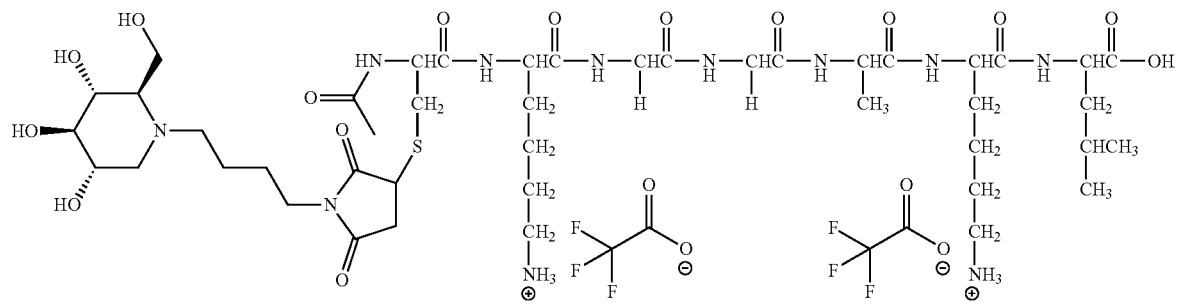

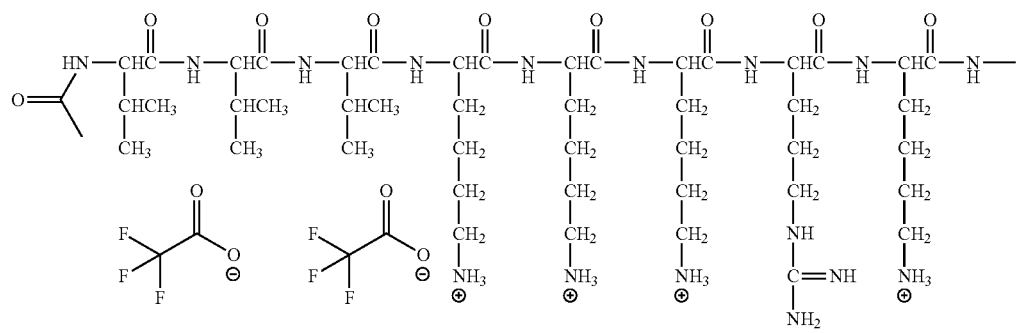

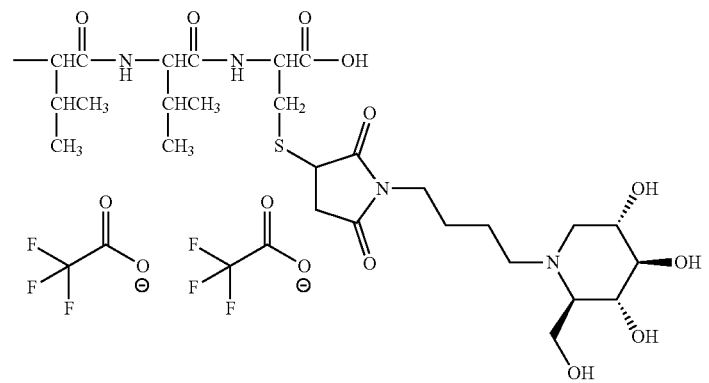

-continued
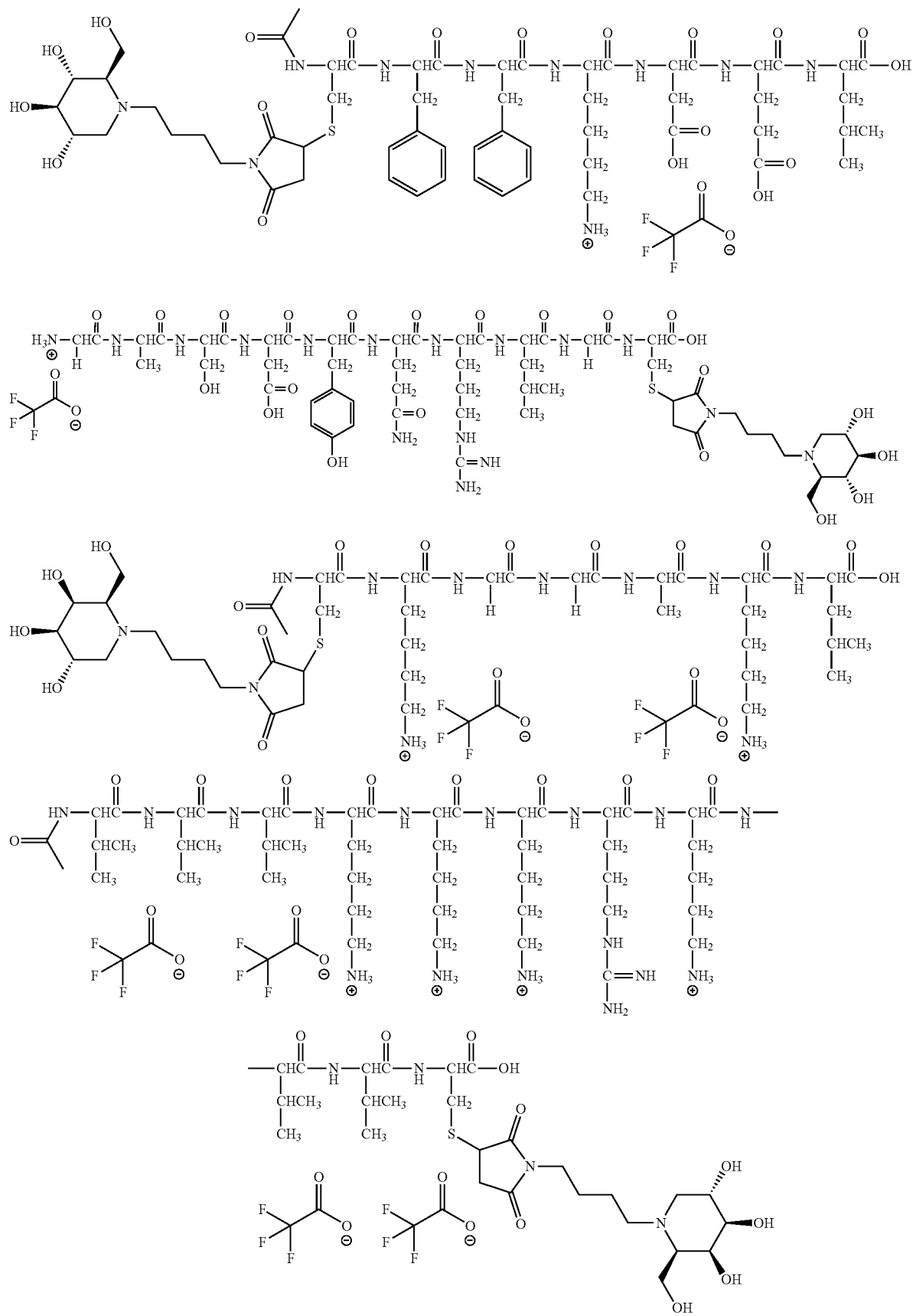

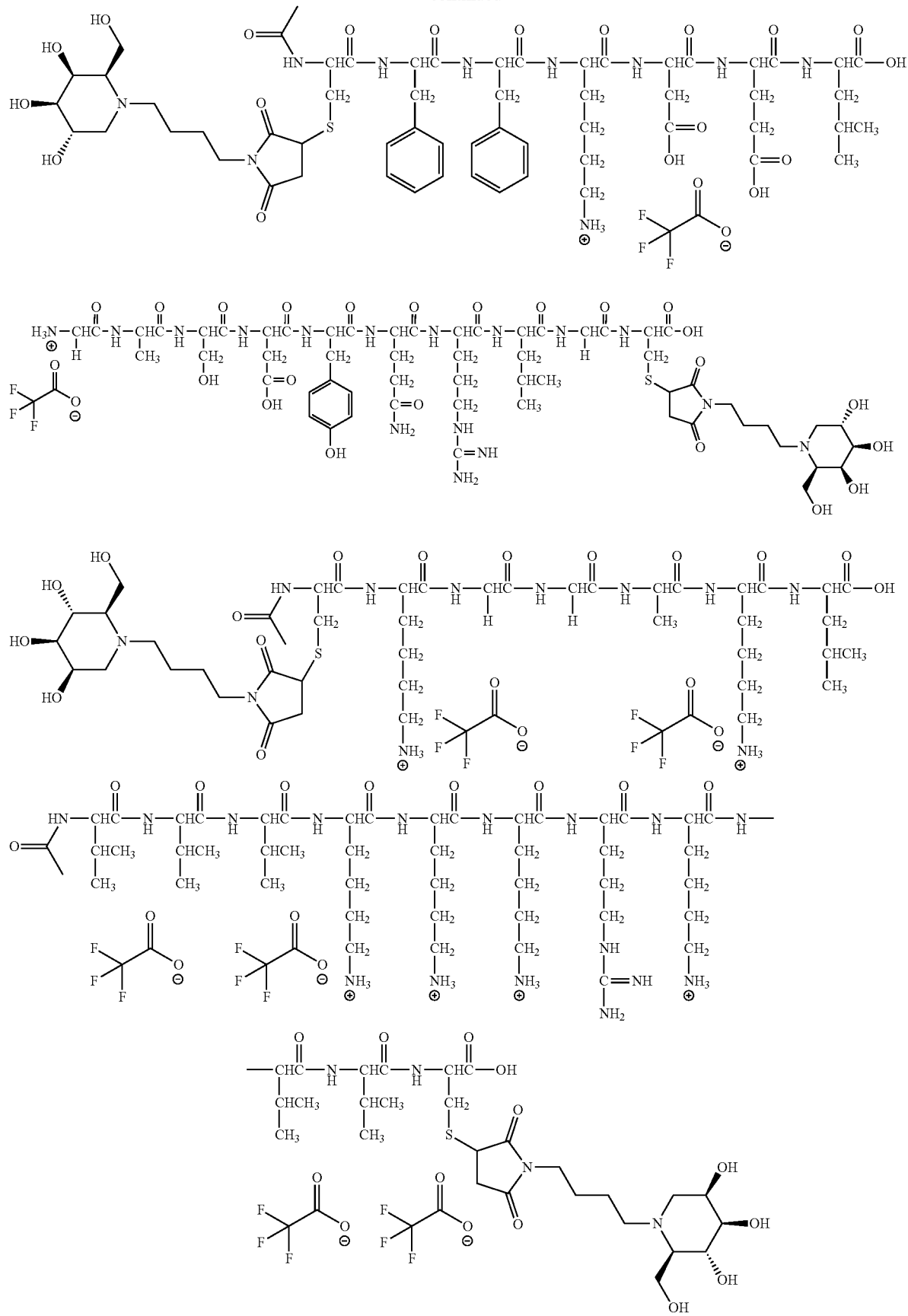

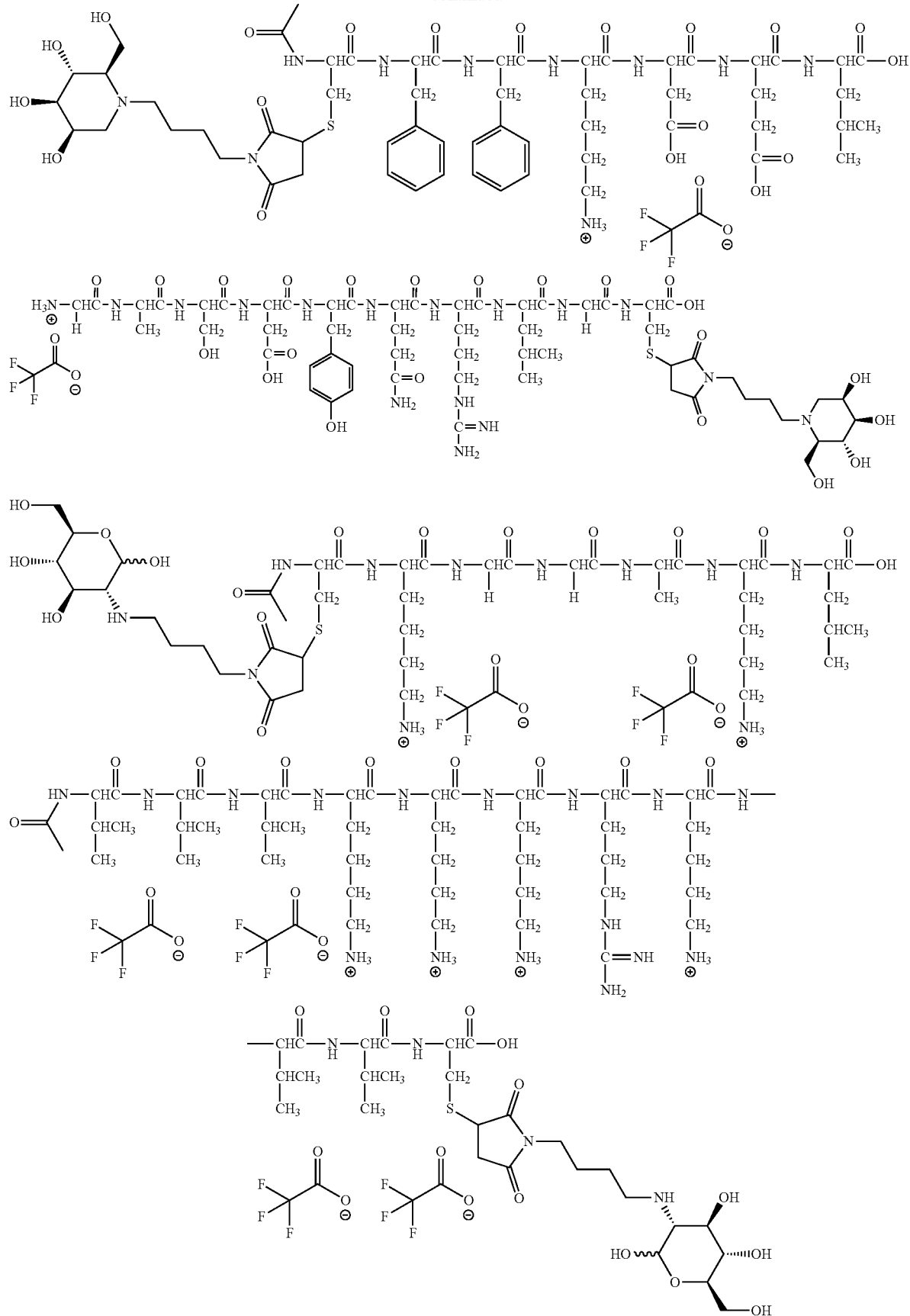
-continued

-continued
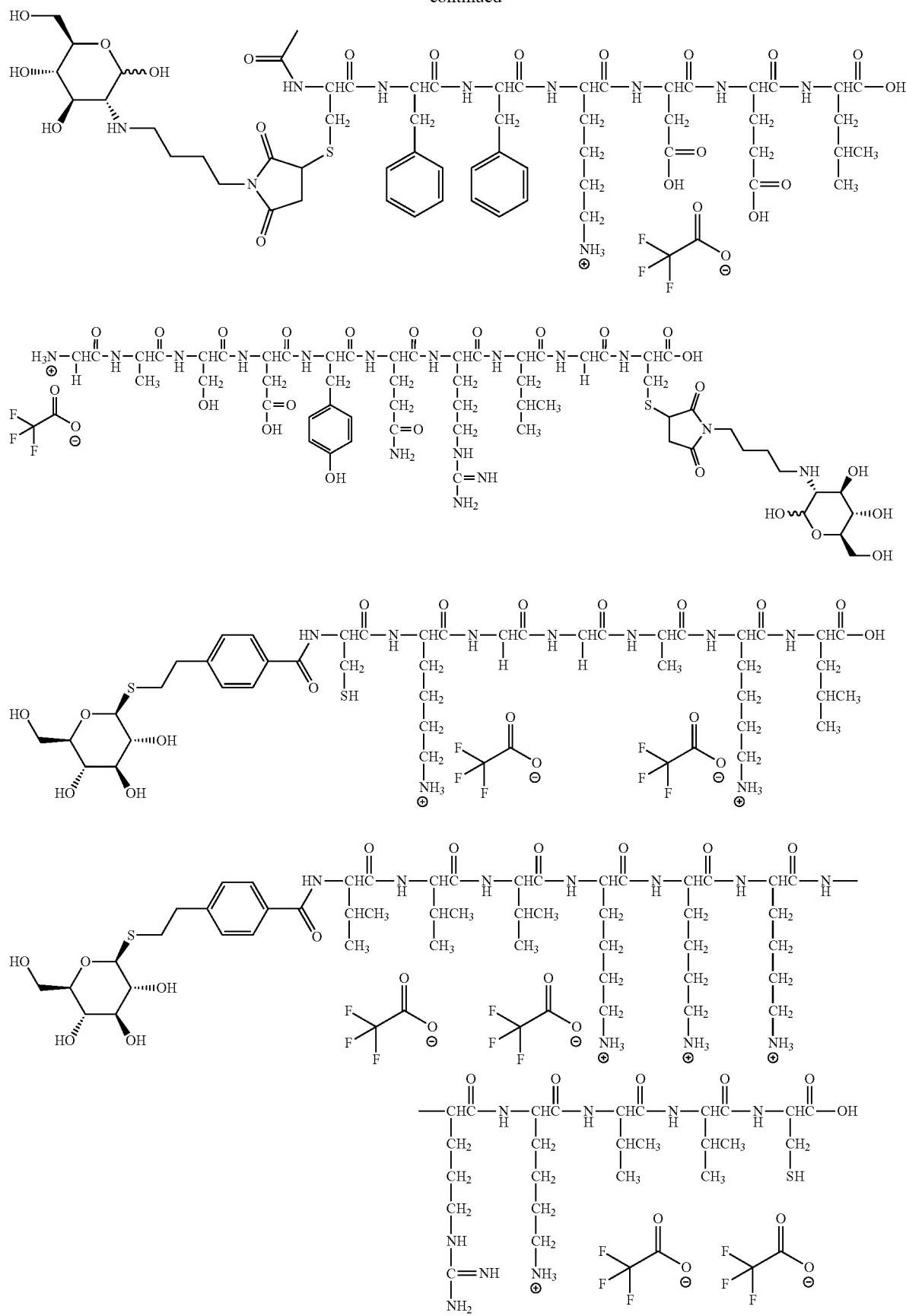

21
22
-continued
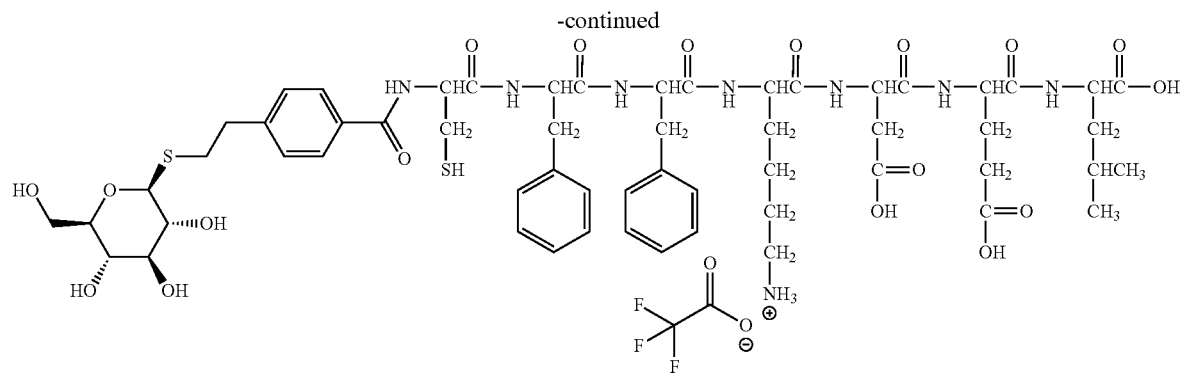
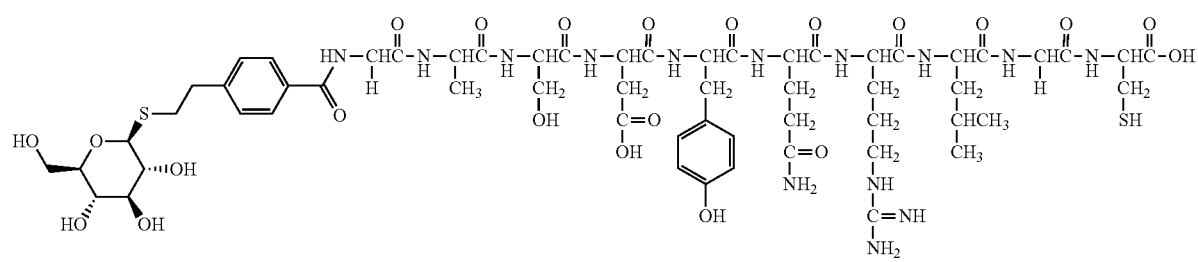
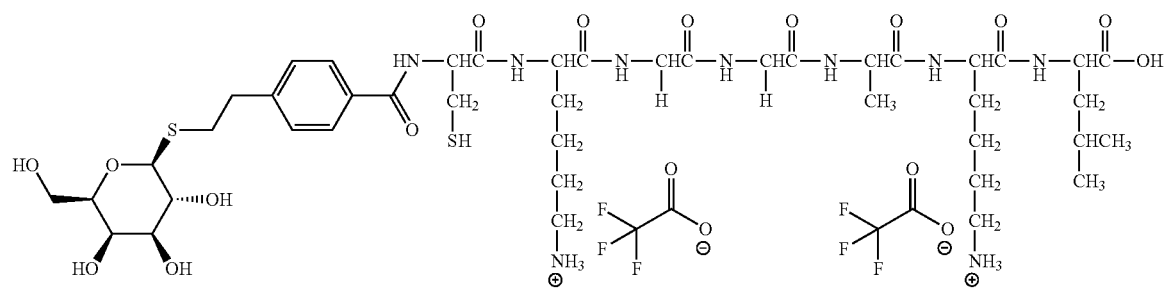
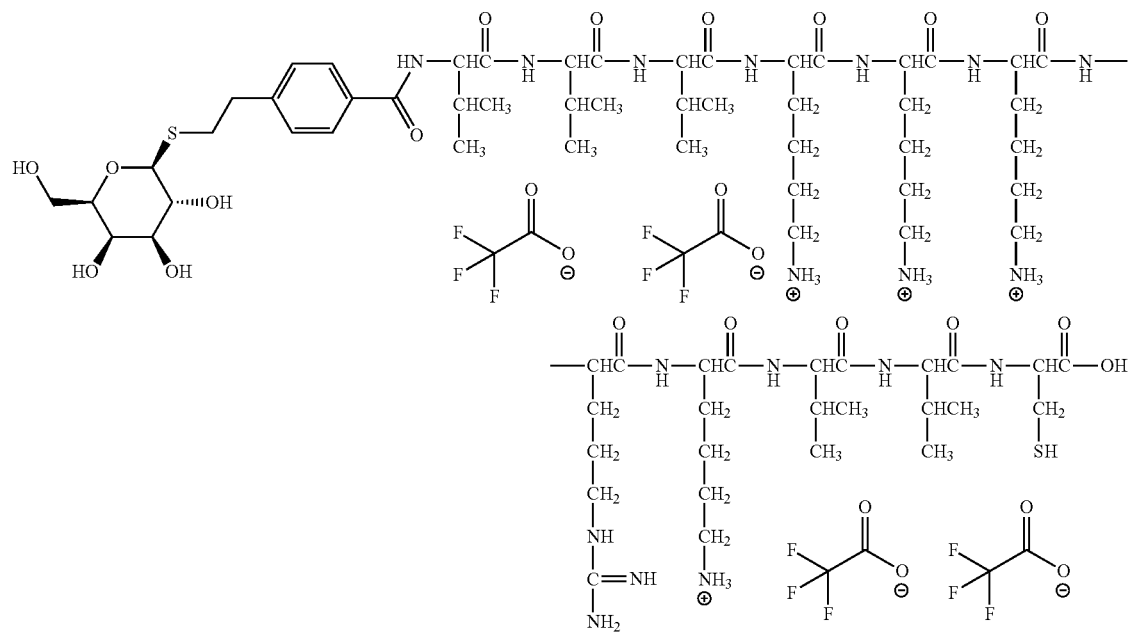

-continued

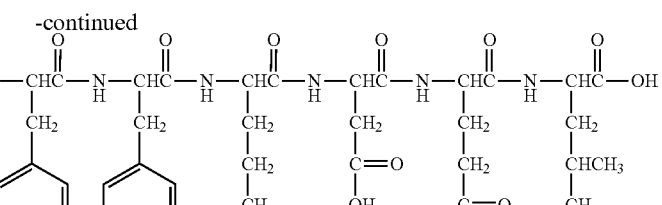
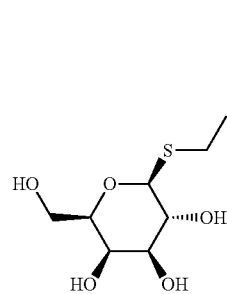
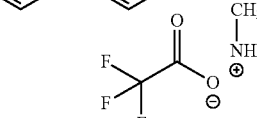
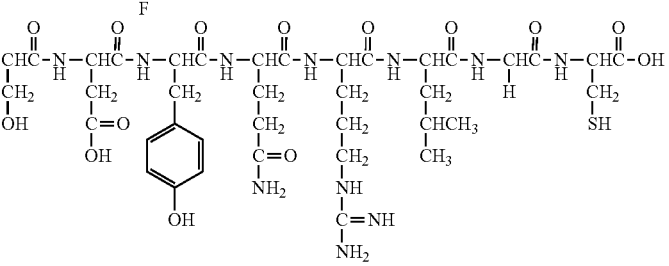
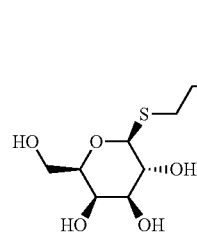

The targeted pharmacological chaperones of the present invention are internalized into the cell via the protein sorting machinery that directs newly synthesized proteins to their distinct destinations in the cell. They accumulate in their target organelles by interaction with receptors that facilitate active import. Extracellular proteins that contain the targeting peptide sequences are partitioned into the cell by the process of retrograde transport. Once in the cell they are freely permeant to cell membranes, and typically selectively accumulate on the luminal face of particular intracellular organelles according to the peptide sequence thereof. The accumulation characteristics of the targeted pharmacological chaperones are generally not reversed or are only partially reversed by subsequent treatment of the cells with additional cell-permeant compounds. Accordingly, accumulation of the TPC may be preserved even after fixation and/or permeabilization of the cells or tissues treated.

The targeted pharmacological chaperones of the present invention are utilized by preparing a pharmacological solution or pharmacological composition containing one or more of the targeted pharmacological chaperone or salts thereof, of the present invention, and introducing the solution or composition to the patient by IV, IM, IP or ID administration in an effective dose. The pharmacological composition may be in combination with an effective amount of a second therapeutic agent selected from the group consisting of glycosidase enzymes, miglustat, eliglustat, glycosylceramide synthase inhibitors such as GZ402671, ambroxol, carbidopa, levodopa, dopamine receptor agonists, anticholinergics, MAO inhibitors, and COMT inhibitors.

In another aspect of the invention, the method comprises administering the pharmaceutical composition in combination with an effective amount of a second therapeutic agent selected from the group consisting of human recombinant β-glucocerebrosidase, human β-galactosidase, human α-mannosidase, lysosomnal acid α-glucosidase, human β-hexosaminidase with or without additional secondary formulation or permeabilization agents. In this method, the targeted pharmacological chaperones act to partition the enzymes used in ERT to specific organelles within the cell, or aide in transport of the enzymes across the outer cell membrane.

Another aspect of the present invention provides methods for preventing and/or treating disease in a patient at risk for developing or diagnosed with the same, which comprises administering to the patient an effective amount of the targeted pharmacological chaperones of the present invention with or without additional therapeutics.

Formulations

The compounds of the present invention can be formulated to be suitable for any route of administration, including e.g., orally in the form of tablets or capsules or liquid, or in sterile aqueous solution for injection. When the compound is formulated for oral administration, tablets or capsules can be prepared by conventional means with pharmaceutically acceptable excipients such as binding agents (e.g., pregelatinized maize starch, polyvinylpyrrolidone or hydroxypropyl methylcellulose; fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); or preservatives (e.g., methyl or propyl-p-hydroxybenzoates or sorbic acid). The liquid preparations may also contain buffer salts, flavoring, coloring or sweetening agents as appropriate. Preparations for oral administration may be suitably formulated to give controlled or sustained release of the compound. In the case of oral administration, the use of peptidomimetics as targeting agents will be preferred due to their increased stability against enzymatic degradation in the digestive system.

In certain embodiments of the present invention, the compound is administered in a dosage form that permits systemic distribution or uptake, such that the compound may cross the blood-brain barrier so as to exert effects on neuronal cells. Such dosage forms that permit systemic distribution or uptake may be oral or parenteral. In some embodiments, the compound may be distributed systemically, including crossing the blood-brain barrier.

For example, pharmaceutical formulations of the compound suitable for parenteral/injectable use generally include sterile aqueous solutions (where the TPC is water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a polyol (for example, glycerol, propylene glycol, polyethylene glycol, and the like), suitable mixtures thereof, or vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate or gelatin.

Sterile injectable solutions are prepared by incorporating the compound in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrolidone; sugars, such as dextran, mannitol, sorbitol, and glycerol; propylene glycol and polyethylene glycol (e.g., PEG 4000, PEG 6000); glycerol; glycine or other amino acids; and lipids. Buffer systems for use with the formulations include citrate; acetate; bicarbonate; and phosphate buffers. Phosphate buffer is a commonly used excipient.

The formulation can also contain a non-ionic detergent. Examples of non-ionic detergents include Polysorbate 20, Polysorbate 80, Triton X-100, Triton X-114, Nonidet P-40, Octyl a-glucoside, Octyl β-glucoside, Brij 35, Pluronic, and Tween 20.

Routes of Administration

The compounds of the present invention may be administered orally or parenterally, including intravenously, subcutaneously, intra-arterially, intraperitoneal, ophthalmically, intramuscularly, buccally, rectally, vaginally, intraorbital, intracerebral, intradermal, intracranially, intraspinally, intraventricularly, intrathecal, intracisternally, intracapsularly, intrapulmonarily, intranasally, transmucosally, transdermal, or via inhalation. In one embodiment, the compound is administered orally.

Administration of compounds may be by periodic injections of a bolus of the formulation, or may be administered by intravenous or intraperitoneal administration from a reservoir which is external (e.g., an i.v. bag) or internal (e.g., a bioerodable implant). See. e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle delivered injection, needle-less injection, nebulizer, aerosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can be administered using these methods.

Subcutaneous injections have the advantages of allowing self-administration, while also resulting in a prolonged plasma half-life as compared to intravenous administration. Furthermore, a variety of devices designed for patient convenience, such as refillable injection pens and needle-less injection devices, may be used with the formulations of the present invention as discussed herein.

Dosage

A suitable pharmaceutical preparation is in a unit dosage form. In such form, the preparation is subdivided into suitably sized unit doses containing appropriate quantities of the active component, e.g., an effective amount of the compound to achieve the desired purpose. In certain embodiments, the compound is administered in one or more daily doses (e.g., once-a-day, twice-a-day, thrice-a-day). In certain embodiments, the compound is administered intermittently, e.g. on nonconsecutive days.

In one embodiment, the compound is administered in a dosing regimen that includes an initial "loading dose" given daily, followed by a period of non-daily intermittent dosing.

The amount of effective compound for preventing or treating Parkinson's disease or lysosomal storage disease can be determined on a case-by-case basis by those skilled in the art. The amount and frequency of administration of the compound will be regulated according to the judgment of the attending clinician (physician) considering such factors as age, condition and size of the patient as well as risk for developing disorder or severity of the symptoms of the referenced disorder being treated.

Combination Drug Therapy

The compounds of the present invention can be administered in combination with at least one other therapeutic agent. Administration of the compounds of the present invention in combination with at least one other therapeutic agent is understood to encompass administration that is sequential or concurrent. In one embodiment, the therapeutic agents are administered in separate dosage forms. In another embodiment, two or more therapeutic agents are administered concurrently in the same dosage form. The additional therapeutic agent or agents may be an enzyme useful for treating the particular enzyme defect.

Among the enzymes that are present in acidic organelles and that can benefit from the therapeutic effects of using the pharmacological chaperones of the present invention are α-Mannosidase, β-Galactosidase, α-Galactosidase, β-Glucosidase, α-Glucosidase, b-Glucuronidase, β-acetylglucosaminidase, Neuraminidase, Hyaluronidase, Lipase, Phospholipase A, Esterase, Acid Phosphatase, Phospholipase C, Acid phospho-diesterase, Arylsulfatase A/B, Chondrosufatase, Lysozyme, β-Xylosidase, α- and β-Fuco-sidases, Cathepsin A, Acid Carboxy-Peptidase, Alanylanminopeptidase, Leucylaminoyeptidase, Dipeptidase, Cathepsin B, Cathepsin H, Cathepsin L, Cathepsin C, Dipeptidyl Aminopeptidase II, Cathepsin D. Cathepsin E, Collagenase, Renin, Kininogen activator, Plasminogen activator, and Aspartylglucosyl aminidase.

Those enzymes listed are given as a descriptive embodiment of the present invention but not intended to be a complete list of possible enzyme activities which may be improved using the targeted pharmacological chaperones and methods of the present invention. Other enzymes which may be involved in disease using the treatment systems and therapeutics of the present invention will be obvious to a person skilled in the art.

The lysosomal storage diseases and allied syndromes linked to specific enzyme defects include:

Glycogen Storage Disease Type II
    Infantile-onset Pompe disease (deficiency of lysosomal acid maltase)
    Late-onset Pompe disease (deficiency of lysosomal acid maltase)

Mucopolysaccharidoses
    MPS type IH, Hurler syndrome (alpha-L-iduronidase deficiency)
    MPS type I H/S, Hurler-Scheie syndrome
    MPS type IS, Scheie syndrome
    MPS type II A, Hunter syndrome, severe (iduronate sulfatase deficiency)
    MPS type II B, Hunter syndrome, mild (iduronate sulfatase deficiency)
    MPS type III A-D, Sanfilippo syndrome (A: heparan N-sulfatase deficiency; B: alpha-N-acetylglucosaminidase deficiency; C: Acetyl-CoA alpha-glucosaminide N-acetyltransferase deficiency: D: N-acetylgalactosamine-6-sulfate sulfatase deficiency)
    MPS type IV A, Morquio syndrome, classic (galactose 6-sulfatase deficiency)
    Morquio disease B (acid beta-galactosidese deficiency)
    MPS type VI, Maroteaux-Lamy syndrome (arylsulfatase B deficiency)
    MPS type VII, Sly syndrome (beta-glucuronidase deficiency)

Mucolipidoses
    Mucolipidosis I: (sialidosis deficiency)
    Mucolipidosis II (I-cell disease) (Pseudo-Hurler Polydystrophy.)
    Mucolipidosis III (phosphotransferase deficiency)
    Mucolipidosis IV (mucolipidin 1 deficiency)

Oligosaccharidoses
    Schindler disease/Kanzaki disease (alpha-N-acetylgalactosaminidase deficiency)
    Alpha-mannosidosis and beta-mannosidcsis (alpha- or beta-mannosidase deficiencies)
    Alpha-fucosidosis: (alpha-fiucosidase deficiency)
    Sialidosis (mucolipidosis I: alpha-N-acetyl neuraminidase [sialidase] deficiency)
    Aspartylglucosaminuria (aspartylglucosarninase deficiency)

Lipidoses
    Nienmann-Pick disease types C and D (cholesterol ester storage)
    Neuronal ceroid lipofuscinoses
    Wolman disease (acid lipase deficiency, mild form cholesterol ester storage disease Sphingolipidoses
    Niemann-Pick disease type A (sphingomyelinase deficiency) and Niemann-Pick disease type B (sphingomyelinase deficiency)
    Gaucher disease types I, II, and III (beta-glucosidase deficiency)
    Krabbe disease, infantile globoid-cell leukodystrophy (galactosylceramidase deficiency)
    Fabry disease (alpha-galactosidase A deficiency)
    GM1 gangliosidosis and Morquio B disease (beta-galactosidase deficiency) GM2 gangliosidoses: These include Tay-Sachs disease (hexosaminidase A deficiency) and Sandhoff disease (hexosaminidase A and B deficiency) Metachromatic leukodystrophy (arylsulfatase A deficiency)
    Farber disease, disseminated lipogranulomatosis (ceramidase deficiency)
    Multiple sulfatase deficiency (sulfatase-modifying factor-1 mutation): Mutation in SUMF1 leads to deficiency of 7 sulfatases.
    Galactosialidosis (cathepsin A deficiency): Mutation in CTSA leads to a combined deficiency of lysosomal beta-galactosidase and neuraminidase as a result of a primary defect in the protective protein/cathepsin A (PPCA).

Lysosomnal Transport Diseases
    Cystinosis (cystine transporter deficiency): Fanconi syndrome
    Sialic acid storage disease (Salla disease; sialic acid transporter deficiency)

Synucleinopathies
    Parkinson's Disease—disruption of synuclein protein homeostatis, Lewy bodies
    Multiple system atrophy—dementia, Lewy bodies
    Alzheimer's Disease—amyloid plaques alpha-synuclein component accumulation.

The examples below are given so as to illustrate the practice of this invention. They are not intended to limit or define the entire scope of this invention.

Example 1: Synthesis of 1-Deoxynojirimycin N-ethylmaleimide

The following compound was prepared:

Methyl tri-O-acetyl-6-deoxy-6-iodo-β-D-glycopyranoside (M1935)

The 6-iodo glucose derivative was prepared using a modification of the method of Gandy, et al, Aust. J. Chem. 63: 1409-1412.). To a 500 mL 1-neck round bottom flask was weighed triphenylphosphine (10.13 g, 38.63 mmole), imidazole (5.29 g. 77.76 mmole), iodine (9.12 g, 35.93 mmole) and methyl β-D-glucopyranoside, hemihydrate (Aldrich, 5.00 g, 24.61 mmole) and the solids were mixed manually. This mixture was suspended in dry toluene (250 mL) and heated to 95° C. overnight. After warming briefly to reflux (30 min.) the reaction was cooled to room temperature, added to water (150 mL) in a 1 L separatory funnel and the toluene layer separated. This organic layer was washed with water (2×50 mL). The combined aqueous layers were washed with toluene (1×50 mL), evaporated on a rotovap (T<50° C.) and dried in vacuo overnight to give a brown oil (18.08 g). This oil was suspended in dry dichloromethane (150 mL), cooled to 0° C. (ice-bath) and acetic anhydride (45 mL) and dry pyridine (45 mL) added. This mixture was allowed to stir at 0° C. for 2 hours and at room temperature overnight until t.l.c. analysis (irrigant 7:3 ethyl acetate:methanol) showed a single product (Rf=0.62). The reaction mixture was poured into ice-water (800 mL) with stirring and the dichloromethane layer separated and washed with fresh water (2×100 mL). The organic layer was dried over anhydrous $MgSO_4$, filtered, evaporated and dried in vacuo overnight to give a tan oil (6.67 g, 63%), homogeneous by tlc, that was used without further purification for the synthesis of M1937.

Methyl tri-O-acetyl-6-deoxy-3-D-xylo-hex-5-enopyranoside (M1937)

A sample of the crude M1935 (6.67 g, 15.50 mmole) was dissolved in anhydrous tetrahydrofuran (100 mL), diazabicycloundecene (9.27 mL) added and this mixture heated to reflux for 5.5 hours, cooled and partitioned with ethyl acetate (150 mL). The ethyl acetate solution was filtered and dried in vacuo to a brown oil (13.59 g) that was applied to a column of silicagel G (70-230 mesh, 600 mL, 55×260 mm) slurry packed in dichloromethane. The crude sample was applied in dichloromethane and eluted with dichloromethane (600 mL), 4% ethyl acetate/dichloromethane (2 L) and 10% ethyl acetate/dichloromethane (500 mL. Fractions containing the first product to elute from the column were combined, evaporated and dried in vacuo to give a white solid (881 mg. 19% j. T.l.c. (irrigant=9:1 dichloromethane: ethyl acetate; Rf=0.61); 1H-NMR (CDCl3): consistent with literature (Skelton B W, Stick R V, Stubbs K A, Watts A G, White A H (2004) Aust. J. Chem. 57: 345-353 (cmpd. 34)).

Methyl 5-C-Benzyloxy-β-D-xylo-hexopyranoside (M1946)

A sample of M1937 (777 mg, 2.57 mmole) was dissolved in dry dichloromethane (35 mL) and benzyl alcohol (35 mL) and m-chloroperbenzoic acid (1.27 g, 70%) added. This solution was allowed to stir under anhydrous conditions at room temperature overnight, transferred to a separatory funnel diluted with dichloromethane (dichloromethane, 50 mL) and washed with 5% sodium bicarbonate solution (2×100 mL) and water (1×50 mL). The final dichloromethane layer was dried over anhydrous $MgSO_4$, filtered and evaporated to give a single product (t.l.c. analysis, irrigant=7:3 ethyl acetate:methanol, Rf=0.88) (1.21 g). This product was dried several days in vacuo to a final weight of 1.10 g, which was then dissolved in anhydrous methanol (100 mL) under dry $N_{2(g)}$ and 25% (w v) NaOMe/methanol solution (228 mg, 6.0 mmole) added. This mixture was allowed to stir under anhydrous condition for 4.5 hours until t.l.c. showed conversion to a single product (t.l.c:irrigant=7:3 ethyl acetate:methanol, Rf=0.74). BioRex. 70 (H+) resin (3 g) was added, the reaction allowed to stir until pH changed to neutral (pH-=6) (30 min.). The resin was filtered and washed with excess methanol. The resulting methanol solution was evaporated and dried in vacuo to give a clear glass (1.034 g) which was further triturated with anhydrous diethylether to produce an off-white solid (529 mg). $^1$H-NMR ($D_2O$) δ: 3.40 (m, 2H); 3.42 (s, 3H, —OCH3); 3.58 (t, 1H: 3.7-3.8 (m, 2H); 4.55 (d, 1H, H–1); 4.60 (d, 2H, —CH2-Ph); 7.27 (m, 5H, Ph). T.l.c. (irrigant=7:3 ethyl acetate:methanol, Rf=0.74).

2-Aminoethyl maleimide (M1954)

The aminomaleimide was prepared by a modification of the method of Baskin, et al. (Jeremy M. Baskin J M, Prescher J A, Laughlin S T, Agard N J, Chan P V, Miller I A, Lo A, Codelli J A, Bertozzi C R (2007) PNAS 104(43): 16793-16797). To a flame-dried 250 mL flask was added maleimide (3.12 g, 32.2 mmole), triphenylphosphine (8.29 g, 31.6 mmole) and dry tetrahydrofuran (100 mL) under anhydrous $N_{2(g)}$. A solution of N-tert-butyloxycarbonyl-ethanolamine (5.00 ml) in dry tetrahydrofuran (50 mL) was added dropwise followed by diisopropylazodicarboxylate (6.80 mL, 35.1 mmole). The reaction was allowed to stir at room temperature under anhydrous condition (dry $N_{2(g)}$) overnight, after which the solution was evaporated and filtered through a bed of silicagel G (70-230 mesh, 150 mL) using 2:1 hexanes:ethyl acetate for elution. Fractions containing the major product were combined, evaporated and dried to give a pale yellow oil (10.11 g).

The oil was dissolved in 60:35:5 dichloromethane:trifluoroacetic acid:water (100 mL) and allowed to stir at room temperature for 2 hours until conversion to a lower Rf product was complete (t.l.c. analysis (irrigant=9:1 dichloromethane:methanol). The reaction was diluted with dichloromethane (50 mL) and water (50 mL), transferred to a separatory funnel and the organic layer separated. The organic layer was further washed with water (3×25 mL). The combined aqueous layers were washed with fresh dichloromethane (3×25 mL), evaporated and co-evaporated with dry toluene (2×20 mL) and dried in vacuo to give a yellow oil that crystallized to a waxy solid on standing (3.62 g, 49%). 1H-NMR (d6-DMSO) δ: 2.82 (q, 2H); 3.59 (t, 2H); 6.83 (s, 4H); 7.78 (br d, 31H).

1-Deoxynojirimycin N-ethylmaleimide (M1964)

Palladium catalyzed transfer reductive animation using triethylsilane was used to prepare the nojirimycin derivative according to the method of Mandal and McMurray (Mandal P K, McMurray J S (2007) JOC 72: 6599-6601.) To a sample of Methyl 5-C-Benzyloxy-f-D-xylo-hexopyranoside (M1946) (70 mg, 0.223 mmole) was added a solution of 2-Aminoethyl maleimide (M1954) (63 ng, 0.256 mmole) in methanol (6.0 mL). 20% $Pd(OH))_2/C$ (17 mg) was added followed by triethylsilane (355 uL, 2.23 mmole) and triethylamine (62 uL, 0.446 mmole). The reaction was sealed and allowed to react overnight, filtered through a bed of Celite™ 545, using a 0.2 micron membrane filter, evaporated and co-evaporated with methanol (3×15 mL) to give a clear oil. The oil was applied to a column of silicagel G (70-230 mesh, dry-packed, 40×25 mm) and eluted with 7:3 thylacetate:methanol as solvent. Fractions containing the first product to elute from the column were combined and evaporated to give a clear oil (13 mg).

Example 2: Synthesis of 1-Deoxynojirimycin N-butylmaleimide ("4-maleimido-N-butyl-Deoxynojirimycin")

N-(Methoxycarbonyl)-maleimide (M1970)

The title compound was prepared using a modification of the method of Foley, et al., 2010 Biomol. Chem. 8:4601-

4606). To a solution of maleimide (5.0 g, 51.5 mmole in dry ethyl acetate (250 mL) was added N-methylmorpholine (5.7 mL, 51.5 mmole) and this mixture cooled to 0° C. (ice-bath) under anhydrous $N_{2(g)}$. Methyl chloroformate (4.8 mL, 61.8 mmole) was added slowly with stirring under anhydrous conditions, and the reaction allowed to stir at 0° C. for 30 min. and at room temperature for 30 min. The reaction mixture was filtered through a Buchner funnel and the white precipitate washed with ethyl acetate (100 mL). The combined filtrate was extracted with ice-water (1×100 mL) and brine solution (1×100 mL) and then dried over anhydrous magnesium sulfate. The product was filtered and evaporated to a clear oil that was co-evaporated with dry toluene (2×25 mL) and dried in vacuo under high vacuum overnight. The resulting clear oil was crystallized by trituration from anhydrous diethylether (50 mL) to give an off-white solid (2.77 g, 35%) homogeneous by t.l.c. (irrigant=9:1 dichloromethane:methanol, Rf=0.62).

N-(4-Hydroxybutyl)-maleimide (M1969)

To a cooled (0° C., ice-bath) solution of 4-amino-1-butanol (1.66 mL, 17.86 mmole) in saturated sodium bicarbonate solution (75 mL) was added M1970 (2.77 g. 17.86 mmole) with stirring. This reaction solution was allowed to stir at 0° C. for 30 min. and at room temperature for 1.5 hours. The solution was extracted with dichloromethane (3×75 mL) and the combined organic extracts were dried over anhydrous magnesium sulfate, filtered, evaporated and dried in vacuo overnight. The crude sample was applied to a column of silicagel G (70-230 mesh, 100 mL) slurry-packed in dichloromethane and eluted with dichloromethane (250 mL) and 9:1 dichloromethane:ethyl acetate (500 mL) and 8:1 dichloromethane:methanol (225 mL). Fractions containing the second major product to elute from the column were combined and evaporated to a clear oil which crystallized on standing to a white waxy solid (1.49 g, 49%). $^1$H-NMR (CDCl$_3$) δ: 1.58 (m, 2H); 1.70 (m, 2H); 3.57 (t, 2H); 3.68 (t, 2H); 4.70 (br s, 1H); 6.70 (s, 2H, maleimide). T.l.c (irrigant=9:1 dichloromethane:methanol; Rf=0.55).

N-Maleimido butane-4-carboxaldehyde (M1973)

To a stirred solution of M1969 (0.99 g, 5.85 mmole) in wet dichloromethane (75 mL) was added solid Dess-Martin periodane (2.73 g. 6.44 mmole) and the resulting suspension allowed to stir at room temperature overnight. The abundant precipitate was filtered, washed with excess dichloromethane and the filtrate was treated with methanol (5 mL) to destroy any excess periodane. The resulting solution was evaporated to a clear oil that was applied to a column of silicagel G (70-230 mesh, 50 mL, 140×25 mm; slurry-packed in dichloromethane and eluted with dichloromethane (250 mL) followed by 9:1 dichloromethane:ethyl acetate (500 mL). Fractions containing the second major product to elute from the column were combined and evaporated to a clear oil (0.98 g). $^1$H-NMR (CDCl$_3$) δ: 1.98 (m, 2H); 2.22 (dt, 2H); 3.60 (t, 2H); 6.85 (s, 2H, maleimide); 9.87 (s, 1H, —CHO). T.l.c. (irrigant=9:1 dichloromethane:methanol, Rf=0.71)

N-(4'-Maleimidobutyl)-1-deoxynojirimycin ("4-maleimido-N-butyldeoxynojirimycin") (M1965)

A solution of the aldehyde (M1973) (49 mg, 0.26 mmole) and 1-deoxynojirimycin (33 mg, 0.2 mmole) in anhydrous methanol (5 mL) containing glacial acetic acid (24 uL, 0.4 mmole) was allowed to stir at room temperature for 30 min. To this mixture was added 1 M sodium cyanoborohydride in anhydrous tetrahydrofuran (300 uL, 0.3 mmole) and the resulting reaction mixture allowed to stir under anhydrous conditions for 72 hours until t.l.c. analysis (irrigant 7:3 ethyl acetate:methanol) exhibited complete conversion of M1973 to a new product (Rf=0.2). Water (2.0 mL) was then added with stirring for 10 min. to destroy the excess borohydride, and the resulting solution evaporated and co-evaporated with methanol (3×5 ml) to a clear glass that was applied to a column of silicagel G (70-230 mesh, 25 g) slurry-packed in 3:1 ethyl acetate:methanol (120×25 mm) and eluted with 3:1 ethyl acetate:methanol (300 mL). Fractions containing the product were combined and evaporated to a clear oil (47 mg, 75%). $^1$H-NMR (d$_6$-DMSO) δ: 1.34 (m, 2H); 1.40 (m, 2H); 2.30 (m, 1H); 2.74 (td, 2H); 2.90 (t, 1H); 2.98 (t, 1H); 3.15 (m, 1H), 3.36 (t, 1H); 3.50 (m, 1H); 3.71 (d, 1H); 4.11 (m, 1H); 4.67 (m, 3H), 7.00 (s, 2H, maleimide). T.l.c (irrigant=7:3 ethyl acetate:methanol, Rf=0.2).

Example 3: Synthesis of 1-Deoxymannonojirimycin N-butylmaleimide ("4-maleimido-deoxymannonojirimycin")

A solution of the aldehyde (M1973) (8.4 mg, 0.05 mmole) and 1-deoxymannonojirimycin, HCl salt (5 mg, 0.025 mmole) in anhydrous methanol (5 mL) containing glacial acetic acid (5 uL, 0.09 mmole) was allowed to stir at room temperature for 30 min. To this mixture was added 1 M sodium cyanoborohydride in anhydrous tetrahydrofuran (50 uL, 0.05 mmole) and the resulting reaction mixture allowed to stir under anhydrous conditions for 72 hours until t.l.c. analysis (irrigant=7:3 ethyl acetate:methanol) exhibited complete conversion of M1973 to a new product (Rf=0.1). Water (10 uL) was added with stirring for 10 min. to destroy the excess borohydride, and the resulting solution evaporated and co-evaporated with methanol (3×5 ml) to a clear glass that was applied to a column of silicagel G (70-230 mesh, 10 g) slurry-packed in 3:1 ethyl acetate:methanol (40×25 mm) and eluted with 3:1 ethyl acetate:methanol (200 mL,). Fractions containing the product were combined and evaporated to a clear oil (7 mg, 87%). $^1$H-NMR (D$_2$O) δ: 1.58 (m, 2H); 1.63 (m, 2H); 2.67 (s, 1H); 2.99 (d, 1H); 3.14 (m, 2H); 3.25 (d, 1H); 3.38 (d, 1H); 3.58 (m, 1H); 3.86 (t, 1H); 3.96 (q, 1H); 3.99 (d, 1H); 4.07 (m, 1H); 4.14 (m, 3H); 6.73 (s, 2H, maleimide). T.l.c (irrigant=7:3 ethyl acetate:methanol, Rf=0.1).

Example 4: Synthesis of 1-Deoxygalactonojirimycin N-butylmaleimide ("4-maleimido-deoxygalactonojirimycin")

A solution of the aldehyde (M1973) (14.6 mg, 0.088 mmole and 1-deoxygalactonojirimycin. HCl salt (8.7 mg, 0.044 mmole) in anhydrous methanol (15 mL) containing glacial acetic acid (9 uL, 0.15 mmole) was allowed to stir at room temperature for 30 min. To this mixture was added 1 M sodium cyanoborohydride in anhydrous tetrahydrofuran (100 uL, 0.10 mmole) and the resulting reaction mixture allowed to stir under anhydrous conditions for 72 hours until t.l.c. analysis (irrigant=7:3 ethyl acetate:methanol) exhibited complete conversion of M1973 to a new product (Rf=0.1). Water (1 mL) was added with stirring for 10 min. to destroy the excess borohydride, and the resulting solution evaporated and co-evaporated with methanol (3×15 ml) to a clear glass that was applied to a column of silicagel G (70-230 mesh, 25 g) slurry-packed in 3:1 ethyl acetate:methanol (140×25 mm) and eluted with 3:1 ethyl acetate:methanol (200 mL). Fractions containing the product were combined and evaporated to a clear oil (12 mg, 88%). $^1$H-NMR confirmed the chemical structure. T.l.c (irrigant=7:3 ethyl acetate:methanol, Rf=0.1).

Example 5: Synthesis of D-Glucosamine N-butylmaleimide ("4-maleimido-GluN")

The synthesis procedure and compound analysis of Example 5 was used for the preparation of the title compound, except that D-glucosamine hydrochloride was substituted for an equivalent amount of -deoxygalactonojirimycin, HCl salt for preparation of N-butylmaleimido D-glucosamine. Its molecular mass was 331.34 (M4-H) as determined by laser desorption mass spectrometry and its chemical structure was confirmed by 1D-$^1$H NMR.

Example 6: Preparation of Ethyl 4-(2-mercaptoethyl) benzoate 5.8 ml (0.08 mmol) of thionyl chloride is added dropwise to a mixture of 11.28 g (0.061 mol) of 4-(2-chloroethyl) benzoic acid in 36 ml of ethanol and heated to 50° C. The reaction medium is then refluxed for 6 hours, poured into ice-water and neutralized with sodium hydrogen carbonate. The product is extracted with ethyl ether. The organic phases are combined, washed with water dried over magnesium sulfate and concentrated on a rotary evaporator under vacuum to give ethyl 4-(2-chloroethyl)benzoate, 12.70 g (98%) as a yellow oil. A mixture of 12.24 g (0.057 mol) of ethyl 4-(2-chloroethyl)benzoate, 13.15 g (0.115 mol) of potassium thioacetate and 78 mg (0.6% by mass) of sodium iodide in 250 al of methyl ethyl ketone is refluxed for 5 hours. After cooling to room temperature, the reaction mixture is poured into saturated solution ammonium chloride and extracted with ethyl ether. The organic phases are combined, washed with water, dried over magnesium sulfate and concentrated under vacuum to give ethyl 4-(2-acetylsulfanylethyl)benzoate, 14.45 g (100%) as a brown oil. A mixture of 14.7 g (0.058 mol) of ethyl 4-(2-acetylsulfanylethyl)benzoate and 10.42 g (0.075 mol) of potassium carbonate in 220 ml of ethanol is stirred at room temperature overnight. The reaction mixture is poured into ice-cold 2N hydrochloric acid solution and extracted with ethyl ether. The organic phases are combined, washed twice with water, dried over magnesium sulfate and concentrated under vacuum to give a brown oil (12.2 g) that is purified by silicagel column chromatography using (90:10 heptane: ethyl acetate as solvent. Evaporation of the fractions containing the main product provide the title compound (3.87 g; 32%) as a brown liquid along with 7.40 g (61%) of corresponding disulfide, also isolated as a brown oil.

Example 7: Preparation of 4-Aminobenzylchloride

The title compound was prepared using a modification of the method of Han and Jang (1990) Tet. Lett. 31(8): 1181-1182.). To a flame-dried 100 mL round-bottom flask was added 4-nitrobenzyl chloride (1.71 g, 10.0 mmol), montmorillonite K10 (3.00 g), and absolute ethanol (10.0 mL). To the stirred suspension was added anhydrous hydrazine (3.04 mL, 62.5 mmole) via syringe. The solution was heated to 40° C. After 2.5 h, the montmorillonite was removed via filtration. The filtrate was concentrated in vacuo, co-evaporating with toluene (2×5.0 mL), then dried in vacuo. The resulting yellow oil was purified via flash chromatography over silica, using dichloromethane as solvent, to give the desired aniline (1.28 g, 90% yield). $^1$H-NMR (d$_6$-DMSO) was consistent with the structure.

Example 8: 4-Carboxyphenethyl 1-deoxy-1-thio-β-D-glucopyranoside

The title compound was prepared using a modification of the procedure of Helferich, et al. (1956) Chem. Ber. 89(10) 2220-2224). A solution of potassium metal (2.01 g. 50 mmole) in dry methanol (80 mL) is prepared. To this solution is added ethyl 4-(2-mercaptoethyl)benzoate (6.0 mL, 45 mmole) at 0° C. (ice-bath) under anhydrous N$_{2(g)}$. 16 mL of the above solution was removed, for analytical purposes. To the remaining solution at 0° C. was added acetobromoglucose (16.45 g. 45 mmole) in portions and the resulting reaction allowed to stir at 0° C. for 2 hours and at room temperature overnight. The white precipitate was filtered and washed with methanol (3×20 mL) and water (3×20 mL) and dried in vacuo overnight. The crude product was recrystallized from hot ethanol (200 mL) to give 8.82 g (40%) of the protected glycoside as white crystals.

A sample of the crystalline peracetyl thioglucoside (4.69 g) was suspended in anhydrous methanol (200 mL), cooled to 0° C. and sodium methoxide in methanol (3.61 N, 1 mL) added. This reaction mixture was allowed to stir under anhydrous N$_{2(g)}$ at 0° C. for 2 hours and at room temperature for 1 hour. The reaction was then neutralized by adding washed, dry IRC-50 (H+) resin (2 g), the resin filtered and the filtrate evaporated to a clear foam (3.17 g) that was recrystallized from dry acetone and petroleum ether to give a colorless foam (3.09 g, 99%). $^1$H n.m.r. (d$_6$-DMSO): δ: 12.0 (s, 1H); 7.9 (d, 2H); 6.7 (d, 2H); 4.7 (br s, 4H, 4×—OH); 4.3 (d, 1H, H–1); 3.7 (d, 1H); 3.5-3.4 (m, 2H); 3.2-2.8 (m, 3:1), m.p.=32-136° C. (d).

Example 9: 4-(p-Chloromethylphenylcarboxamido)phenethyl 1-deoxy-1-thio-β-D-glucopyranoside To a solution of 4-carboxyphenethyl 1-deoxy-1-thio-β-D-glucopyranoside (500 mg. 1.33 mmole) in anhydrous tetrahydrofuran (25 mL) was added diisopropylethylamine (262 uL, 1.5 mmole). The reaction mixture was cooled to 0° C. (ice-bath) under dry N$_{2(g)}$, and isobutylchloroformate (183 uL 1.4 mmole) added. After stirring at 0° C. for 30 min., a solution of 4-aminobenzylchloride (188 mg, 1.33 mmole) in anhydrous tetrahydrofuran (10 mL) was added slowly with stirring and the resulting reaction mixture allowed to stir at 0° C. for 2 hours and at room temperature overnight. The resulting reaction mixture was filtered, and evaporated to dryness, redissolved in ethyl acetate and extracted with water (1×50 mL), 1 N HCl solution (1×50 mL) and water (1×50 mL). The resulting organic layer was concentrated to a small volume and applied directly to a column of silicagel G (70-230 mesh) and eluted with ethyl acetate to give the title compound as an off white solid (498 mg, 75%).

Example 10: Peptide-4-(p-chloromethylphenylcarboxamido)phenethyl 1-deoxy-1-thio-β-D-glucopyranoside Drug Conjugations Preparation of Stock Solutions A solution of NHAc-Cys-Lys-Gly-Gly-Ala-Lys-Leu-COOH, (SEQ ID NO:3) di-TFA salt (Peptide 1) is prepared by dissolving the peptide (2.8 mg, 3.0 μmol) into sterile, autoclaved H$_2$O (60.0 μL) to give a 50.0 mM solution.

A solution of NHAc-Val-Val-Val-Lys-Lys-Lys-Arg-Lys-Val-Val-Val-CysCOOH (SEQ ID NO:4), tetra TFA salt (Peptide 2) is prepared by dissolving the peptide (5.3 mg, 3.0 µmol) into sterile, autoclaved H$_2$O (60.0 µL) to give a 50.0 mm solution.

A solution of NHAc-Cys-Phe-Phe-Lys-Asp-Glu-Leu-COOH, (SEQ ID NO:5) TFA (Peptide 3) is prepared by dissolving the peptide (3.2 mg, 3.0 µmol) into 1.1 Ethanol/H$_2$O (120.0 µL) to give a 25.0 mM solution.

A solution of NH$_2$-Gly-Ala-Ser-Asp-Tyr-Gln-Arg-Leu-Gly-Cys-COOH, (SEQ ID NO:6) TFA salt (Peptide 4) is prepared by dissolving the peptide (3.1 mg, 3.0 µmol) into sterile, autoclaved 1-420 (60.0 µL) to give a 50.0 mM solution.

A solution of 4-(p-chloromethylphenylcarboxamido)phenethyl 1-deoxy-1-thio-β-D-glucopyranoside is prepared by dissolving the drug analog (3.0 rag, 60 umol) into autoclaved H$_2$O (120.0 µL) to produce a 50.0 mM solution.

A solution of triethylamine is prepared by dissolving triethylamine (140 µL, 1.00 mmol) into autoclaved H$_2$O (9.86 mL) to give a 100 mM solution. A 100 µL aliquot of the 100 mM solution is diluted to 1 mM with autoclaved H$_2$O (9.90 mL). A 100 µL aliquot of the 1 mM solution is diluted to 0.167 mM with autoclaved H$_2$O (500 µL).

Conjugation of 4-(p-Chloromethylphenylcarboxamido)phenethyl 1-deoxy-1-thio-β-D-glucopyranoside to Peptides Peptide 1/drug conjugate: To a 1.5 mL Eppendorf tube is added a 20.0 µL aliquot of the 50.0 mM Peptide 1 solution, a 20.0 µL aliquot of the 50 mM 4-(p-chloromethylphenylcarboxamido)phenethyl 1-deoxy-1-thio-β-D-glucopyranoside solution, and a 60.0 µL aliquot of the 0.167 mM triethylamine solution. The solution is sonicated for 2 hours to produce the desired peptide-drug conjugate (10 mM), which is purified by Reversed Phase HPLC.

Peptide 2/drug conjugate: To a 1.5 mL Eppendorf tube is added a 20.0 µL aliquot of the 50.0 mM Peptide 2 solution, a 20.0 µL aliquot of the 50 mM 4-(p-chloromethylphenylcarboxamido)phenethyl 1-deoxy-1-thio-β-D-glucopyranoside solution, and a 60.0 µL aliquot of the 0.167 mM triethylamine solution. The solution is sonicated for 2 hours to produce the desired peptide-drug conjugate (10 mM), which is purified by Reversed Phase HPLC.

Peptide 3/drug conjugate: To a 1.5 mL Eppendorf tube is added a 40.0 µL aliquot of the 25.0 mM Peptide 3 solution, a 20.0 µL aliquot of the 50 mM 4-(p-chloromethylphenylcarboxamido)phenethyl 1-deoxy-1-thio-β-D-glucopyranoside solution, and a 40.0 µL aliquot of the 0.167 mM triethylamine solution. The solution is sonicated for 2 hours to produce the desired peptide-drug conjugate (10 mM), which is purified by Reversed Phase HPLC.

Peptide 4/drug conjugate: To a 1.5 mL Eppendorf tube is added a 20.0 µL aliquot of the 50.0 mM Peptide 4 solution, a 20.0 µL aliquot of the 50 mM 4-(p-chloromethylphenyl-carboxamido)phenethyl 1-deoxy-1-thio-β-D-glucopyranoside solution, and a 60.0 µL aliquot of the 0.167 mM triethylamine solution. The solution is sonicated for 2 hours to produce the desired peptide-drug conjugate (10 mM), which is purified by Reversed Phase HPLC.

Example 11: Direct Peptide Coupling to 2-[4-(5-carboxypentyl)phenyl]ethyl 1-deoxy-1-thio-β-D-glucopyranoside Peptides were obtained from Sigma Biosciences (Sterling, Va.) as follows:

Peptide 1:
H$_2$N-Cys-Phe-Phe-Lys(Dde)-Asp-Glu-Leu-COOH, TFA salt;

Peptide 2:
H$_2$N-Gly-Ala-Ser-Asp-Tyr-Gln-Arg-Leu-Cys-COOH, TFA salt.

Preparation of 2-[4-(5-carboxypentyl)phenyl]ethyl 1-deoxy-1-thio-β-D-glucopyranoside, NHS ester (M2448)

Under anhydrous conditions, to a solution of 2-[4-(5-carboxypentyl)phenyl]ethyl 1-deoxy-1-thio-β-D-glucopyranoside (29 mg, 73 µmol) in N,N-dimethylformamide (2.9 mL) was added N-(3-dimethylaminopropyl)-N'-ethylcarbodiimide (14 mg, 73 µmol) and N,N-diisopropylethylamine (25.0 µL, 145 µmol). After 60 min, N-hydroxysuccinimide (12.0 mg, 104 µmol) was added. After 48 h, additional N-(3-dimethylaminopropyl)-N'-ethylcarbodiimide (9.0 mg, 47 µmol) was added. After 5.5 h, TLC monitoring showed the reaction was complete. The reaction solution was then diluted in ethyl acetate (50 mL) and poured into ice-cold H$_2$O (50 mL). The aqueous layer was extracted with ethyl acetate (2×50 mL), and the combined organic layers were washed with sat aq. NaCl (50 ml.). The dried organic layer (over MgSO$_4$) was filtered, concentrated and dried in vacuo to give M2448 (26 mg, 52 µmol, 72%) as a clear oil.

Preparation of Thio-Glc/Peptide 1 Conjugate (M2462)

To a solution of M2448 (5.8 mg, 12 µmol) in N,N-dimethylformamide (60.0 µL) was added Peptide 1 (6.4 mg, 6.0 µmol) and N,N-diisopropylethylamine (2.0 µL, 12.0 µmol). The solution was briefly sonicated, then gently agitated at room temperature. After 3 days, the reaction solution was diluted with ethyl acetate (600 µL), which caused the product to precipitate from solution. The suspension was centrifuged; the supernatant was discarded, and the precipitate was washed with ethyl acetate (1.0 mL), centrifuged and decanted. The 1-(4,4-dimethyl-2,6-dioxocyclohex-1-ylidene)-3-ethyl protecting group on the lysine residue of the resulting protected peptide-drug conjugate (M2450) was removed by dissolving the white solid in 2% v/v anhydrous hydrazine in N,N-dimethylformamide (60.0 µL). After 10 min, TLC monitoring showed complete deprotection. The product was then precipitated from ethyl acetate (1.0 mL), centrifuged and decanted. The precipitate was washed with additional ethyl acetate (1.0 mL, centrifuged and decanted, then dried in vacuo to give M2462 as a white solid.

Preparation of Thio-Glc/Peptide 2 Conjugate (M2451)

To a solution of M2448 (2.9 mg, 6.0 µmol) in N,N-dimethylformamide (30.0 µL) was added Peptide 1 (3.4 mg, 3.0 mmol) and N,N-diisopropylethylamine (1.0 µL, 6.0 µmol). The solution was briefly sonicated, then gently agitated at room temperature. After 3 days, the reaction solution was diluted with ethyl acetate (300 µL), which caused the product to precipitate from solution. The suspension was centrifuged; the supernatant was discarded, and the precipitate was washed with ethyl acetate (1.0 mL), centrifuged and decanted, then dried in vacuo to give M2451 as a white solid.

A similar conjugation/deprotection strategy may be used to produce thioglucose/peptide conjugates that may target other organelles, e.g. the nucleus and the peroxisome.

Example 12: Analysis of Targeted Pharmacological Chaperone Activity Using a Lysis Assay Technique Gaucher Cell Lysate Assay using 4-MUGlc. Primary fibroblasts from Gaucher I (GM04394), Gaucher II (GM02627) and Gaucher III (F0971986) patient samples were grown in media (MEM containing 10% FCS). Cells wore plated at $1 \times 10^5$ cells/mL in 96 well plates and treated with each TPC to give a final TPC concentration of 30, 50 or 100 µM or left untreated (media alone, control) for 3 days at 37° C., 5% $CO_2$. After incubation, the cells were washed with PBS (3×100 uL), and assay buffer (0.1M sodium citrate, 0.2M sodium phosphate, 0.1% Triton X-100, 0.25% sodium taurocholate, pH 5.2) (100 uL) added. Cells were harvested by scraping using a cell scraper. The resulting lysate was centrifuged at 14000×g for 2 minutes to remove cellular debris. The protein content of the lysate was calculated using a standard BCA assay. Appropriate volumes of lysate to give equal amounts of protein were then transferred to 1.5 mL microcentrifuge tubes and the volume made up to 99 ul with assay buffer. Substrate reagent (300 mM of 4-MUGlc) was added to each tube (1 uL). The reactions were then incubated at 37° C. for 2 hours. The reaction was stopped by the addition of 1 mL of stop buffer (400 mM Glycine buffer, pH10.8). The stopped reaction solution was added to individual wells of a 96-well microtiterplate (100 uL, in triplicate). Wells were read using a TECAN Infinite M200 Pro Fluorescence microplate reader using EX 355 nm and EM 460 nm and data subtracted from BLANK (assay buffer alone plus 4-MUGlc). FIG. 7 shows analysis of enzyme levels in patient fibroblast cell lines after treatment with targeted pharmacological chaperones. Following drug treatment cells were washed with PBS prior to lysis with buffer at pH 5.2 containing 0.25% sodium taurocholate. Protein content of lysate was measured by BCA assay and this was used to normalize amount of protein present in assay. Lysates were incubated with 3 mM 4-methylumbelliferyl β-D-glucopyranoside for 2 hours and the reaction stopped by the addition of 400 mM glycine buffer, pH 10.8. Fluorescence was measured using Tecan Infinite M200 Pro plate reader and enzyme activity as a percentage of that of non-diseased cells calculated.

Example 13: Peptide Maleimido-Drug Conjugations

Preparation of Stock Solutions

A solution of NHAc-Cys-Lys-Gly-Gly-Ala-Lys-Leu-COOH, (SEQ ID NO:3) di-TFA salt (Peptide 1) was prepared by dissolving the peptide (2.8 mg, 3.0 mmol) into autoclaved $H_2O$ (60.0 µL) to give a 50.0 mM solution.

A solution of NHAc-Val-Val-Val-Lys-Lys-Lys-Arg-Lys-Val-Val-Val-CysCOOH (SEQ ID NO:4), tetra TFA salt (Peptide 2) was prepared by dissolving the peptide (5.3 mg, 3.0 µmol) into autoclaved $H_2O$ (60.0 µL) to give a 50.0 mM solution.

A solution of NHAc-Cys-Phe-Phe-Lys-Asp-Glu-Leu-COOH (SEQ ID NO:5) TFA (Peptide 3) was prepared by dissolving the peptide (3.2 mg, 3.0 µmol) into 1:1 Ethanol/$H_2O$ (120.0 µL) to give a 25.0 mM solution.

A solution of $NH_2$-Gly-Ala-Ser-Asp-Lys-Gln-Arg-Leu-Gly-Cys-COOH (SEQ ID NO:6), TFA salt (Peptide 4) was prepared by dissolving the peptide (3.1 mg, 3.0 µmol) into autoclaved $H_2O$ (60.0 µL) to give a 50.0 mM solution.

A solution of nojirimycin 4-butylmaleimide (M1965) was prepared by dissolving the drug analog (1.9 mg, 60.6 umol) into autoclaved $H_2O$ (120.0 µL) to produce a 50 mM solution.

A solution of triethylamine was prepared by dissolving triethylamine (140 µL, 1.00 mmol) into autoclaved $H_2O$ (9.86 mL) to give a 100 mM solution. A 100 µL aliquot of the 100 mM solution was diluted to 1 mM with autoclaved $H_2O$ (9.90 mL). A 100 µL aliquot of the 1 mM solution was diluted to 0.167 mM with autoclaved $H_2O$ (500 µL).

Conjugation of M1965 to Peptides:

Peptide 1: drug conjugate (M2089): To a 1.5 mL Eppendorf tube was added a 20.0 µL aliquot of the 50.0 mM Peptide 1 solution, a 20.0 µL aliquot of the 50 mM nojirimycin 4-butylmaleimide solution, and a 60.0 µL aliquot of the 0.167 mM triethylamine solution. The solution was sonicated for 2 hours to produce the desired peptide-drug conjugate (10 mM), which was purified by Reversed Phase HPLC.

Peptide 2: drug conjugate (M2090): To a 1.5 mL Eppendorf tube was added a 20.0 µL aliquot of the 50.0 mM Peptide 2 solution, a 20.0 µL aliquot of the 50 mM nojirimycin 4-butylmaleimide solution, and a 60.0 µL aliquot of the 0.167 mM triethylamine solution. The solution was sonicated for 2 hours to produce the desired peptide-drug conjugate (0 mM), which was purified by Reversed Phase HPLC.

Peptide 3: drug conjugate (M2091): To a 1.5 mL Eppendorf tube was added a 40.0 µL aliquot of the 25.0 mM Peptide 3 solution, a 20.0 ILL aliquot of the 50 mM nojirimycin 4-butylmaleimide solution, and a 40.0 µL aliquot of the 0.167 mM triethylamine solution. The solution was sonicated for 2 hours to produce the desired peptide-drug conjugate (10 mM), which was purified by Reversed Phase HPLC.

Peptide 4: drug conjugate (M2092): To a 1.5 mL Eppendorf tube was added a 20.0 µL aliquot of the 50.0 mM Peptide 4 solution, a 20.0 t, aliquot of the 50 mM nojirimycin 4-butylmaleimide solution, and a 60.0 µL aliquot of the 0.167 mM triethylamine solution. The solution was sonicated for 2 hours to produce the desired peptide-drug conjugate (10 mM), which was purified by Reversed Phase HPLC.

Example 14: Enzyme Analysis

Porcine liver α-glucosidase I and rat liver α-glucosidase II were purified to homogeneity and assayed by conventional procedures as previously described by Karlsson et al., J. Biol., Chem. 26.8, 570-576 (1993). β-D-Glucosyl-N-acylsphingosine glucohydrolase (glucocerebrosidase) was isolated from human placenta and purified to homogeneity according to published standard methods [Furbish et al., Proc. Natl. Acad. Sci. USA 74, 3560-3563 (1977); Dale and Beutler. Ibid. 73, 4672-4674 (1976)]. Glucocerebrosidase activity was measured by adding enzyme (5-50 uL) to a sonicated suspension of buffer (50 uL of 50 mM sodium citrate/sodium phosphate buffer, pH 5.0) containing glucosyl ceramide (1 mM), Triton X-100 non-ionic surfactant 10.25% v/v) and sodium taurodeoxycholate (0.6% v/v) that had been previously dried under nitrogen from chloroform:methanol (2:1 v/v) solutions. After incubation at 37° C. for 15-60 min., the reaction was stopped by the addition of 500 uL of chloroform:methanol and the phases separated by centrifugation. The upper phase was washed twice with Folch theoretical lower phase [Folch et al., J. Biol. Chem. 226, 497-509 (1957)] desalted using AG50-X12 ion exchange resin and dried under vacuum. The reaction products were separated by high performance anion exchange chromatography (Dionex BioLC System) and detected by pulsed amperometry. The amount of enzyme-released glucose was calculated from peak areas by applying experimentally determined response factors for glucose relative to an included reference monosaccharide [Butters et al, Biochem. J. 279, 189-195 (1991)].

Example 15: Preparation of Immortalized Human Leukocyte Cell Lines

In order to provide sufficient quantities of cells for HTS screening, well characterized patient leukocytes and fibroblasts were immortalized by transfection. There are several methods known in the art for immortalizing mammalian cells in culture, including the use of viral genes (simian virus 40 T antigen, Epstein-Barr Virus—EBV), overexpression of oncogenes (Ras or Myc T58A mutants), inhibition of tumor-suppressor genes (p53 or RB siRNA) or expression of Telomerase Reverse Transcriptase protein (TERT). The latter strategy proved to be the most effective for cells most affected by telomere length, such as human cells (Lundberg A S, Hahn W C, Gupta P, Weinberg R A. (2000) Curr. Opin. Cell Biol. 12(6):705-9; Fridman A L, Tamsky M A. (2008) Oncogene. 27(46):5975-87.). This protein is inactive in most somatic cells, but when hTERT is exogenously expressed, the cells are able to maintain sufficient telomere lengths to avoid replicative senescence. Another advantage of hTERT immortalized cells is that they maintain a stable genotype and retain critical phenotypic markers. Vectors containing the catalytic subunit of hTERT are commercially available (ABM, Addgene (plasmid 1773), BioGenova). Our laboratories have used the hTERT plasmid successfully in the past to immortalize fibroblasts from patients with extreme insulin resistance and slow in vitro growth (Longo et al., 2002). Herein, we describe our method to immortalize fibroblasts from patients with lysosomal storage disorders (LSDs) using the same technology. Fibroblasts were obtained from patients with different clinical indications, including Gaucher, Krabbe, Fabry, various mucopolysaccharidoses and other LSD syndromes as well as matching leukocytes from several of the same patients originally obtained for diagnostic purposes. These cells were well characterized for enzyme activity of selected lysosomal enzymes and for the specific mutations leading to defective enzyme activity.

Cells were freshly seeded in 6-well plates and incubated overnight in 2 mL of growth medium with a replication-defective lentivirus (obtained commercially from ABM) containing hTERT and selectable markers (Neomycin/Kanamycin resistance) under control of the SV40 promoter in the presence of polybrene (final concentration 8 ug/mL). The following day, cells were washed and incubated with normal medium. With continued cell passages, only the immortal cells (i.e. transfected with hTERT) remained in culture and these provided a continuous source of cells for analysis. In addition, we obtained fresh blood samples from living patients and obtained lymphoblasts by EBV infection of freshly isolated lymphocytes. These procedures provided immortal human cell lines exhibiting natural mutations in genes encoding for lysosomal enzymes to study accumulation of substrate and enzyme activity.

Example 16: Staining and Analysis of Enzyme Levels after TPC Treatment in Immortalized Patient Leukocyte Cell Lines Human immortalized B-Lymphocytes from Gaucher disease and healthy donors were obtained from the Coriell Institute for Medical Research (Camden, N.J.). Cell lines were maintained in RPMI 1640 Medium (HyClone) supplemented with 10% Fetal Bovine Serum (Hyclone) and 1× Antibiotic/Antimycotic (Toku-e). Cells were maintained at a density between 2 and $5\times10^5$ cells/mL, cells were passed by dilution into fresh media. Cells were incubated at 37° C., with 5% $CO_2$ atmosphere.

Prior to analysis, cells were counted and seeded in round bottom 96 well plates at $5\times10^5$ cells/mL using 50 uL of cell suspension per well. The TPCs were then applied in complete media to a final concentration of 0, 10, 50 or 100 uM and incubated for 2 days at 37° C. 5% $CO_2$. After incubation the labeling solution containing appropriate substrates for the enzyme being analyzed in serum free media was added to the cells and incubated at 37° C. for 16 to 24 hours. Since the substrates are not fluorescent at the measurement wavelengths until enzyme activity occurs, the leukocytes do not need to be further washed. A buffer change can be implemented after staining by adding fresh culture media or Opti-Klear™ Cell Imaging Buffer (Marker Gene Technologies, Inc, Eugene, Oreg.). The cells were then photographed using a Zeiss AxioObserver A1 epifluorescence inverted microscope equipped with an QiClick ICX285 CMOS CCD digital camera (QImaging, Surrey, BC, Canada) using an appropriate filter set for the fluorophore used. The cells were also imaged using the EVOS Auto-FL automated live-cell imaging system (Life Technologies, Carlsbad, Calif.) using appropriate filter sets for the fluorophore used in staining. Results were digitized and interpreted using CellProfiler™ cell imaging analysis software (Broad Institute, MIT; http://www.cellprofiler.org/) or Acapella High Content Analysis Software package and data normalized versus equivalent staining with normal human leukocytes. FIG. 11 shows a representative experiment where Gaucher I B-Lymphocytes (GM10870) were incubated with varying TPC concentration for 2 days then a LysoLive™ targeted fluorescent GCase substrate was added to cells at 5 uM maintaining TPC treatment and incubated again overnight. Prior to imaging staining media was removed and cells bathed in Opti-Klear™ imaging buffer containing 1 ug/mL Hoechst 33342. Images were captured using AMG EVOS Auto-FL microscope and then subjected to CellProfiler analysis to measure relative staining intensity.

Example 17: Preparation of Adherent Cells in Culture for Analysis of Targeted Pharmacological Chaperone (PC) Activity Human skin fibroblasts from Lysosomal Storage Disease patients (for example: Krabbe, Tay-Sachs, Sandhoff, Wolman, and Gaucher diseases) were obtained from the Istituto Giannina Gaslini (Genova, Italy) or the Coriell Institute (Camden, N.J.). Cell lines were maintained in RPMI 1640 Medium (HyClone) or MEM/EBSS supplemented with 10% Fetal Bovine Serum (Atlanta Biologicals) and 1× Antibiotic/Antimycotic (Toku-e). Cells were grown to 90% confluence and passaged by splitting at a 1:5 ratio. Cells used for staining were incubated at 37° C., with 5% CO: atmosphere.

Human skin fibroblasts from a healthy specimen were obtained from the Coriell Institute for Medical Research (Camden, N.J.). Cells were maintained in Minimum Essential Medium Eagle with Earl's Balanced Salt Solution (MEM/EBSS) (Hyclone) supplemented with 10% Fetal Bovine Serum (Atlanta Biologicals) and 1× Antibiotic/Antimycotic (Toku-e). Cells were grown to 90% confluence and passaged by splitting at a 1:5 ratio. Cells were incubated at 37° C., with 5% $CO_2$ atmosphere.

NIH 3T3 and CRE BAG 2 (murine tumor fibroblast) cell lines were obtained from the American Type Culture Collection (Manassas, Va.). Cells were maintained in Dulbecco's Modified Eagles Medium (DMEM) (Sigma) supplemented with 10% Fetal Bovine Serum (Gibco) and 1× Antibiotic/Antimycotic (Gibco). Cells were grown to 70% confluence and passaged by splitting at a 1:10 ratio. Cells were incubated at 37° C. with 5% $CO_2$ atmosphere.

All cell lines were routinely monitored for cell viability using Live:Dead propidium iodide:CFDA staining; cells were deemed viable if >95% are PI-negative, and mycoplasma contamination via Hoechst staining and fluorescent microscope visual examination. Cells were considered mycoplasma-free when Hoechst staining was confined only to the cell nucleus and no staining was found in the cytosol.

Example 18: Preparation of a Pharmacological Solution or Pharmacological Composition for Treatment of Human Disease Model Cell Systems Targeted pharmacological chaperones were prepared as 10 mM stock solutions in $H_2O$ with 1% triethylamine. Prior to treatment of cells this stock was diluted in the media appropriate to the cell type to the concentrations being studied.

Example 19: Analysis of Enzyme Activity in Acidic Organelles in Live Human Immortalized Cell Lines Human immortalized B-Lymphocytes from Lysosomal Storage Disease patients (Metachromatic Leukodystrophy, Mucopolysaccaridosis type VI, Sly Syndrome, and Gaucher diseases) and healthy donors were obtained from the Coriell Institute for Medical Research (Camden, N.J.). Cell lines were maintained in RPMI 1640 Medium (HyClone) supplemented with 10% Fetal Bovine Serum (Atlanta Biologicals) and 1× Antibiotic/Antimycotic (Toku-e). Cells were maintained at a density between 2 and $5 \times 10^5$ cells/mL, cells were passed by dilution into fresh media. Cells were incubated at 37° C., with 5% $CO_2$ atmosphere.

Prior to analysis, cells were counted and seeded in round bottom 96 well plates at $1 \times 10^6$ cells/mL, 50 uL of cell suspension per well. The labeling solution containing appropriate substrates for the enzyme being analyzed (M1903, M1359, or M2365) in serum free media was added to the cells. 50 uL per well at 2× concentration and incubated at 37° C. for 16 to 24 hours. Additional serum free media (50 uL) containing 3 µM DRAQ7 (Biostatus) added and cells incubated for 5 minutes (37° C.). Fluorescence of viable cells was then measured by flow cytometry using a BD Accuri™ C6 Flow Cytometer, using the FL4 (DRAQ7) channel to remove dead cell information.

Example 20: Measurement of Lysosomal Enzyme and Chromatin Levels in Living Cells Using an Additional Detection Reagent Cells were prepared according to Example 17 with the exception that the cells were plated at $1 \times 10^5$ cells/mL in optical bottomed plates (Thermo Scientific/Nunc 165305). After the initial staining period, 100 uL per well of Opti-Klear™ Imaging Buffer containing 1 ug/mL of Hoechst 33342 was added and cells incubated for 10 minutes. Cells were examined under a fluorescence microscope equipped with appropriate filter sets for both the substrate and Hoechst dyes, such as DAPI and GFP. As both dyes are organelle-specific, the lysosomes and other acidic organelles were stained a bright fluorescent green when using a fluorescein based substrate, while the nuclei are simultaneously stained fluorescent blue. For resorufin-based substrates (red fluorescence) a DAPI/Texas Red filter set combination are employed. For longer wavelength substrates, the CY5/DAPI or CY7/DAPI filter sets are employed.

Example 21: Increasing Lysosomal β-Glucosidase Enzyme Activity in Normal and Gaucher Type-I, Type-II and Type-III Disease Human Leukocytes with the Addition of a Targeted Pharmacological Chaperone (TPC)

Cells from Gaucher I (GM10870). Gaucher II (GM08752). Gaucher III (GM01769) patients and apparently healthy donor cells (GM14643) were plated as example 19. Complete media containing the TPC was added to the cells to give a final TPC concentration of 25, 50 or 100 µM. Cells were incubated for 2 days at 37° C., 5% $CO_2$. After incubation, serum free media containing a lysosome-targeted β-glucosidase substrate (M1903. Marker Gene Technologies, Inc., Eugene, Oreg.) was added to the cells at a final concentration of 5 µM and the cells were incubated for a further 16 hours. Serum free media (50 uL) containing DRAQ7 (BioStatus, Leicestershire. England) was added to a final concentration of 3 µM and incubated at 37° C. for 5 minutes. Fluorescence of viable cells was recorded on a flow cytometer. Activity was measured based on percentage increase over untreated controls. FIG. 8 shows a representative experiment where Gaucher I (GM10870) cells were treated for 2 days prior to addition of targeted fluorescent β-glucosidase substrate at 5 uM final concentration while maintaining TPC treatment and incubated overnight. Prior to analysis DRAQ7 was added to a final concentration of 3 uM. 10000 live cell events were then captured in triplicate for each treatment on a BD Accuri C6 flow cytometer and median fluorescence was calculated as a percentage of normal activity, averaged and plotted.

Example 22: Increasing Lysosomal β-Glucuronidase Enzyme Activity in Normal and Human Leukocytes from Sly Syndrome Patients with the Addition of a Targeted Pharmacological Chaperone (PC)

Cells from Sly Syndrome patients and apparently healthy donor cells (GM14643) are plated as example 21. Complete media containing the appropriate TPC is added to the cells to give a final TPC concentration of 25, 50 or 100 µM. Cells are incubated for 2 days at 37° C. 5% $CO_2$. After incubation, the lysosomal-targeted β-glucuronidase substrate M2365 is added to the cells to give a final concentration of 1 µM and the cells are incubated for a further 16 hours. Cells are centrifuged at 200×g for 5 minutes and staining media removed. Cells are resuspended in 100 uL of PBS containing 1.5 µM DRAQ7 and incubated at 37° C. for 5 minutes Fluorescence of viable cells is recorded on a flow cytometer. Activity is measured based on percentage increase over untreated controls.

Example 23: Increasing Lysosomal β-Glucosidase Enzyme Activity in Gaucher Type-I, Type-II and Type-III Disease Human Leukocytes Models with the Addition of a Targeted Pharmacological Chaperone (TPC) in Combination with Enzyme Replacement Therapy (Cerezyme)

45 µM Cerezyme and 50 µM TPC are incubated together in PBS, pH 7.4 for 24 hours at 37° C. Cells from Gaucher I (GM10870). Gaucher II (GM08752), Gaucher III (GM01769) patients and apparently healthy donor cells (GM14643) are plated as example 21. Complete media containing the TPC/Cerezyme mixture, the TPC alone (50 μM) or Cerezyme alone (45 μM) is added to the cells. Cells are incubated for 2 days at 37° C. 5% $CO_2$. After incubation, the substrate M1903 is added to the cells to give a final concentration of 5 μM and the cells are incubated for a further 16 hours. Serum free media containing DRAQ7 (BioStatus, Leicestershire, England) is added to a final concentration of 3 uM and incubated at 37° C. for 5 minutes. Fluorescence of viable cells is recorded on a BD Accuri™ C6 flow cytometer. Activity is measured based on percentage increase over untreated controls.

Example 24: Staining and Analysis of Targeted Pharmacological Chaperone (PC) Activity in Metachromatic Leukodystrophy (MLD) and Mucopolysaccaridosis Type VI Model Adherent Cell Lines Cells from Metachromatic Leukodystrophy (MLD) and Mucopolysaccaridosis type VI patients (GM00243 and GM00519 respectively) and apparently healthy donor cells (GM14643) Coriell Institute and are plated as Example 20. Complete media containing the TPC is added to the cells to give a final TPC concentration of 25, 50 or 100 μM. Cells are incubated for 2 days at 37° C., 5% $CO_2$. After incubation, the lysosomal-targeted arylsulfatase substrate M359 is added to the cells to give a final concentration of 100 μM and the cells are incubated for a further 16 hours. The staining media is then removed, the cells washed in PBS and 100 uL per well of Opti-Klear™ Cell Imaging Buffer (Marker Gene Technologies, Inc, Eugene, Oreg.) containing 1 mg/mL Hoeschst 33342 is added and the cells incubated for 10 mins at 37° C. The cells are then photographed using a Zeiss AxioObserver A1 epifluorescence inverted microscope equipped with an QiClick ICX285 CMOS CCD digital camera (QImaging, Surrey. BC, Canada) using an appropriate filter set for the fluorophore used. The cells are also imaged using the EVOS Auto-FL automated live-cell imaging system (Life Technologies, Carlsbad, Calif.) using appropriate filter sets for the fluorophore used in staining. Results were digitized and interpreted using CellProfiler™ cell imaging analysis software (Broad Institute, MIT; http://www.cellprofiler.org/) or Acapella High Content Analysis Software package. Activity was measured based on percentage increase over untreated controls.

Example 25: TLC Analysis of the Clearance of Excess Glycolipids in Patient Samples Using the Targeted Pharmacological Chaperones A series of targeted pharmacological chaperone derivatives were compared for their abilities to affect glycolipid biosynthesis by 1D-TLC. The non-targeted imino sugar miglustat exhibited a moderate effect on glycolipid biosynthesis. The targeted pharmacological chaperone analogues of the iminosugars (e.g. M2091, M2092, etc.) exhibited the ability to help clear the buildup of excess glycolipids in the cell activity, as determined by the decrease of detectable Glc-Cer and allied glycolipids to near the levels found in normal cells (see FIG. 9). These data were in agreement with the data from the scientific literature.

The in vitro Gaucher's disease models were prepared as follows: Gaucher II (G325R/C342G) fibroblast cells GM02627 and normal human skin fibroblast cells AG06173 (American Type Culture Collection, Rockville, Md., U.S.A.) were maintained in logarithmic phase growth for 15 days in RPMI-1640 medium. 10% FCS. Primary Human Fibroblasts from Gaucher I (F0361999) patients were obtained from Istituto Giannina Gaslini (Genova, Italy). Primary Human Fibroblasts from a healthy donor (AG06173) and Gaucher I (GM00372A) patients were obtained from the Coriell Institute for Medical Research (Camden, N.J.). Cells were cultured in Minimum Essential Medium Eagle supplemented with 10% FCS.

Immortalized B-lymphocytes from healthy donor (GM14643), Gaucher I (GM10870, GM10874), and Gaucher II (GM08752) patients were obtained from the Coriell Institute for Medical Research. Cells were cultured in RPMI 1640 medium supplemented with 10% FCS humidified at 37° C. with 5% $CO_2$(g) and monitored for viability (trypan blue staining, TC-10 Bio-Rad Automated Cell Counter).

Cell labeling solutions were prepared by diluting substrate stock solutions in the appropriate medium for the cell line (see above) without serum. TPC treatment solutions were prepared by diluting stock solutions in complete media appropriate for the cell line. Cells were treated with either the targeted pharmacological chaperones (10 uM final concentration), miglustat (10 uM) or no drug (control) for 3 days prior to all analyses. For lipid analyses cells were counted on a TC-10 Automated Cell Counter (Bio-Rad, Hercules, Calif.) harvested by centrifugation (800×g, 5 min.) and subjected to one PBS wash (i mL per sample) and centrifugation as above. The resulting pellets were weighed and 20 volumes of 2:1 chloroform:methanol added. These samples were then incubated overnight at room temperature with mild rotation. The resulting solutions were centrifuged and organic layer decanted before addition of 5 volumes of 1:1 chloroform:methanol and incubation for an additional 2 hours at room temperature with mild stirring. The solutions were centrifuged and upper supernatant organic layers decanted. The combined organic extracts for each sample were combined and the chloroform concentration adjusted to 2:1. Then 0.2 volumes of 0.88% potassium chloride added and the tubes mixed thoroughly by vortex mixing. The tubes were allowed to settle and centrifuged (800×g, 5 min.) and the upper aqueous layer removed.

The final lower layers containing total glycolipids were spotted on silicagel G plates (EMD Merck, Darmstadt, Germany) in volumes relative to the initial cell counts and eluted in 6:4:1 chloroform:methanol:water. Plates were visualized using either orcinol or 5% sulfuric acid/ethanol stains prior to imaging and analysis. The resulting images were analyzed using ImageJ software (National Institutes of Health, Bethesda, Md.) to calculate the relative density of each band. FIG. 9 shows representative data from 6 trials in which cells were subjected to treatment with TPCs for 3 days then harvested and glycolipids extracted using the method similar to Hildebrand, et al., (Hildebrand J, Stryckmans P, Stoffyn P. (1971) "Neutral glycolipids in leukemic and nonleukemic leukocytes" J. Lipid Res. 12(3):361-366). The isolated lipids were subjected to analysis by TLC followed by staining with either orcinol or sulfuric acid/ethanol and analyzed using ImageJ image analysis software to estimate the relative density of each band.

Example 26: Demonstration of TPC Binding to a Human Recombinant Beta-Glucoceramidase Enzyme (Cerezyme) by Thermal Shift Analysis Appropriate TPCs at a final concentration of 10 uM were combined with 0.1 ug of purified human recombinant beta- Glucoceramidase enzyme (Cerezyme) and the protein binding dye Sypro Orange® at a final concentration of 1× in citrate buffer at pH7.0. The reaction was then exposed to a temperature gradient from 30-95° C. in an Applied Bioscience StepOne™ real time PCR instrument with temperature incrementing 0.2° C. every 11 seconds for a total running time of 1 hour. The resulting fluorescence was plotted and the shift in temperature at which fluorescence increased calculated. Treatment with the compounds showed an increase in denaturation temperature of 2-4° C. A representative experiment is shown in FIG. 12 where 0.1 ug of purified GCase was combined with 10 uM TPC and 5×SYPRO® Orange in citrate buffer at pH7.0. Each condition was performed in triplicate and subjected to a melt curve with 0.2° C. increments over 1 hour in Applied Biosystems StepOne Real-Time PCR instrument. The resultant data was averaged, normalized to the baseline and plotted Example 27: Measurement of Reduction in Lysosomal Burden on TPC Treatment by Staining with LysoTracker™ Green Fibroblasts and B-lymphocytes from healthy (AGO6173 and GM14643, respectively), fibroblasts from a Gaucher type II patient (GM0627) and B-Lymphocytes from a Gaucher type I patient (GM10780) were cultured for 3 days in complete RPMI-1640 media either with or without targeted pharmacological chaperone compounds at concentrations of 10 and 30 uM. After the 3 day incubation, the culture media was removed and replaced with PBS containing 200 nM Lysotracker™ Green and the cells incubated at 37° C. and 5% $CO_2$ for 1 hour. Fibroblast cells were subjected to image analysis by first imaging on an AMG EVOS Auto FL microscope and then digitally analyzing the fluorescence accumulation in lysosomes using Cell Profiler image analysis software (Broad Institute, MIT). Lymphocyte cells were resuspending in Opti-Klear™ Flow Holding buffer containing DRAQ7™ dead cell indicator (BioStatus, Leicestershire, UK) capturing 10000 singlet live cell events using a BD Accuri C6 flow cytometer and the mean fluorescence signal for each sample was compared. Treatment with compounds showed up to an 80% decrease in lysosomal burden as shown in FIG. 10.

Example 28: Therapeutic Treatment of Patients

In treatment of the recipient patients in accordance with the method of the invention, the active agent or agents can be administered by conventional drug administration procedures, preferably in formulations with pharmaceutically acceptable diluents and carriers. The active agent or agents can be used in the free amine form or in a salt form. Pharmaceutically acceptable salt forms are illustrated, for example, by the HCl, HOAc or HBr salts.

The amount of active agent to be administered must be an effective amount, that is, an amount which will be medically beneficial but does not present toxic effects which outweigh the advantages which accompany its use. It would be expected that the average adult human daily dosage would normally range from about 0.1 mg to about 1000 mg of the active agent. Dosages will be adjusted for combination therapy methods with active enzyme, for combined TPC-ERT. The preferable route of administration is orally in the form of capsules, tablets, syrups, elixirs and the like, although parenteral administration methods such as intravenous, intramuscular, intraparenteral, subcutaneous, transdermal, airway (aerosol), rectal, topical (including buccal and sublingual) or intrathecal injection can also be used. Suitable formulations of the active compound in pharmaceutically acceptable diluents and carriers in therapeutic dosage form can be prepared by conventional procedures such as by reference to general texts in the field, e.g., Remington's Pharmaceutical Sciences, ed. Arthur Osol, 16th ed., 1980, Mack Publishing Co., Easton, Pa., and the 18th ed., 1990. Conventional diluents and carriers are, e.g., water, normal saline, sugars, starch and the like substances.

The effectiveness of any composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, or the like. The guidelines known in the medical art may be used to optimize the treatment. e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices as described above for analysis of the enzyme activity in biopsy samples (adherent cells) or from blood samples and measurement of changes in enzyme activity in patient leukocytes, at predetermined times during the treatment period. Treatment, including compositions, amounts, times of administration and formulations, may be optimized according to the results of such monitoring. The patient may be periodically reevaluated to determine the extent of improvement by measuring the same parameters. Adjustments to the amount(s) and composition(s) of the therapeutic chemical chaperones of the invention administered and possibly the duration of administration may be made based on these reevaluations.

Treatment may be initiated with smaller dosages which are less than the optimum dose of the compound. Thereafter, the dosage may be increased by small increments until the optimum therapeutic effect is attained.

The use of the determined compositions may reduce the required dosage for any individual agent contained in the compositions (e.g., the active enzyme in enzyme replacement therapies (ERT)) because the onset and duration of effect of the different individual agents may be complimentary.

Toxicity and therapeutic efficacy of subject compositions may be determined by standard pharmaceutical procedures in cell cultures or experimental animals, e.g., for determining the individual $LD_{50}$ and the $ED_{50}$ values for any specific TPC agent.

The data obtained from the cell culture assays and animal studies may be used in formulating a range of dosage values for use in humans. The dosage of any subject composition lies preferably within a range of circulating concentrations and bioavailability levels that include the $ED_{50}$ with little or no toxicity. The dosage may vary within this range depending upon the dosage form employed and the route of administration utilized. For compositions of the present invention, the therapeutically effective dose may be estimated initially from cell culture assays, as have been described herein.

Various other examples will be apparent to the person skilled in the art after reading the disclosure herein. All such other examples are meant to be included within the scope of the appended claims.

It is to be understood that, while the foregoing invention has been described in detail by way of illustration and example, numerous modifications, substitutions, and alterations are possible without departing from the spirit and scope of the invention as described in the following claims.

```
                            SEQUENCE LISTING

<160> NUMBER OF SEQ ID NOS: 25

<210> SEQ ID NO 1
<211> LENGTH: 7
<212> TYPE: PRT
<213> ORGANISM: Artificial Sequence
<220> FEATURE:
<223> OTHER INFORMATION: Targeting Sequence

<400> SEQUENCE: 1

Pro Lys Lys Lys Arg Lys Val
1               5

<210> SEQ ID NO 2
<211> LENGTH: 4
<212> TYPE: PRT
<213> ORGANISM: Artificial Sequence
<220> FEATURE:
<223> OTHER INFORMATION: Targeting Sequence 2

<400> SEQUENCE: 2

Lys Asp Glu Leu
1

<210> SEQ ID NO 3
<211> LENGTH: 7
<212> TYPE: PRT
<213> ORGANISM: Artificial Sequence
<220> FEATURE:
<223> OTHER INFORMATION: Targeting Sequence 3

<400> SEQUENCE: 3

Cys Lys Gly Gly Ala Lys Leu
1               5

<210> SEQ ID NO 4
<211> LENGTH: 11
<212> TYPE: PRT
<213> ORGANISM: Artificial Sequence
<220> FEATURE:
<223> OTHER INFORMATION: Targeting Sequence 4

<400> SEQUENCE: 4

Val Val Val Lys Lys Lys Arg Lys Val Val Cys
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Targeting Sequence 5

<400> SEQUENCE: 5

Cys Phe Phe Lys Asp Glu Leu
1               5
```

```
<210> SEQ ID NO 6
<211> LENGTH: 9
<212> TYPE: PRT
<213> ORGANISM: Artificial Sequence
<220> FEATURE:
<223> OTHER INFORMATION: Targeting Sequence 6

<400> SEQUENCE: 6

Gly Ala Ser Asp Tyr Gln Arg Leu Cys
1               5

<210> SEQ ID NO 7
<211> LENGTH: 7
<212> TYPE: PRT
<213> ORGANISM: Artificial Sequence
<220> FEATURE:
<223> OTHER INFORMATION: Targeting Sequence 7

<400> SEQUENCE: 7

Cys Ala His His Ala Glu Leu
1               5

<210> SEQ ID NO 8
<211> LENGTH: 7
<212> TYPE: PRT
<213> ORGANISM: Artificial Sequence
<220> FEATURE:
<223> OTHER INFORMATION: Targeting Sequence 8

<400> SEQUENCE: 8

Cys Ala Arg His Ala Glu Leu
1               5

<210> SEQ ID NO 9
<211> LENGTH: 7
<212> TYPE: PRT
<213> ORGANISM: Artificial Sequence
<220> FEATURE:
<223> OTHER INFORMATION: Targeting Sequence 9

<400> SEQUENCE: 9

Cys Pro Leu His Asn Glu Leu
1               5

<210> SEQ ID NO 10
<211> LENGTH: 7
<212> TYPE: PRT
<213> ORGANISM: Artificial Sequence
<220> FEATURE:
<223> OTHER INFORMATION: Targeting Sequence 10

<400> SEQUENCE: 10

Cys Glu Arg His Thr Glu Leu
1               5

<210> SEQ ID NO 11
<211> LENGTH: 7
<212> TYPE: PRT
<213> ORGANISM: Artificial Sequence
<220> FEATURE:
<223> OTHER INFORMATION: Targeting Sequence 11

<400> SEQUENCE: 11

Cys Thr Glu His Ile Glu Leu
1               5
```

```
<210> SEQ ID NO 12
<211> LENGTH: 7
<212> TYPE: PRT
<213> ORGANISM: Artificial Sequence
<220> FEATURE:
<223> OTHER INFORMATION: Targeting Sequence 12

<400> SEQUENCE: 12

Cys Thr Glu His Val Glu Leu
1               5

<210> SEQ ID NO 13
<211> LENGTH: 7
<212> TYPE: PRT
<213> ORGANISM: Artificial Sequence
<220> FEATURE:
<223> OTHER INFORMATION: Targeting Sequence 13

<400> SEQUENCE: 13

Ser Asp Tyr Gln Arg Leu Cys
1               5

<210> SEQ ID NO 14
<211> LENGTH: 7
<212> TYPE: PRT
<213> ORGANISM: Artificial Sequence
<220> FEATURE:
<223> OTHER INFORMATION: Targeting Sequence 14

<400> SEQUENCE: 14

Ala Asp Tyr Gln Arg Leu Cys
1               5

<210> SEQ ID NO 15
<211> LENGTH: 7
<212> TYPE: PRT
<213> ORGANISM: Artificial Sequence
<220> FEATURE:
<223> OTHER INFORMATION: Targeting Sequence 15

<400> SEQUENCE: 15

Ser Gly Tyr Gln Arg Leu Cys
1               5

<210> SEQ ID NO 16
<211> LENGTH: 7
<212> TYPE: PRT
<213> ORGANISM: Artificial Sequence
<220> FEATURE:
<223> OTHER INFORMATION: Targeting Sequence 16

<400> SEQUENCE: 16

Ala Ala Tyr Gln Arg Leu Cys
1               5

<210> SEQ ID NO 17
<211> LENGTH: 7
<212> TYPE: PRT
<213> ORGANISM: Artificial Sequence
<220> FEATURE:
<223> OTHER INFORMATION: Targeting Sequence 17

<400> SEQUENCE: 17

Ser Asp Tyr Glu Arg Leu Cys
1               5

<210> SEQ ID NO 18
```

```
<211> LENGTH: 7
<212> TYPE: PRT
<213> ORGANISM: Artificial Sequence
<220> FEATURE:
<223> OTHER INFORMATION: Targeting Sequence 18

<400> SEQUENCE: 18

Ser Asp Tyr Gln Arg Val Cys
1               5

<210> SEQ ID NO 19
<211> LENGTH: 11
<212> TYPE: PRT
<213> ORGANISM: Artificial Sequence
<220> FEATURE:
<223> OTHER INFORMATION: Targeting Sequence 19

<400> SEQUENCE: 19

Val Val Val Lys Lys Arg Arg Arg Val Val Cys
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Targeting Sequence 20

<400> SEQUENCE: 20

Val Val Val Lys Lys Lys Arg Lys Val Val Cys
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Targeting Sequence 21

<400> SEQUENCE: 21

Val Val Val Lys Lys Arg Lys Lys Val Val Cys
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Targeting Sequence 22

<400> SEQUENCE: 22

Cys Lys Gly Gly Tyr Gln Ser Lys Leu
1               5

<210> SEQ ID NO 23
<211> LENGTH: 9
<212> TYPE: PRT
<213> ORGANISM: Artificial Sequence
<220> FEATURE:
<223> OTHER INFORMATION: Targeting Sequence 23

<400> SEQUENCE: 23

Cys Lys Gly Gly Tyr Gln Ser Glu Leu
1               5

<210> SEQ ID NO 24
<211> LENGTH: 5
```

```
<212> TYPE: PRT
<213> ORGANISM: Artificial Sequence
<220> FEATURE:
<223> OTHER INFORMATION: Targeting Sequence 24

<400> SEQUENCE: 24

Lys Lys Lys Arg Lys
1               5

<210> SEQ ID NO 25
<211> LENGTH: 6
<212> TYPE: PRT
<213> ORGANISM: Artificial Sequence
<220> FEATURE:
<223> OTHER INFORMATION: Targeting Sequence 25

<400> SEQUENCE: 25

Ser Cys Tyr Gln Arg Leu
1               5
```

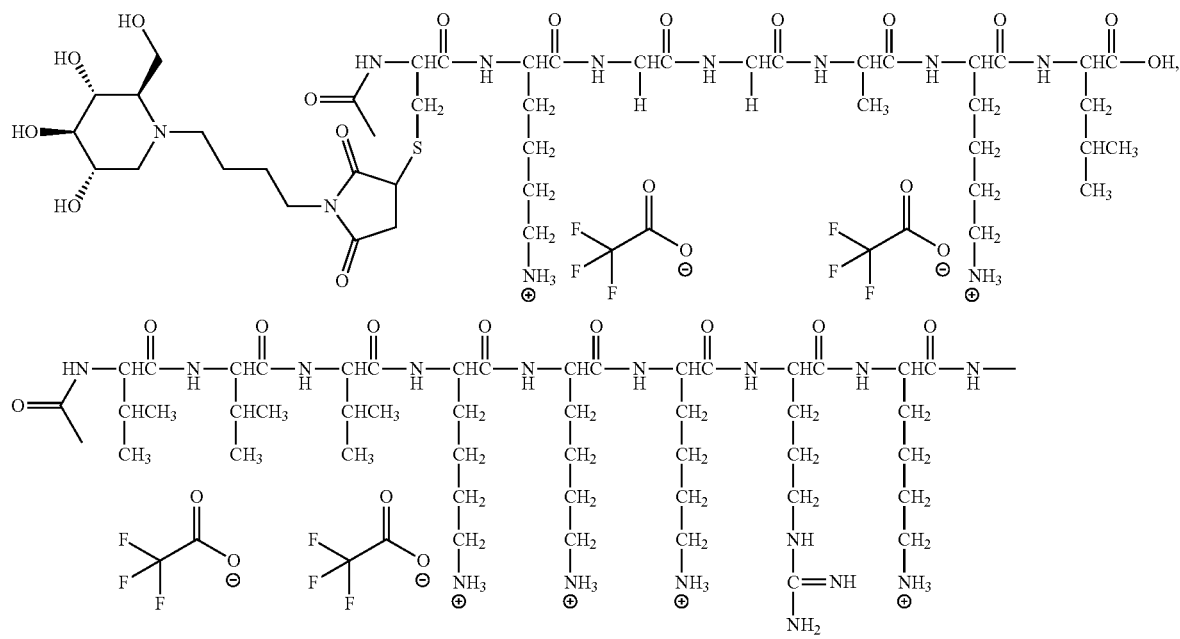

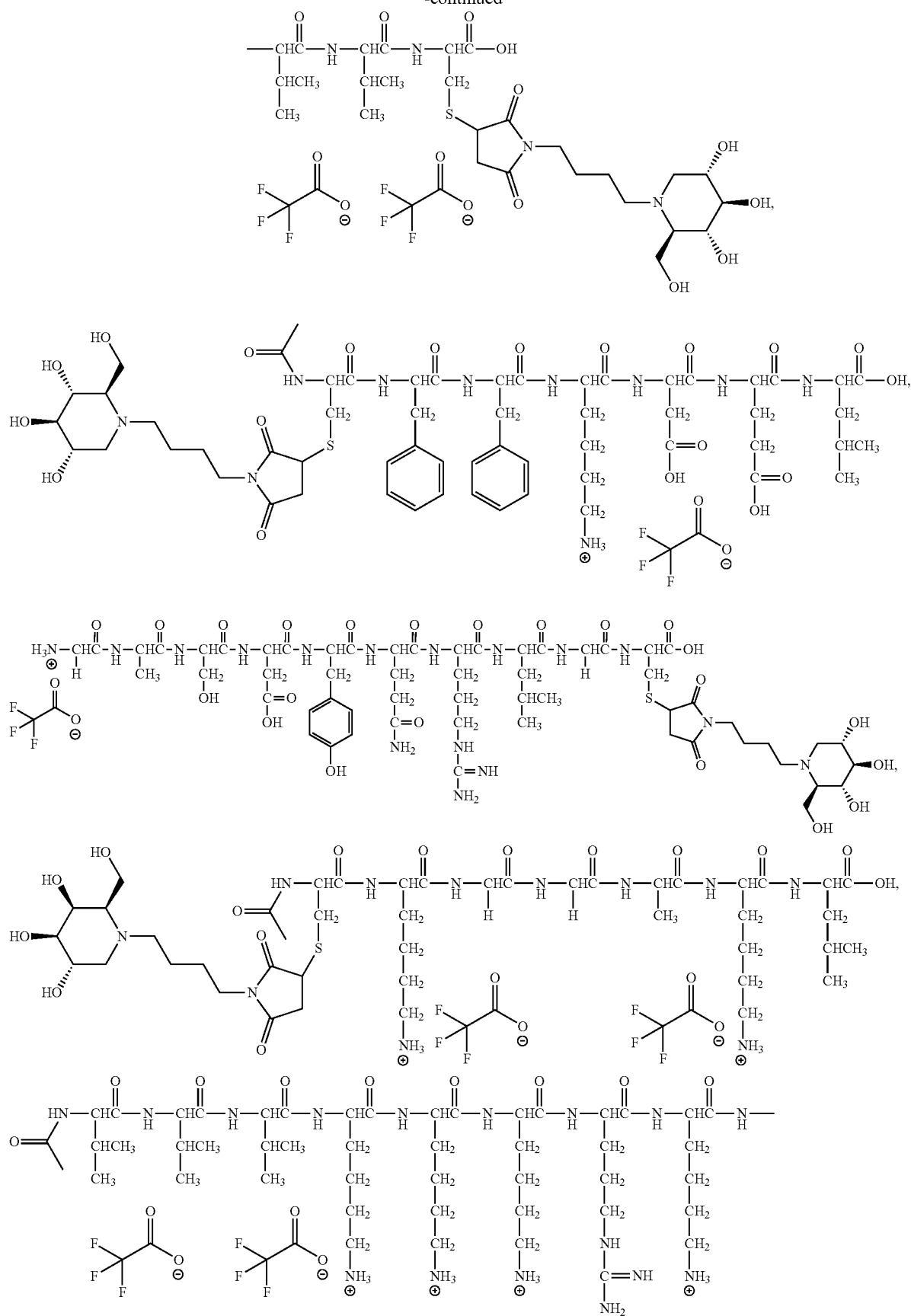

-continued
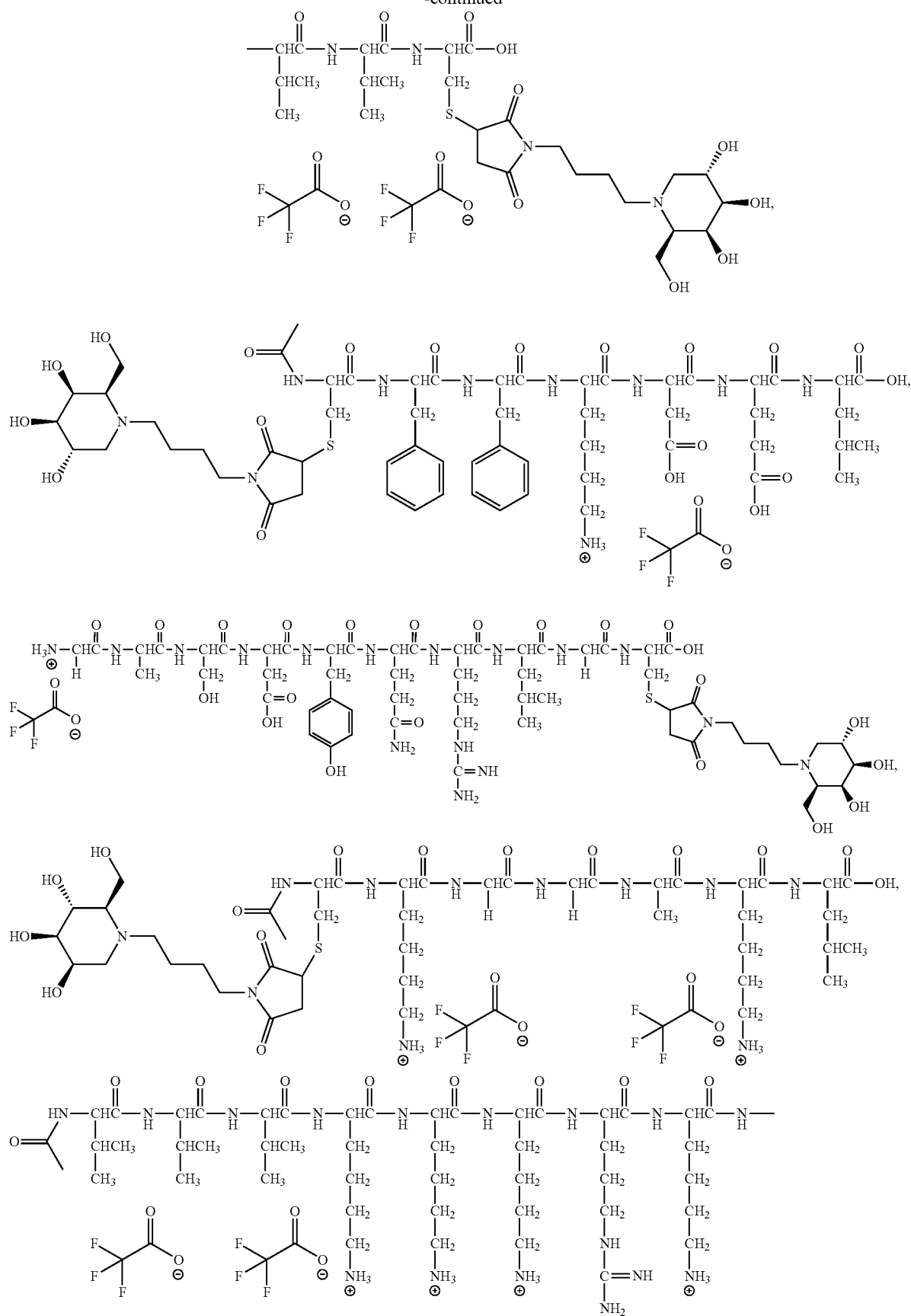

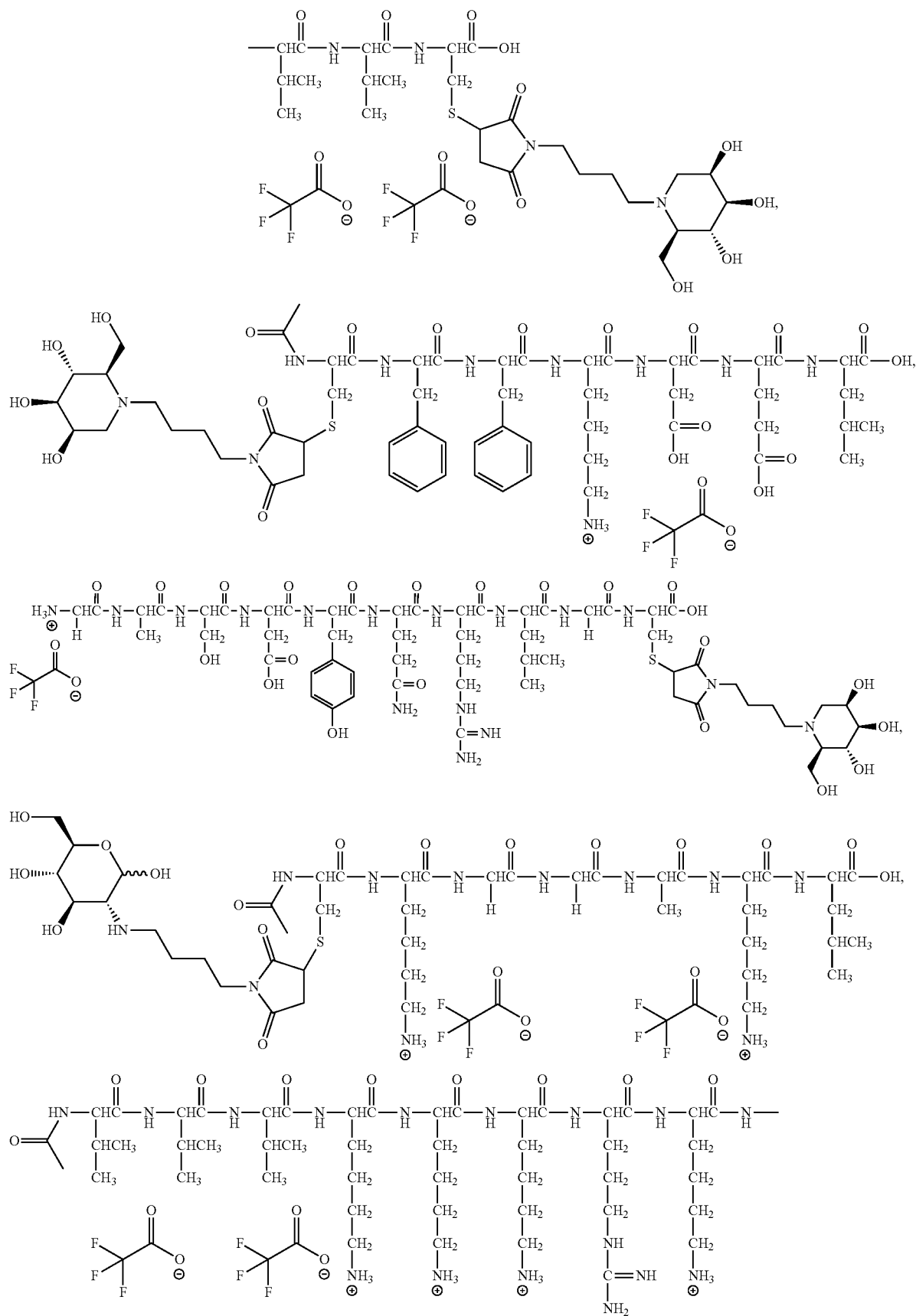

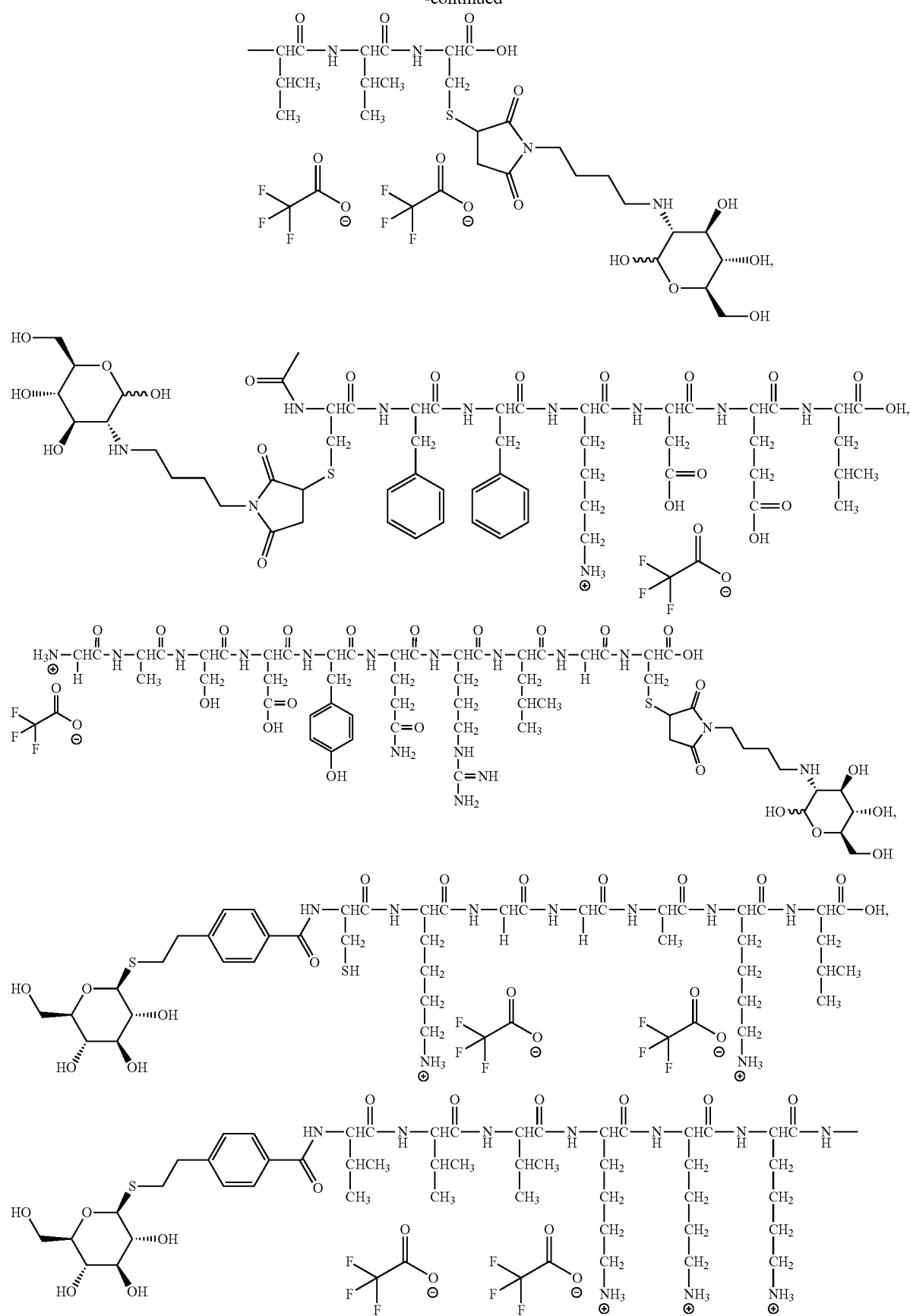

-continued
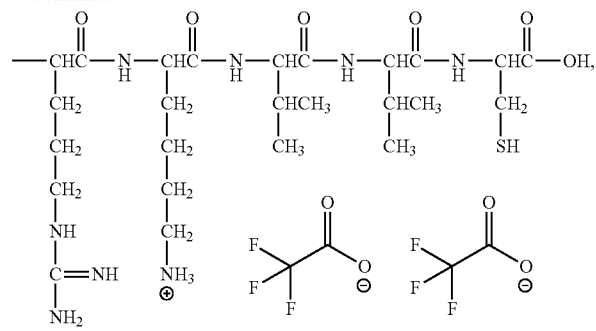
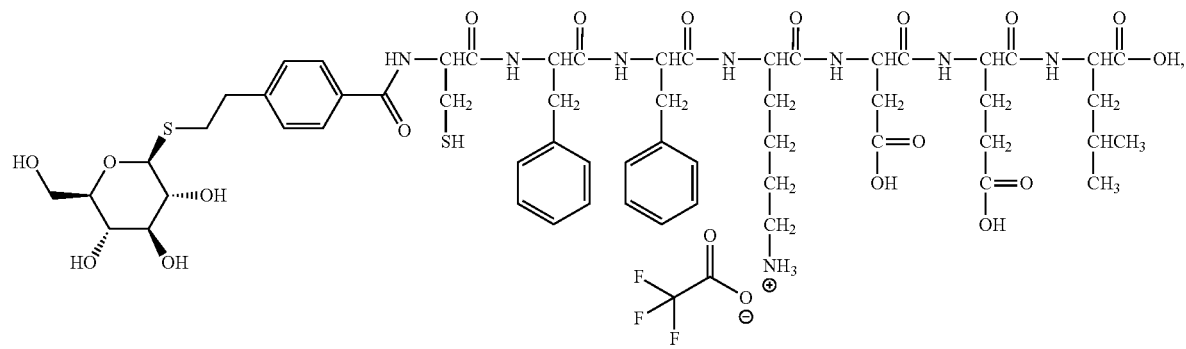
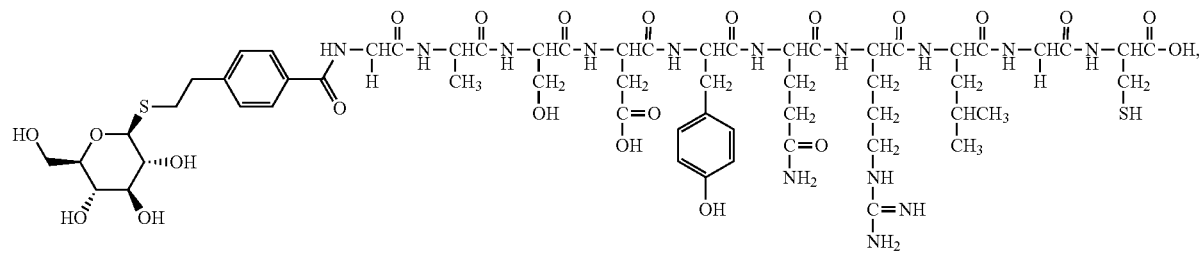
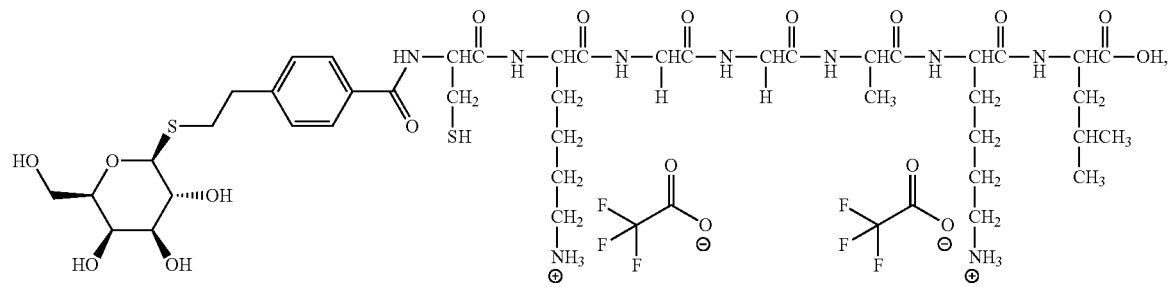
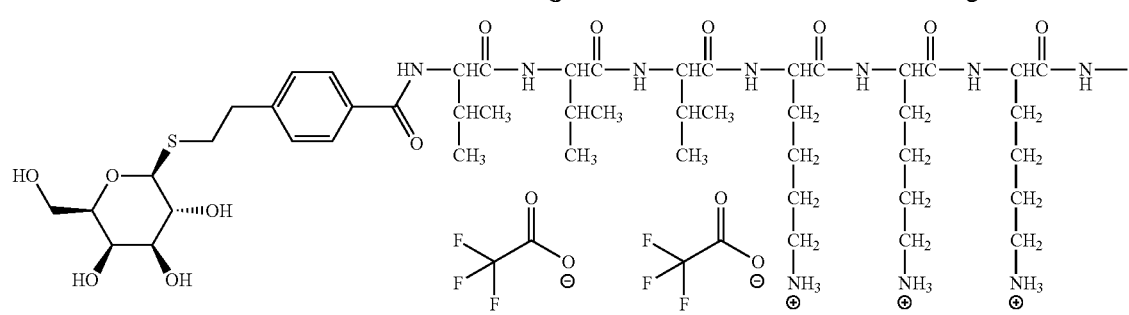

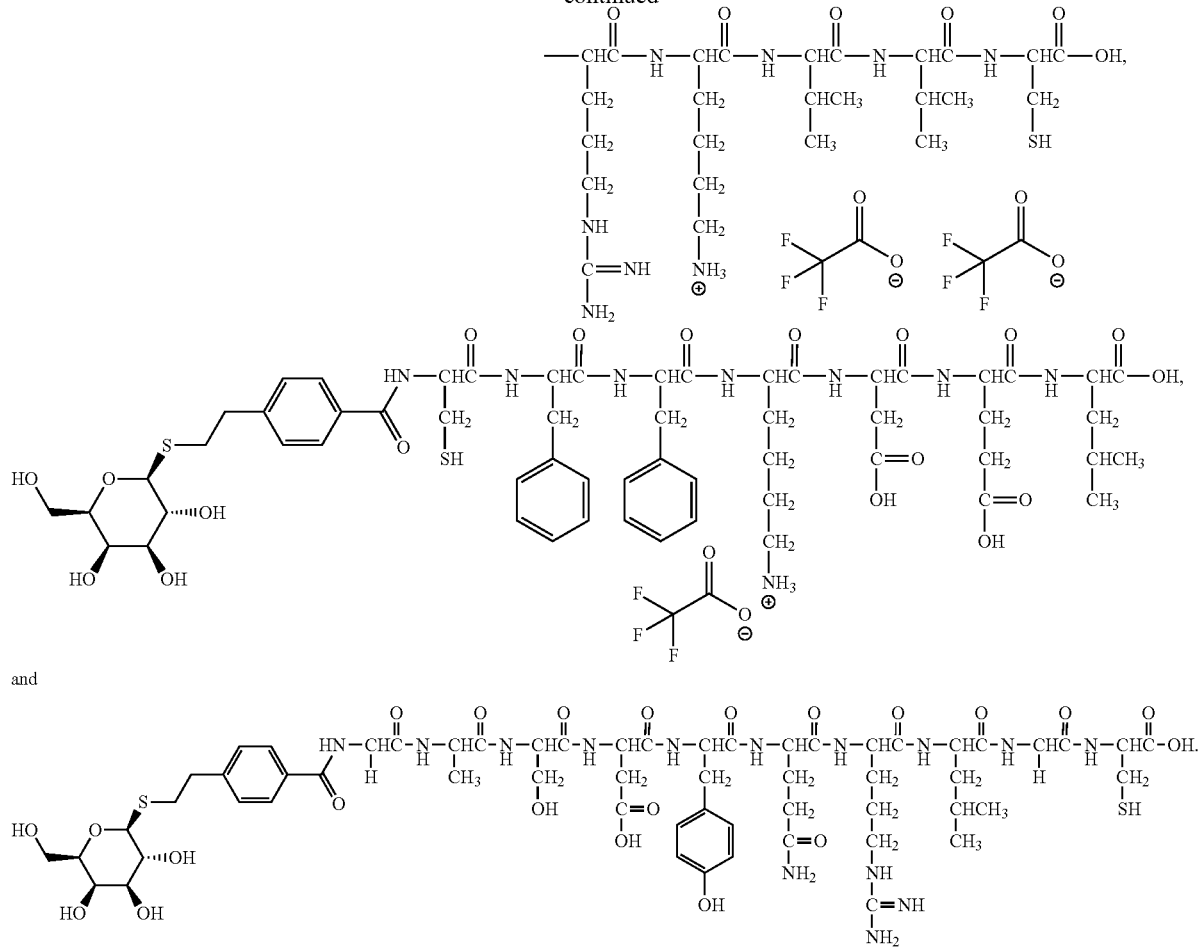

The invention claimed is:
1. A method of treating a lysosomal storage disease in a subject, comprising:
   A. preparing a targeted pharmacological chaperone having a formula selected from the group consisting of:

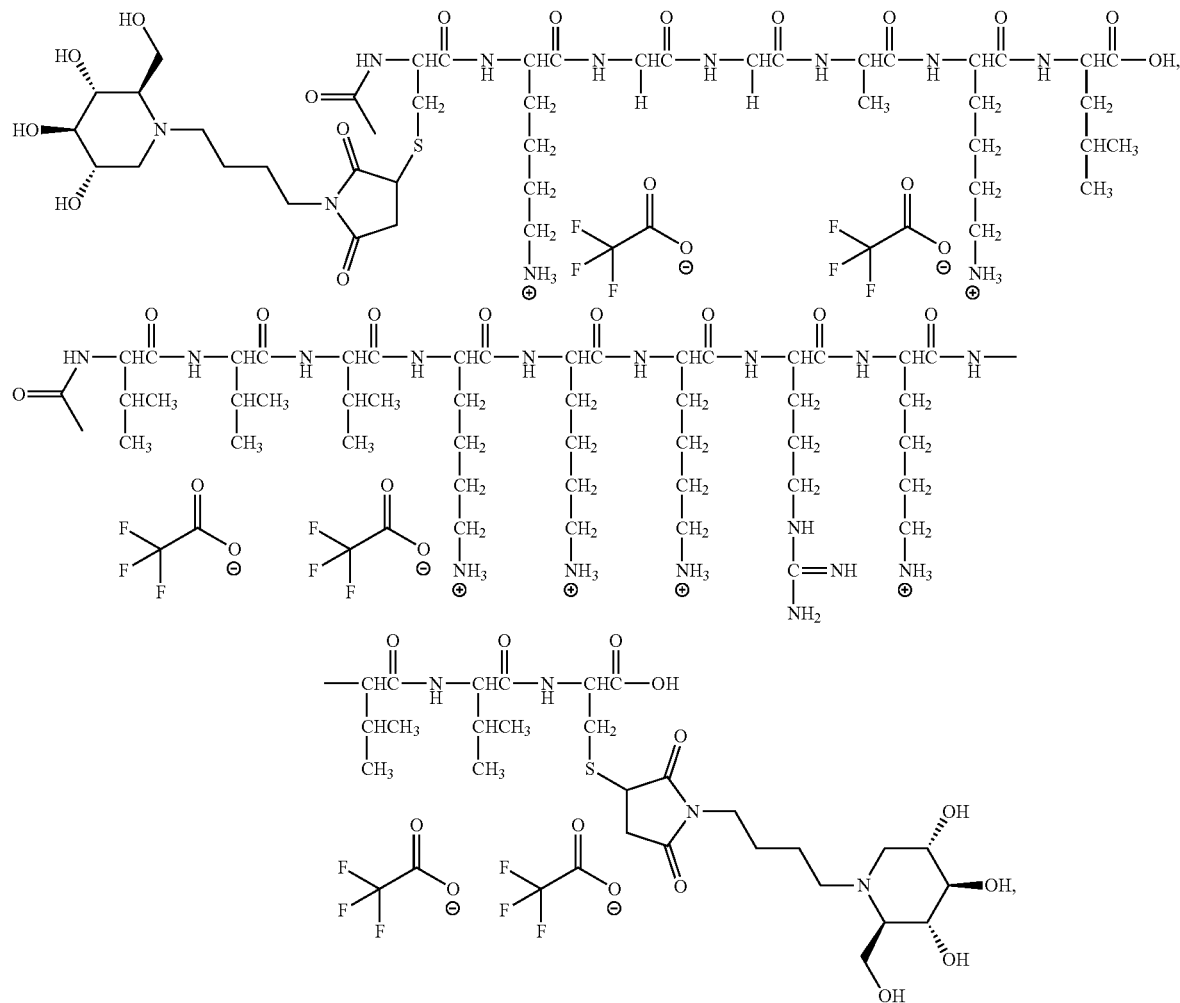

-continued
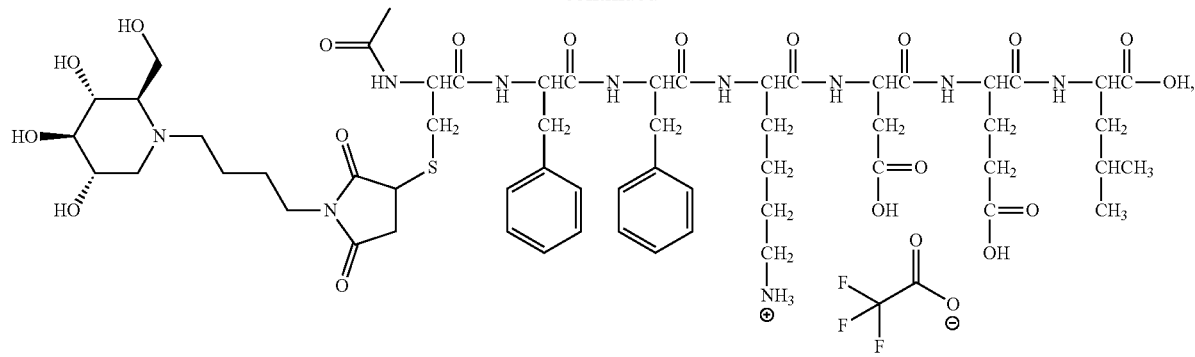
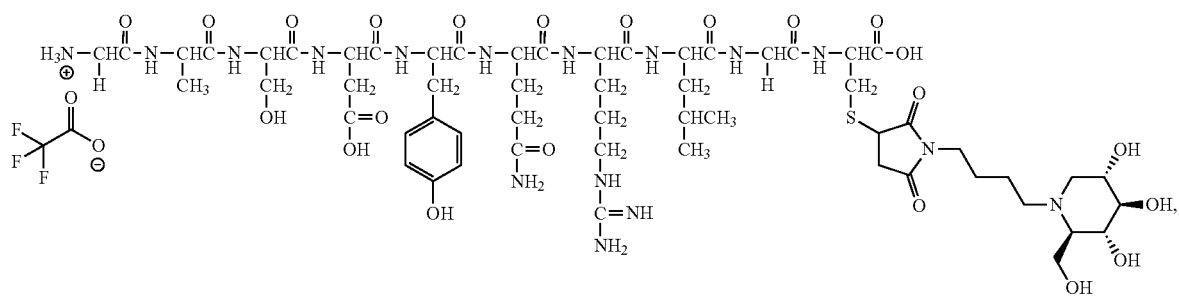
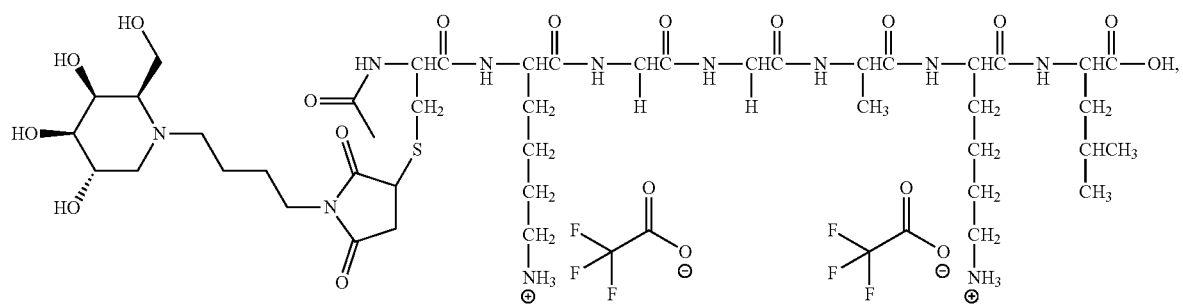
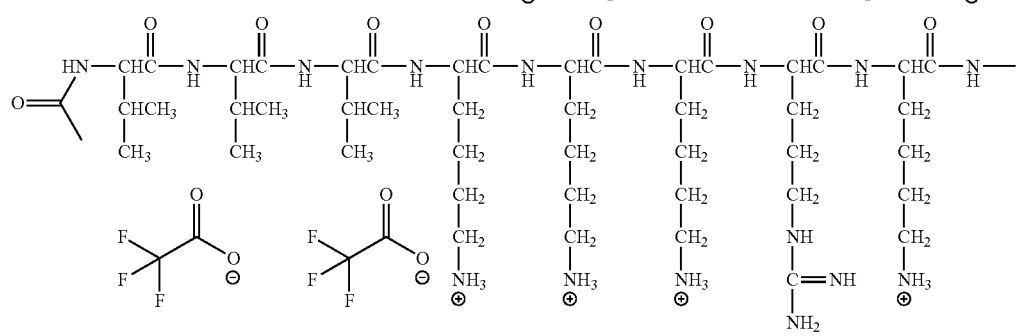
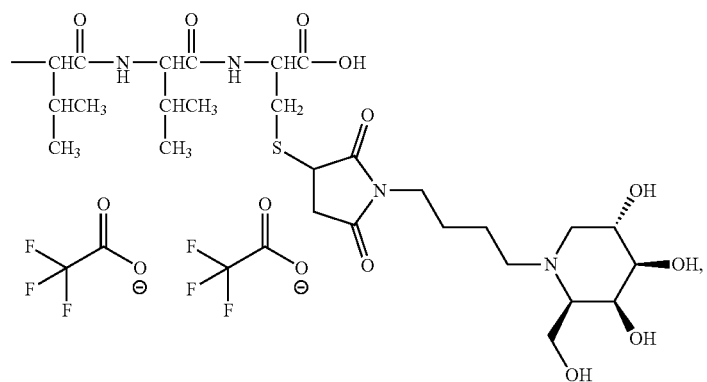

-continued
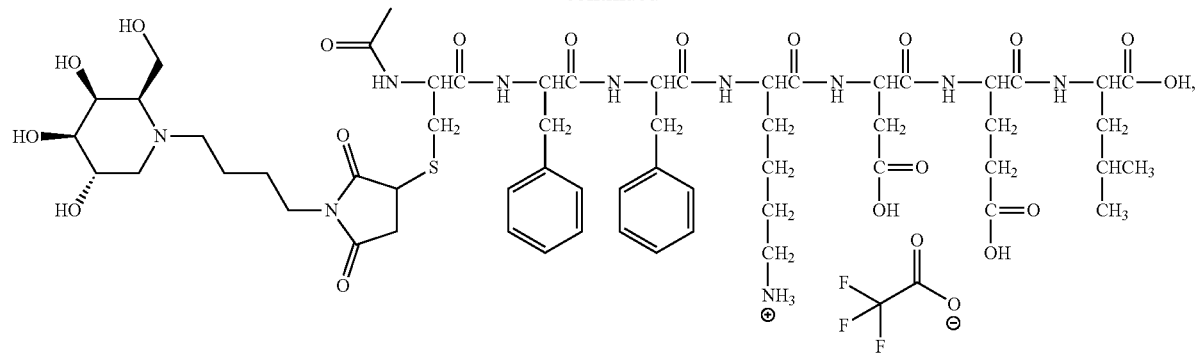
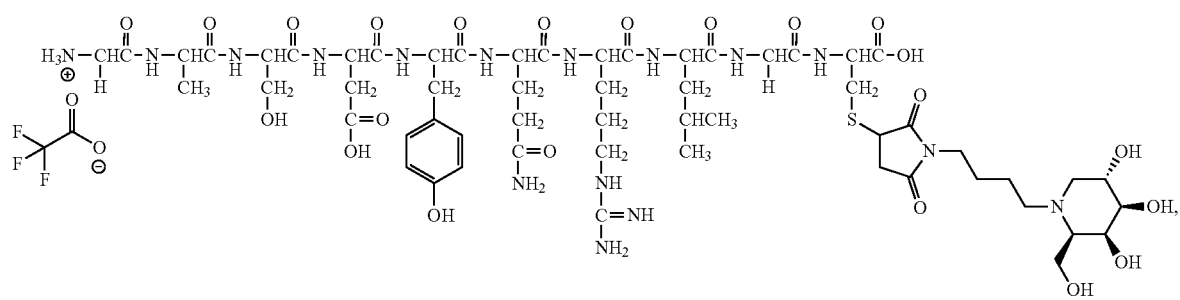
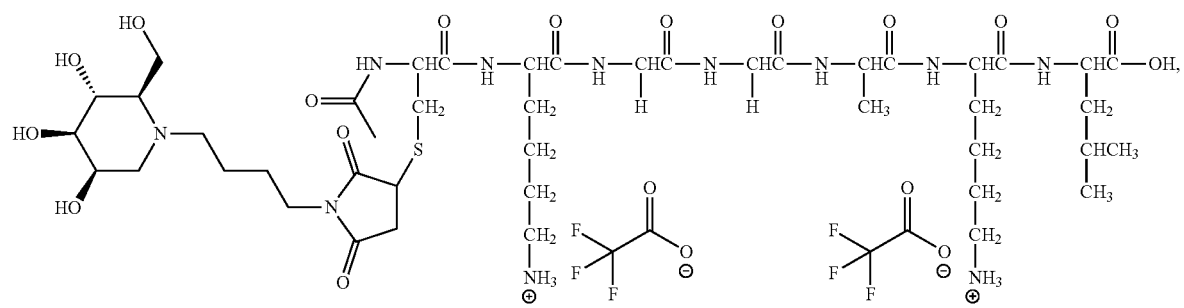
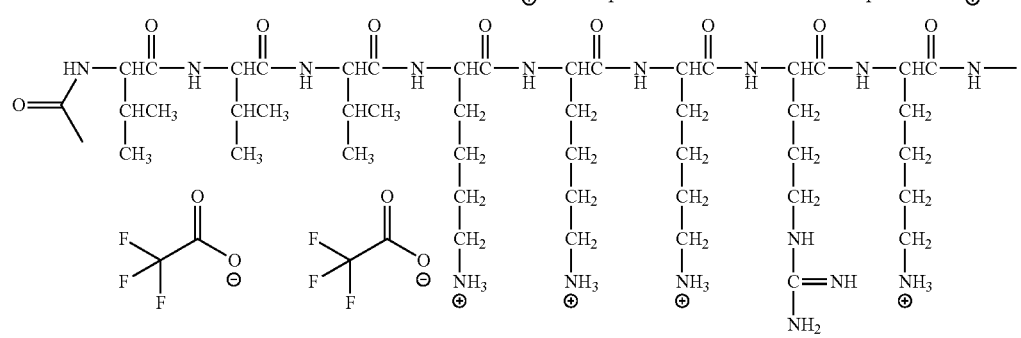
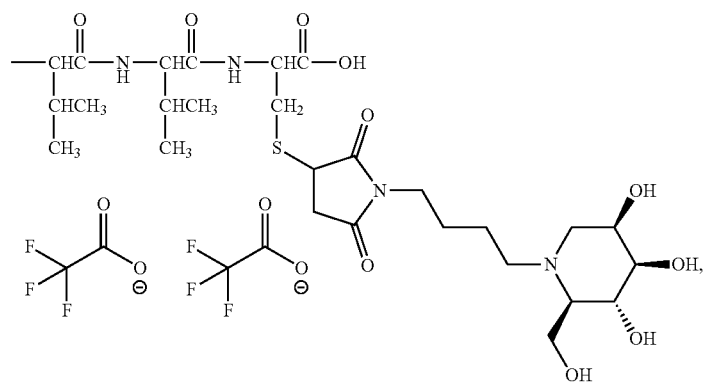

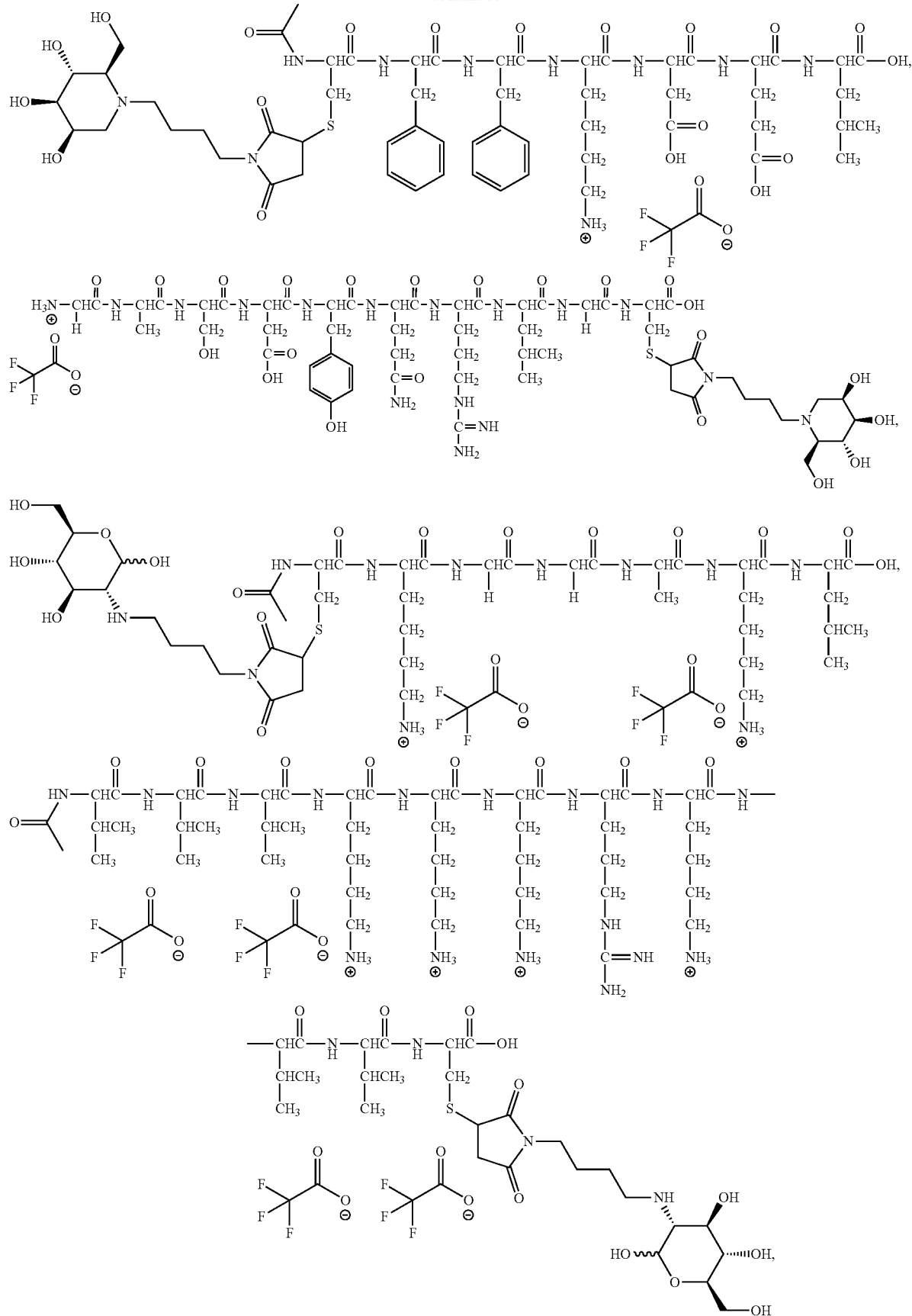

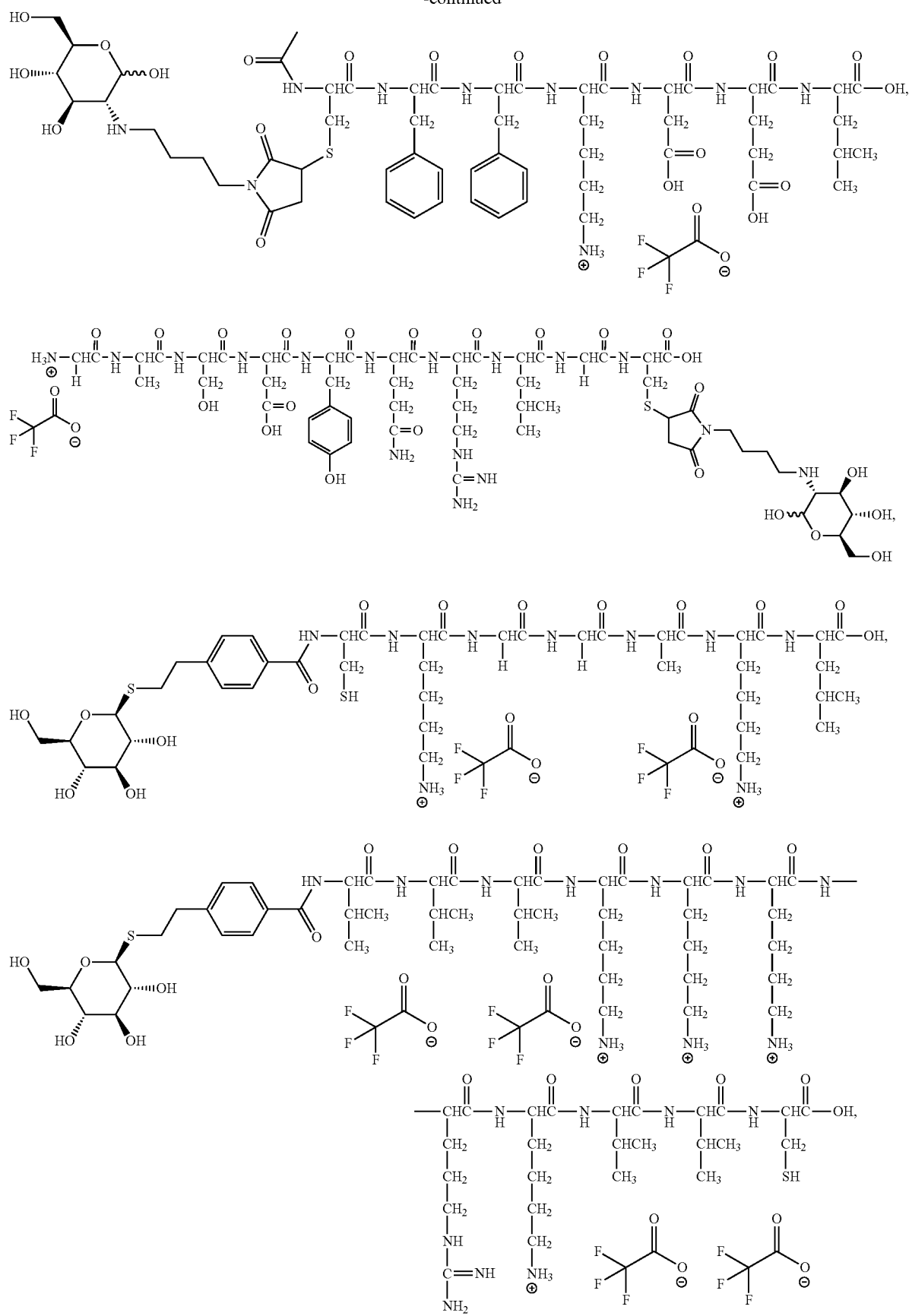

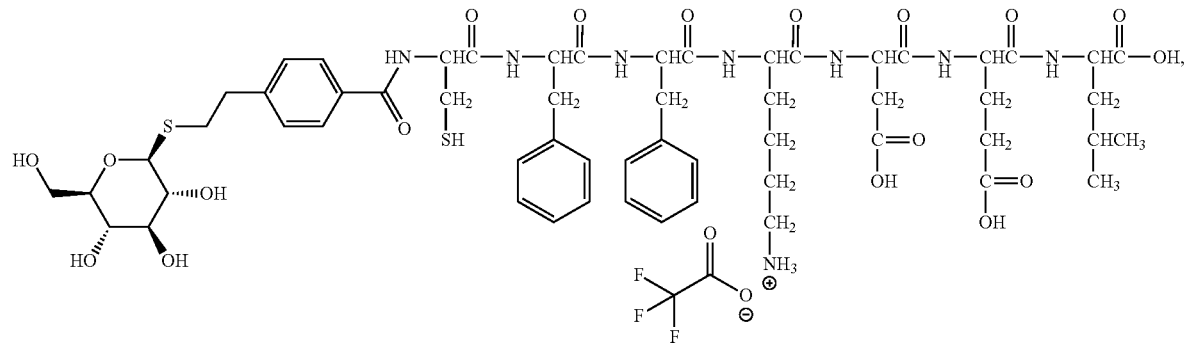
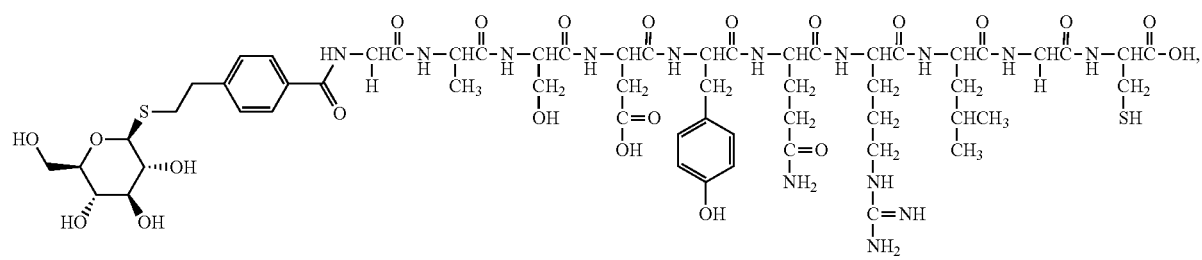
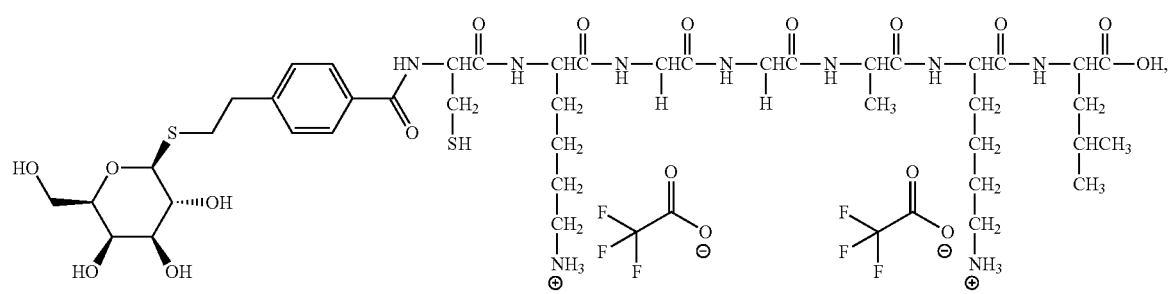
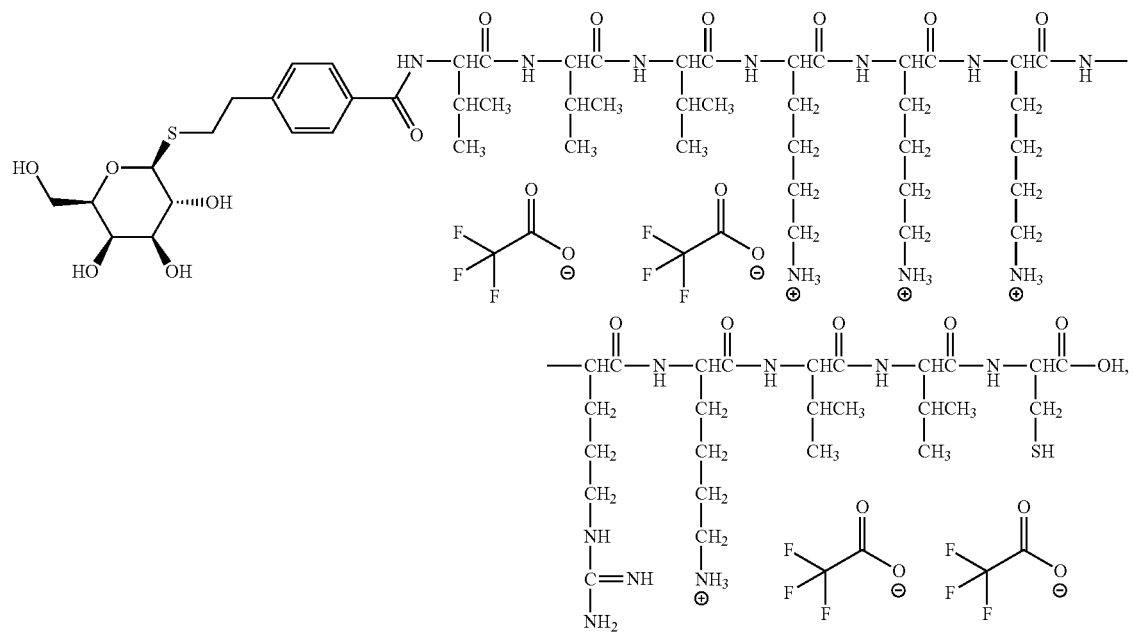

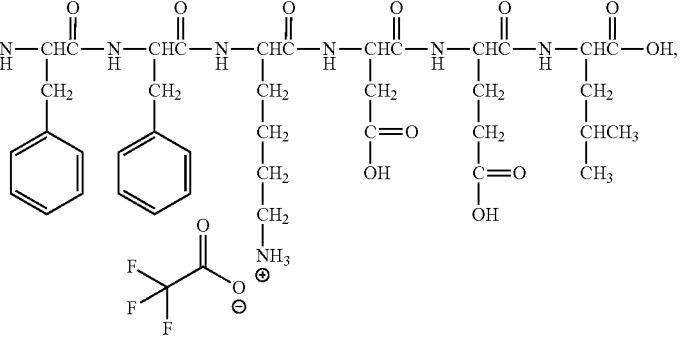

and

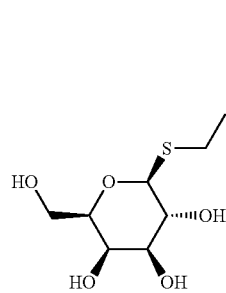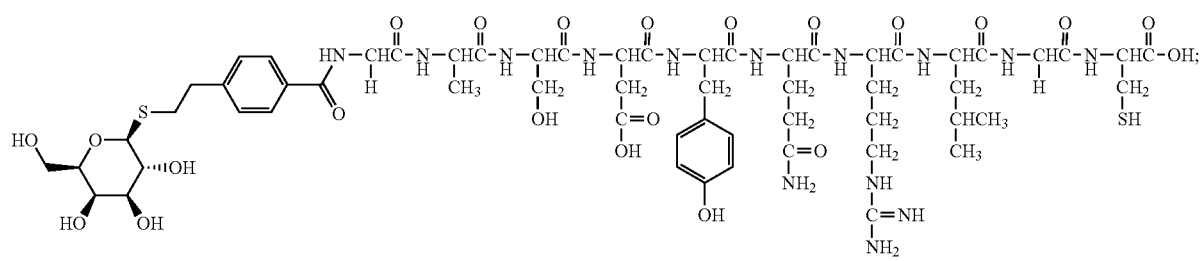

and

B. administering a therapeutically effective amount of said targeted pharmacological chaperone to a subject suffering from a disease caused by a defective protein.

2. The method of claim 1, wherein said targeted pharmacological chaperone further comprises one or more substituents selected from the group consisting of an unsubstituted carboxylic acid ester and an alkyloxy substituted carboxylic acid ester.

3. The method of claim 2, wherein said substituent is selected from the group consisting of an acetoxymethyl (AM) ester and an acetate ester.

4. A method as in claim 1, wherein the targeted pharmacological chaperone or chaperones are administered to the subject undergoing enzyme replacement therapy (ERT) for the disease, wherein the targeted pharmacological chaperone acts to deliver the enzyme into the cells and partition it into specific organelles within the diseased patient cells.

5. A composition having the general formula:

T-LINK-DRUG where T represents a targeting group that is a peptide having an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25;

where DRUG represents a small molecule compound selected from the group consisting of deoxynojirimycin, deoxygalactonojirimycin, N-butyldeoxynojirimycin, N-alkylgalactonojirimycin, N-butyldeoxymannonojirimycin, N-alkyl-deoxymannonojirimycin, N-butyl-2-deoxy-2-N-acetylnojirimycin, N-alkyl-2-deoxy-2-N-acetylnojirimycin, 1-deoxygalactonojirimycin N-butylmaleimide, 1-deoxymannonojirimycin N-butylmaleimide, 1-deoxynojirimycin N-ethylmaleimide, D-Glucosamine N-butylmaleimide, 1-thio-deoxyglucose, p-carboxyphenethyl-1-thio-1-deoxy-glucose, and 2-[4-(5-carboxypentyl)phenyl]ethyl-1-deoxy-1-thio-β-D-glucopyranoside, and N-(4'-maleimidobutyl)-1-deoxynojirimycin; and where LINK represents an optional linking group having 1-20 non-hydrogen atoms selected from the group consisting of C, N, O and S composed of any combination of chemical bonds, including ether, thioether, succinylthioether, benzylthioether, amine, ester, carboxamide, sulfonamide, hydrazide bonds, and single, double, triple carbon-carbon bonds, and aromatic or heteroaromatic bonds.

6. The composition of claim 5, wherein the LINK groups are composed of any combination of single carbon-carbon bonds and carbon-sulfur bonds including methylenes, oligomethylenes, phenylenes, thienyls, carboxamides, and sulfonamides.

7. The composition of claim 5, wherein LINK contains 1-6 carbon atoms and has the formula $-(CH_2)_a(N(COCH_2)_z-$, where a has any value from 0-5 and z is 1 or 2.

8. The composition of claim 5, wherein LINK has the formula $-(CH_2)_a(N(COPCH_2)_z-$, where a has any value from 0-5.

9. The composition of claim 5, wherein the LINK contains a reactive group selected from the group consisting of carboxyl, maleimide, benzylchloromethyl, iodoacetamide or a peptide reactive functionality for attachment of LINK to the Targeting Group T.

10. The composition of claim 5, wherein said composition further comprises one or more substituents selected from the group consisting of an unsubstituted carboxylic acid ester and an alkyloxy substituted carboxylic acid ester.

11. The composition of claim 10, wherein said substituent is selected from the group consisting of an acetoxymethyl (AM) ester and an acetate ester.

12. The composition of claim 5, wherein said composition has a formula selected from the group consisting of:

A.

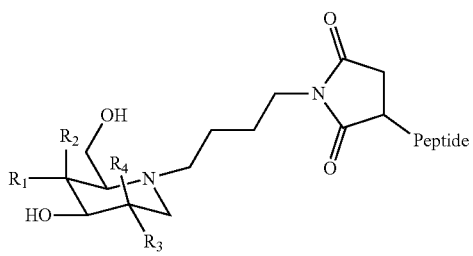

where R1, R2, R3 and R4 are independently selected from the group consisting of H and OH, and
where peptide comprises an amino acid having a sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25;

B.

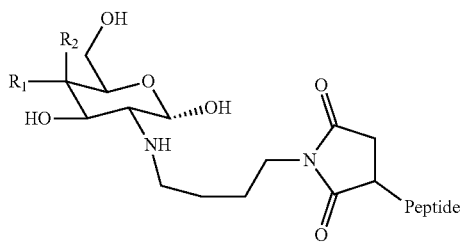

where R1 and R2 are independently selected from the group consisting of H and OH, and
where peptide comprises an amino acid having a sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25; and

C.

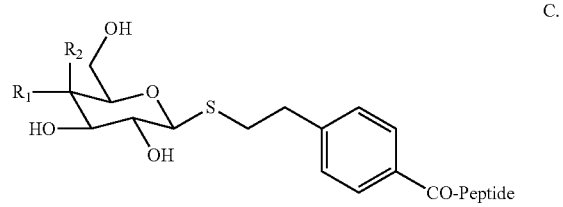

where R1 and R2 are independently selected from the group consisting of H and OH, and where peptide comprises an amino acid having a sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25.

13. A composition having a formula selected from the group consisting of: